US006682892B2

(12) United States Patent
Homa et al.

(10) Patent No.: US 6,682,892 B2
(45) Date of Patent: Jan. 27, 2004

(54) METHOD FOR TREATING HERPES VIRUSES

(75) Inventors: Fred L. Homa, Kalamazoo, MI (US); Michael W. Wathen, Portage, MI (US); Todd A. Hopkins, Galesburg, MI (US); Darrell R. Thomsen, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/904,065

(22) Filed: Jul. 12, 2001

(65) Prior Publication Data

US 2002/0076789 A1 Jun. 20, 2002

Related U.S. Application Data

(60) Provisional application No. 60/218,118, filed on Jul. 13, 2000, and provisional application No. 60/283,880, filed on Apr. 13, 2001.

(51) Int. Cl.[7] ................................................. C12Q 1/68
(52) U.S. Cl. ........................ 435/6; 435/235.1; 435/325; 435/5; 514/258
(58) Field of Search ............................. 435/6, 5, 235.1, 435/325; 514/258

(56) References Cited

U.S. PATENT DOCUMENTS

| 4,559,157 A |   | 12/1985 | Smith et al. .................. 252/90 |
| 4,608,392 A |   | 8/1986  | Jacquet et al. ............... 514/844 |
| 4,820,508 A |   | 4/1989  | Wortzman .................... 424/59 |
| 4,938,949 A |   | 7/1990  | Borch et al. .................. 424/10 |
| 4,992,478 A |   | 2/1991  | Geria .......................... 514/782 |
| 5,543,413 A | * | 8/1996  | Townsend et al. .......... 514/258 |

FOREIGN PATENT DOCUMENTS

| EP | 0097633     | 1/1984  | .......... G01N/33/54 |
| WO | WO94/24296  | 10/1994 | .......... C12N/15/86 |
| WO | WO98/04707  | 2/1998  | .......... C12N/15/38 |
| WO | WO00/40561  | 7/2000  | ......... C07D/215/16 |
| WO | WO00/40563  | 7/2000  | ......... C07D/215/56 |

OTHER PUBLICATIONS

Tatrowicz et al , Journal of Virological Methods, 1991, vol. 35, pp. 207–215.*

Prichard et al , Journal of Virological Methods, 1990, vol. 28, pp. 101–106.*

* cited by examiner

*Primary Examiner*—Ali R. Salimi
(74) *Attorney, Agent, or Firm*—Lucy X. Yang

(57) ABSTRACT

The present invention relates to a method for selecting an anti-herpes viral compound and a method for selectively inhibiting herpesvirus in a human host in need of such treatment. The present invention relates to a method for selecting an anti-herpes viral compound and a method for selectively inhibiting herpesvirus in a human host in need of such treatment.

15 Claims, 35 Drawing Sheets

Figure 1A  4-HQ, 4-oxo-DHQ and 4-oxo-DHTP antiviral compounds
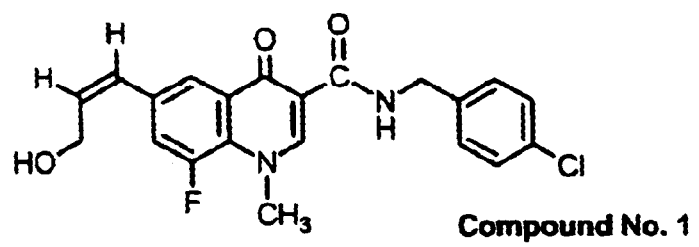
Compound No. 1
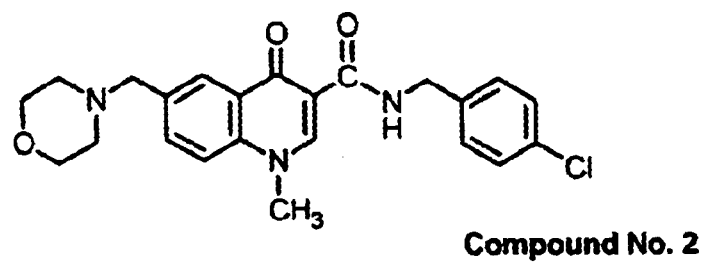
Compound No. 2
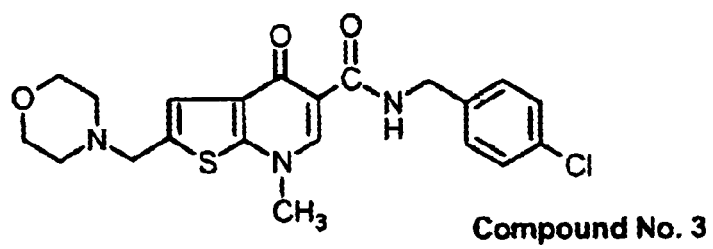
Compound No. 3
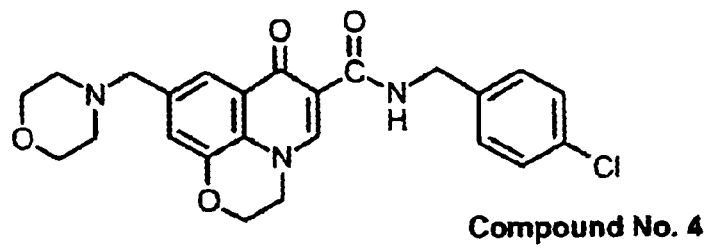
Compound No. 4
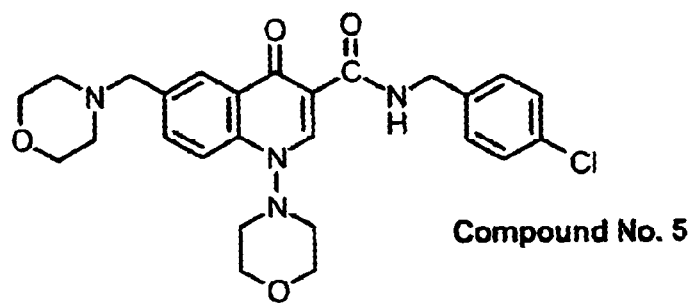
Compound No. 5

Figure 1B  4-HQ, 4-oxo-DHQ and 4-oxo-DHTP antiviral compounds
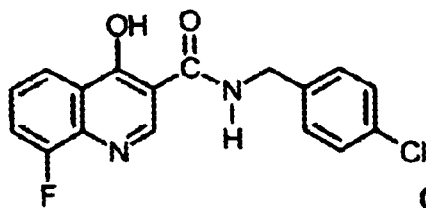
Compound No. 6
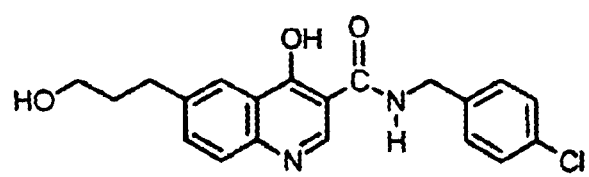
Compound No. 7
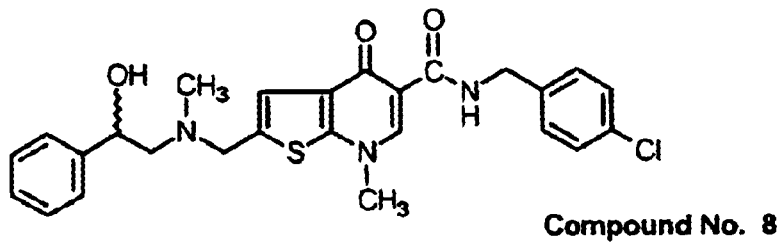
Compound No. 8
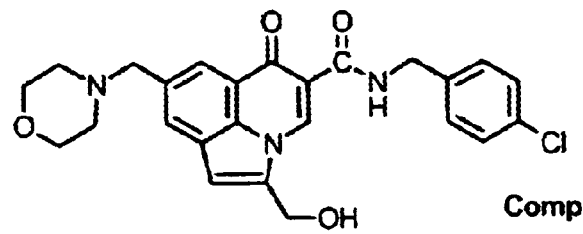
Compound No. 9
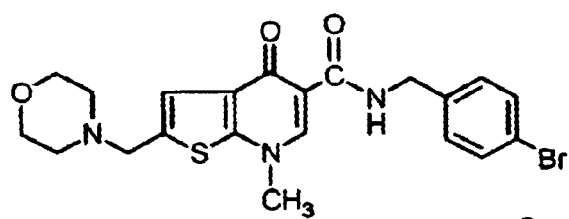
Compound No. 10

Figure 1C   4-HQ, 4-ox -DHQ and 4-oxo-DHTP antiviral compounds
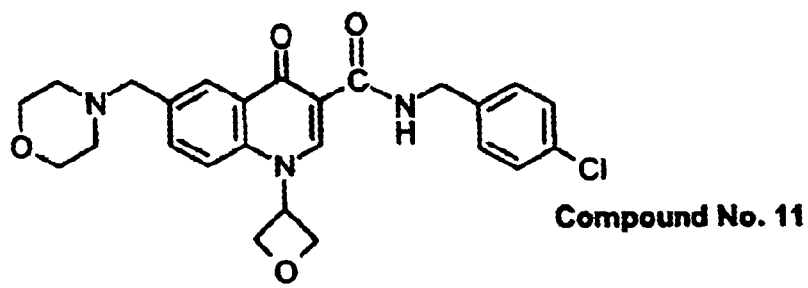
Compound No. 11
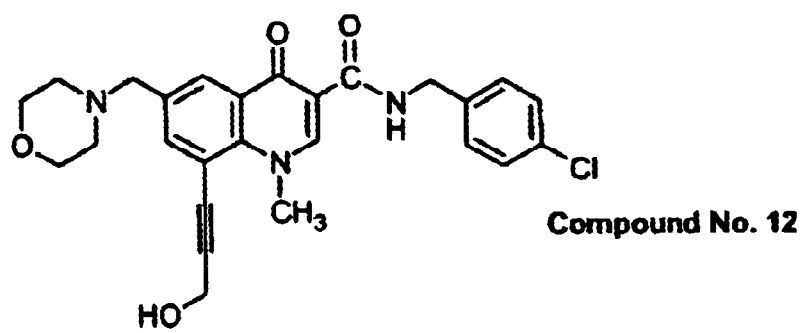
Compound No. 12
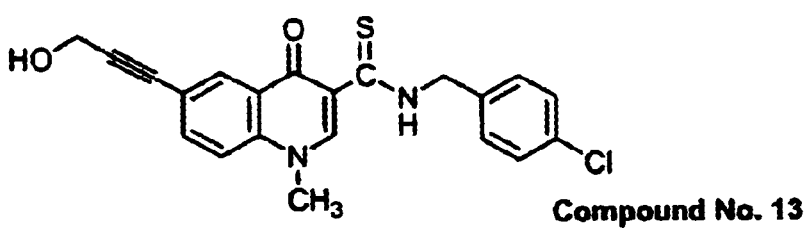
Compound No. 13
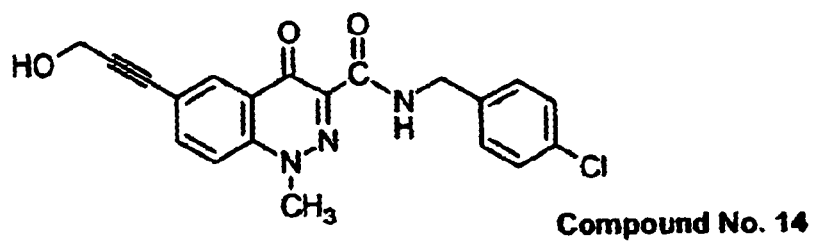
Compound No. 14

Figure 1D  4-HQ, 4-oxo-DHQ and 4-oxo-DHTP antiviral compounds
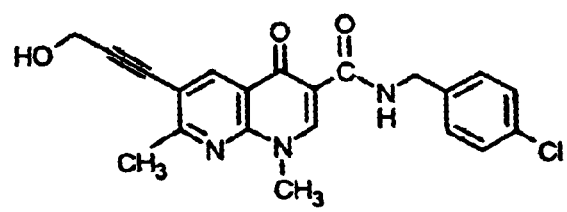
Compound No.15
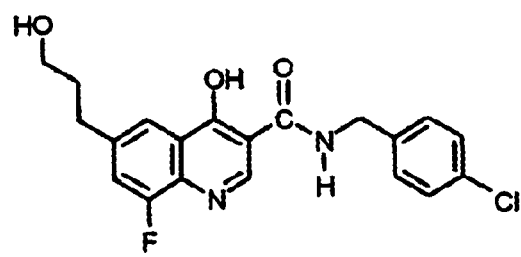
Compound 17

Figure 2. The HSV1 (KOS Strain) DNA Polymerase Amino Acid 823 is Critical for Resistance to 4-Hydroxyquinolines and Related Compounds
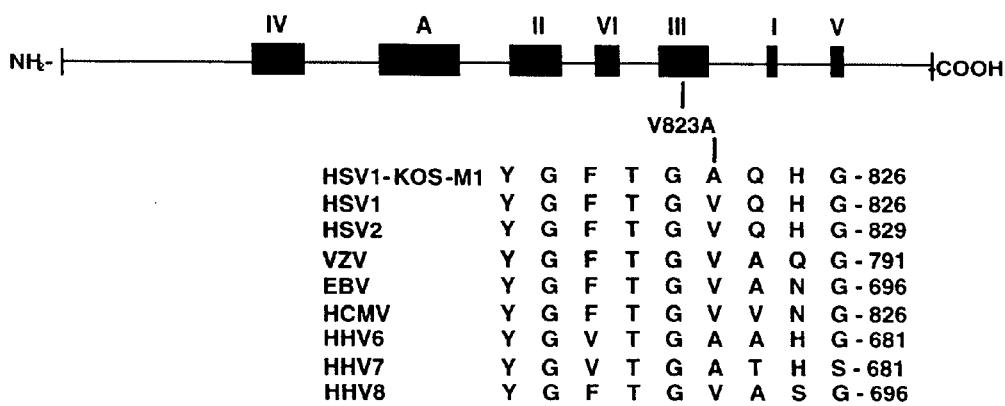
Schematic of HSV1 polymerase illustrating the conserved regions A and I-VI found in class 2 polymerases. Also shown are the amino acid sequence for the highly conserved herpesvirus domain in region III which surrounds the HSV1 amino acid 823.

Figure 3      Serial Passage of HSV-1 in Presence of 20 µM compound 17
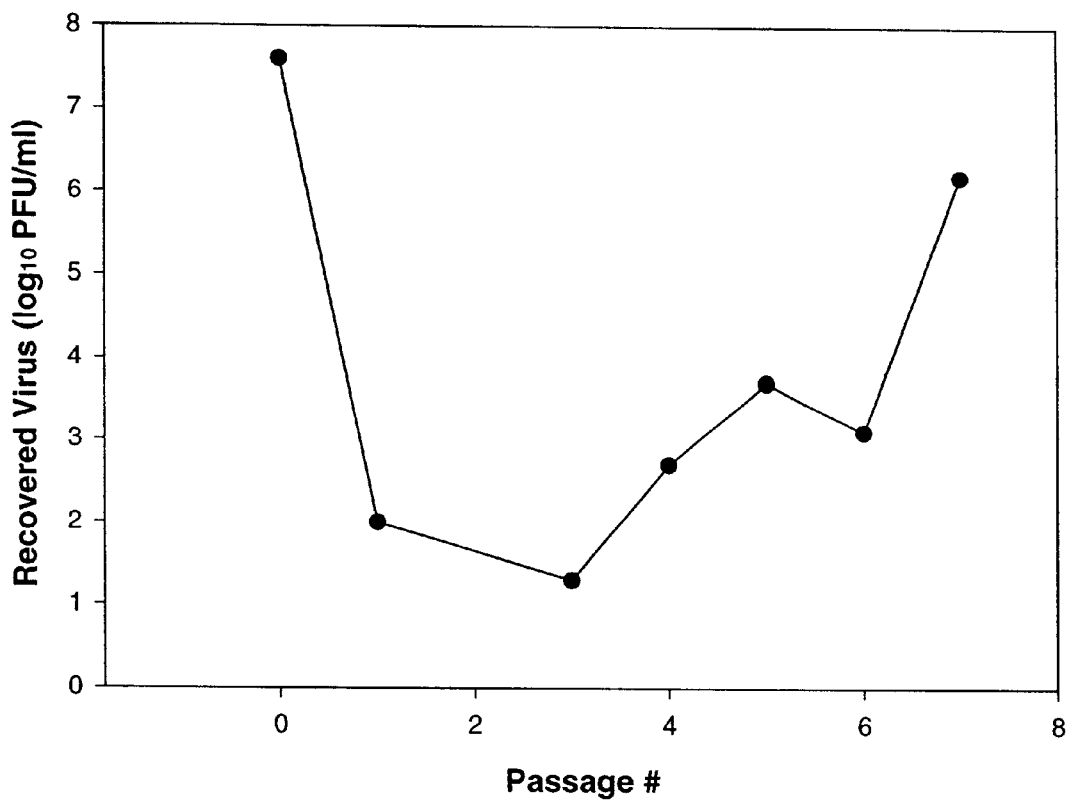

Figure 4A  Comparison of Wild type HSV-1 and HSV-2 DNA Polymerases Amino Acid Sequences Aligned by Amino Acid Homology*

```
HSV2-MS      MFCAAGGPTS PGGKSAARAA SGFFAPHNPR GATQTAPPPC RRQNFYNPHL -50
HSV2-186     MFCAAGGPAS PGGKSAARAA SGFFAPHNPR GATQTAPPPC RRQNFYNPHL -50
HSV1-Kos     MFSGGGGPLS PGGKSAARAA SGFFAPAGPR GAGR.GPPPC LRQNFYNPYL -49
HSV1-Patton  MFSGGGGPLS PGGKSAARAA SGFFAPAGPR GAGR.GPPPC LRQNFYNPYL -49
HSV1-DJL     MFSGGGGPLS PGGKSAARAA SGFFAPAGPR GAGR.GPPPC LRQNFYNPYL -49
HSV1-F       MFSGGGGPLS PGGKSAARAA SGFFAPAGPR GAGR.GPPPC LRQNFYNPYL -49

HSV2-MS      AQTGTQPKAP GPAQRHTYYS ECDEFRFIAP RSLDEDAPAE QRTGVHDGRL -100
HSV2-186     AQTGTQPKAP GPAQRHTYYS ECDEFRFIAP RSLDEDAPAE QRTGVHDGRL -100
HSV1-Kos     APVGTQQKPT GPTQRHTYYS ECDEFRFIAP RVLDEDAPPE KRAGVHDGHL -99
HSV1-Patton  APVGTQQKPT GPTQRHTYYS ECDEFRFIAP RVLDEDAPPE KRAGVHDGHL -99
HSV1-DJ1     APVGTQQKPT GPTQRHTYYS ECDEFRFIAP RVLDEDAPPE KRAGVHDGHL -99
HSV1-F       APVGTQQKPT GPTQRHTYYS ECDEFRFIAP RVLDEDAPPE KRAGVHDGHL -99

HSV2-MS      RRAPKVYCGG DERDVLRVGP EGFWPRRLRL WGGADHAPKG FDPTVTVFHV -150
HSV2-186     RRAPKVYCGG DERDVLRVGP EGFWPRRLRL WGGADHAPEG FDPTVTVFHV -150
HSV-Kos      KRAPKVYCGG DERDVLRVGS GGFWPRRSRL WGGVDHAPAG FNPTVTVFHV -149
HSV1-Patton  KRAPKVYCGG DERDVLRVGS GGFWPRRSRL WGGVDHAPAG FNPTVTVFHV -149
HSV1-DJL     KRAPKVYCGG DERDVLRVGS GGFWPRRSRL WGGVDHAPAG FNPTVTVFHV -149
HSV1-F       KRAPKVYCGG DERDVLRVGS GGFWPRRSRL WGGVDHAPAG FNPTVTVFHV -149

HSV2-MS      YDILEHVEHA YSMRAAQLHE RFMDAITPAG TVITLLGLTP EGHRVAVHVY -200
HSV2-186     YDILEHVEHA YSMRAAQLHE RFMDAITPAG TVITLLGLTP EGHRVAVHVY -200
HSV-Kos      YDILENVEHA YGMRAAQFHA RFMDAITPTG TVITLLGLTP EGHRVAVHVY -199
HSV1-Patton  YDILENVEHA YGMRAAQFHA RFMDAITPTG TVITLLGLTP EGHRVAVHVY -199
HSV1-DJL     YDILENVEHA YGMRAAQFHA RFMDAITPTG TVITLLGLTP EGHRVAVHVY -199
HSV1-F       YDILENVEHA YGMRAAQFHA RFMDAITPTG TVITLLGLTP EGHRVAVHVY -199

HSV2-MS      GTRQYFYMNK AEVDRHLQCR APRDLCERLA AALRESPGAS FRGISADHFE -250
HSV2-186     GTRQYFYMNK AEVDRHLQCR APRDLCERLA AALRESPGAS FRGISADHFE -250
HSV-Kos      GTRQYFYMNK EEVDRHLQCR APRDLCERMA AALRESPGAS FRGISADHFE -249
HSV1-Patton  GTRQYFYMNK EEVDRHLQCR APRDLCERMA AALRESPGAS FRGISADHFE -249
HSV1-DJL     GTRQYFYMNK EEVDRHLQCR APRDLCERMA AALRESPGAS FRGISADHFE -249
HSV1-F       GTRQYFYMNK EEVDRHLQCR APRDLCERMA AALRESPGAS FRGISADHFE -249

HSV2-MS      AEVVERADVY YYETRPTLYY RVFVRSGRAL AYLCDNFCPA IRKYEGGVDA -300
HSV2-186     AEVVERADVY YYETRPTLYY RVFVRSGRAL AYLCDNFCPA IRKYEGGVDA -300
HSV-Kos      AEVVERTDVY YYETRPALFY RVYVRSGRVL SYLCDNFCPA IKKYEGGVDA -299
HSV1-Patton  AEVVERTDVY YYETRPALFY RVYVRSGRVL SYLCDNFCPA IKKYEGGVDA -299
HSV1-DJL     AEVVERTDVY YYETRPALFY RVYVRSGRVL SYLCDNFCPA IKKYEGGVDA -299
HSV1-F       AEVVERTDVY YYETRPALFY RVYVRSGRVL SYLCDNFCPA IKKYEGGVDA -299

HSV2-MS      TTRFILDNPG FVTFGWYRLK PGRGNAPAQP RPPTAFGTSS DVEFNCTADN -350
HSV2-186     TTRFILDNPG FVTFGWYRLK PGRGNAPAQP RPPTAFGTSS DVEFNCTADN -350
HSV-Kos      TTRFILDNPG FVTFGWYRLK PGRNNTLAQP RAPMAFGTSS DVEFNCTADN -349
HSV1-Patton  TTRFILDNPG FVTFGWYRLK PGRNNTLAQP RAPMAFGTSS DVEFNCTADN -349
HSV1-DJL     TTRFILDNPG FVTFGWYRLK PGRNNTLAQP RAPMAFGTSS DVEFNCTADN -349
HSV1-F       TTRFILDNPG FVTFGWYRLK PGRNNTLAQP RAPMAFGTSS DVEFNCTADN -349

HSV2-MS      LAVEGAMCDL PAYKLMCFDI ECKAGGEDEL AFPVAERPED LVIQISCLLY -400
HSV2-186     LAVEGAMCDL PAYKLMCFDI ECKAGGEDEL AFPVAERPED LVIQISCLLY -400
HSV-Kos      LAIEGGMSDL PAYKLMCFDI ECKAGGEDEL AFPVAGHPED LVIQISCLLY -399
HSV1-Patton  LAIEGGMSDL PAYKLMCFDI ECKAGGEDEL AFPVAGHPED LVIQISCLLY -399
HSV1-DJL     LAIEGGMSDL PAYKLMCFDI ECKAGGEDEL AFPVAGHPED LVIQISCLLY -399
HSV1-F       LAIEGGMSDL PAYKLMCFDI ECKAGGEDEL AFPVAGHPED LVIQISCLLY -399

HSV2-MS      DLSTTALEHI LLFSLGSCDL PESHLSDLAS RGLPAPVVLE FDSEFEMLLA -450
```

Figure 4B   Comparison of Wild type HSV-1 and HSV-2 DNA Polymerases Amino Acid Sequences Alligned by Amino Acid Homology*

```
HSV2-186       DLSTTALEHI LLFSLGSCDL PESHLSDLAS RGLPAPVVLE FDSEFEMLLA -450
HSV-Kos        DLSTTALEHV LLFSLGSCDL PESHLNELAA RGLPTPVVLE FDSEFEMLLA -449
HSV1-Patton    DLSTTALEHV LLFSLGSCDL PESHLNELAA RGLPTPVVLE FDSEFEMLLA -449
HSV1-DJL       DLSTTALEHV LLFSLGSCDL PESHLNELAA RGLPTPVVLE FDSEFEMLLA -449
HSV1-F         DLSTTALEHV LLFSLGSCDL PESHLNELAA RGLPTPVVLE FDSEFEMLLA -449

HSV2-MS        FMTFVKQYGP EFVTGYNIIN FDWPFVLTKL TEIYKVPLDG YGRMNGRGVF -500
HSV2-186       FMTFVKQYGP EFVTGYNIIN FDWPFVLTKL TEIYKVPLDG YGRMNGRGVF -500
HSV-Kos        FMTLVKQYGP EFVTGYNIIN FDWPFLLAKL TDIYKVPLDG YGRMNGRGVF -499
HSV1-Patton    FMTLVKQYGP EFVTGYNIIN FDWPFLLAKL TDIYKVPLDG YGRMNGRGVF -499
HSV1-DJL       FMTLVKQYGP EFVTGYNIIN FDWPFLLAKL TDIYKVPLDG YGRMNGRGVF -499
HSV1-F         FMTLVKQYGP EFVTGYNIIN FDWPFLLAKL TDIYKVPLDG YGRMNGRGVF -499

HSV2-MS        RVWDIGQSHF QKRSKIKVNG MVNIDMYGII TDKVKLSSYK LNAVAEAVLK -550
HSV2-186       RVWDIGQSHF QKRSKIKVNG MVNIDMYGII TDKVKLSSYK LNAVAEAVLK -550
HSV-Kos        RVWDIGQSHF QKRSKIKVNG MVNIDMYGII TDKIKLSSYK LNAVAEAVLK -549
HSV1-Patton    RVWDIGQSHF QKRSKIKVNG MVNIDMYGII TDKIKLSSYK LNAVAEAVLK -549
HSV1-DJL       RVWDIGQSHF QKRSKIKVNG MVNIDMYGII TDKIKLSSYK LNAVAEAVLK -549
HSV1-F         RVWDIGQSHF QKRSKIKVNG MVNIDMYGII TDKIKLSSYK LNAVAEAVLK -549

HSV2-MS        DKKKDLSYRD IPAYYASGPA QRGVIGEYCV QDSLLVGQLF FKFLPHLELS -600
HSV2-186       DKKKDLSYRD IPAYYASGPA QRGVIGEYCV QDSLLVGQLF FKFLPHLELS -600
HSV-Kos        DKKKDLSYRD IPAYYAAGPA QRGVIGEYCI QDSLLVGQLF FKFLPHLELS -599
HSV1-Patton    DKKKDLSYRD IPAYYAAGPA QRGVIGEYCI QDSLLVGQLF FKFLPHLELS -599
HSV1-DJL       DKKKDLSYRD IPTYYAAGPA QRGVIGEYCI QDSLLVGQLF FKFLPHLELS -599
HSV1-F         DKKKDLSYRD IPAYYAAGPA QRGVIGEYCI QDSLLVGQLF FKFLPHLELS -599

HSV2-MS        AVARLAGINI TRTIYDGQQI RVFTCLLRLA GQKGFILPDT QGRFRGLDKE -650
HSV2-186       AVARLAGINI TRTIYDGQQI RVFTCLLRLA GQKGFILPDT QGRFRGLDKE -650
HSV-Kos        AVARLAGINI TRTIYDGQQI RVFTCLLRLA DQKGFILPDT QGRFRGAGGE -649
HSV1-Patton    AVARLAGINI TRTIYDGQQI RVFTCLLRLA DQKGFILPDT QGRFRGAGGE -649
HSV1-DJL       AVARLAGINI TRTIYDGQQI RVFTCLLRLA DQKGFILPDT QGRFRGAGGE -649
HSV1-F         AVARLAGINI TRTIYDGQQI RVFTCLLRLA DQKGFILPDT QGRFRGGGGE -649

HSV2-MS        APKRPAVPRG EGERPGDGNG DEDKDDDE.. DEDGDERE.E VARETGGRHV -697
HSV2-186       APKRPAVPRG EGERPGDGNG DEDKDDDEDG DEDGDERE.E VARETGGRHV -697
HSV-Kos        APKRPAAARE DEERP..... EEEGEDEDER EEGGGEREPE GARETAGRHV -694
HSV1-Patton    APKRPAAARE DEERP..... EEEGEDEDER EEGGGEREPE GARETAGRHV -694
HSV1-DJL       APKRPAAARE DEERP..... EEEGEDENER EEGGGEREPE GARETAGRHV -694
HSV1-F         APKRPAAARE DEERP..... EEEGEDEDER EEGGGEREPE GARETAGRHV -694

HSV2-MS        GYQGARVLDP TSGFHVDPVV VFDFASLYPS IIQAHNLCFS TLSLRPEAVA -747
HSV2-186       GYQGARVLDP TSGFHVDPVV VFDFASLYPS IIQAHNLCFS TLSLRPEAVA -749
HSV-Kos        GYQGARVLDP TSGFHVNPVV VFDFASLYPS IIQAHNLCFS TLSLRADAVA -744
HSV1-Patton    GYQGARVLDP ISGFHVNPVV VFDFASLYPS IIQAHNLCFS TLSLRADAVA -744
HSV1-DJL       GYQGARVLDP TSGFHVNPVV VFDFASLYPS IIQAHNLCFS TLSLRADAVA -744
HSV1-F         GYQGARVLDP TSGFHVNPVV VFDFASLYPS IIQAHNLCFS TLSLRADAVA -744

HSV2-MS        HLEADRDYLE IEVGGRRLFF VKAHVRESLL SILLRDWLAM RKQIRSRIPQ -797
HSV2-186       HLEADRDYLE IEVGGRRLFF VKAHVRESLL SILLRDWLAM RKQIRSRIPQ -799
HSV-Kos        HLEAGKDYLE IEVGGRRLFF VKAHVRESLL SILLRDWLAM RKQIRSRIPQ -794
HSV1-Patton    HLEAGKDYLE IEVGGRRLFF VKAHVRESLL SILLRDWLAM RKQIRSRIPQ -794
HSV1-DJL       HLEAGKDYLE IEVGGRRLFF VKAHVRESLL SILLRDWLAM RKQIRSRIPQ -794
HSV1-F         HLEAGKDYLE IEVGGRRLFF VKAHVRESLL SILLRDWLAM RKQIRSRIPQ -794

HSV2-MS        STPEEAVLLD KQQAAIKVVC NSVYGFTGVQ HGLLPCLHVA ATVTTIGREM -847
HSV2-186       SPPEEAVLLD KQQAAIKVVC NSVYGFTGVQ HGLLPCLHVA ATVTTIGREM -849
HSV-Kos        SSPEEAVLLD KQQAAIKVVC NSVYGFTGVQ HGLLPCLHVA ATVTTIGREM -844
```

Figure 4C  Comparison of Wild type HSV-1 and HSV-2 DNA Polymerases Amino Acid Sequences Alligned by Amino Acid Homology*

```
HSV1-Patton    SSPEEAVLLD  KQQAAIKVVC  NSVYGFTGVQ  HGLLPCLHVA  ATVTTIGREM  -844
HSV1-DJL       SSPEEAVLLD  KQQAAIKVVC  NSVYGFTGVQ  HGLLPCLHVA  ATVTTIGREM  -844
HSV1-F         SSPEEAVLLD  KQQAAIKVVC  NSVYGFTGVQ  HGLLPCLHVA  ATVTTIGREM  -844

HSV2-MS        LLATRAYVHA  RWAEFDQLLA  DFPEAAGMRA  PGPYSMRIIY  GDTDSIFVLC  -897
HSV2-186       LLATRAYVHA  RWAEFDQLLA  DFPEAAGMRA  PGPYSMRIIY  GDTDSIFVLC  -899
HSV-Kos        LLATREYVHA  RWAAPEQLLA  DFPEAADMRA  PGPYSMRIIY  GDTDSIFVLC  -894
HSV1-Patton    LLATREYVHA  RWAAFEQLLA  DFPEAADMRA  PGPYSMRIIY  GDTDSIFVLC  -894
HSV1-DJL       LLATREYVHA  RWAAPEQLLA  DFPEAADMRA  PGPYSMRIIY  GDTDSIFVLC  -894
HSV1-F         LLATREYVHA  RWAAFEQLLA  DFPEAADMRA  PGPYSMRIIY  GDTDSIFVLC  -894

HSV2-MS        RGLTAAGLVA  MGDKMASHIS  RALFLPPIKL  ECEKTFTKLL  LIAKKKYIGV  -947
HSV2-186       RGLTAAGLVA  MGDKMASHIS  RALFLPPIKL  ECEKTFTKLL  LIAKKKYIGV  -949
HSV-Kos        RGLTAAGLTA  MGDKMASHIS  RALFLPPIKL  ECEKTFTKLL  LIAKKKYIGV  -944
HSV1-Patton    RGLTAAGLTA  MGDKMASHIS  RALFLPPIKL  ECEKTFTKLL  LIAKKKYIGV  -944
HSV1-DJL       RGLTAAGLTA  VGDKMASHIS  RALFLPPIKL  ECEKTFTKLL  LIAKKKYIGV  -944
HSV1-F         RGLTAAGLTA  VGDKMASHIS  RALFLSPIKL  ECEKTFTKLL  LIAKKKYIGV  -944

HSV2-MS        ICGGKMLIKG  VDLVRKNNCA  FINRTSRALV  DLLFYDDTVS  GAAAALAERP  -997
HSV2-186       ICGGKMLIKG  VDLVRKNNCA  FINRTSRALV  DLLFYDDTVS  GAAAALAERP  -999
HSV-Kos        IYGGKMLIKG  VDLVRKNNCA  FINRTSRALV  DLLFYDDTVS  GAAAALAERP  -994
HSV1-Patton    IYGGKMLIKG  VDLVRKNNCA  FINRTSRALV  DLLFYDDTVS  GAAAALAERP  -994
HSV1-DJL       IYGGKMLIKG  VDLVRKNNCA  FINRTSRALV  DLLFYDDTVS  GAAAALAERP  -994
HSV1-F         IYGGKMLIKG  VDLVRKNNCA  FINRTSRALV  DLLFYDDTVS  GAAAALAERP  -994

HSV2-MS        AEEWLARPLP  EGLQAFGAVL  VDAHRRITDP  ERDIQDFVLT  AELSRHPRAY  -1047
HSV2-186       AEEWLARPLP  EGLQAFGAVL  VDAHRRITDP  ERDIQDFVLT  AELSRHPRAY  -1049
HSV-Kos        AEEWLARPLP  EGLQAFGAVL  VDAHRRITDP  ERDIQDFVLT  AELSRHPRAY  -1044
HSV1-Patton    AEEWLARPLP  EGLQAFGAVL  VDAHRRITDP  ERDIQDFVLT  AELSRHPRAY  -1044
HSV1-DJL       AEEWLARPLP  EGLQAFGAVL  VDAHRRITDP  ERDIQDFVLT  AELSRHPRAY  -1044
HSV1-F         AEEWLARPLP  EGLQAFGAVL  VDAHRRITDP  ERDIQDFVLT  AELSRHPRAY  -1044

HSV2-MS        TNKRLAHLTV  YYKLMARRAQ  VPSIKDRIPY  VIVAQTREVE  ETVARLAALR  -1097
HSV2-186       TNKRLAHLTV  YYKLMARRAQ  VPSIKDRIPY  VIVAQTREVE  ETVARLAALR  -1099
HSV-Kos        TNKRLAHLTV  YYKLMARRAQ  VPSIKDRIPY  VIVAQTREVE  ETVARLAALR  -1094
HSV1-Patton    TNKRLAHLTV  YYKLMARRAQ  VPSIKDRIPY  VIVAQTREVE  ETVARLAALR  -1094
HSV1-DJL       TNKRLAHLTV  YYKLMARRAQ  VPSIKDRIPY  VIVAQTREVE  ETVARLAALR  -1094
HSV1-F         TNKRLAHLTV  YYKLMARRAQ  VPSIKDRIPY  VIVAQTREVE  ETVARLAALR  -1094

HSV2-MS        ELDAAAPGDE  PAPPAALPSP  AKRPRETPSH  ADPPGGASKP  RKLLVSELAE  -1147
HSV2-186       ELDAAAPGDE  PAPPAALPSP  AKRPRETPSH  ADPPGGASKP  RKLLVSELAE  -1149
HSV-Kos        ELDAAAPGDE  PAPPAALPSP  AKRPRETPSH  ADPPGGASKP  RKLLVSELAE  -1144
HSV1-Patton    ELDAAAPGDE  PAPPAALPSP  AKRPRETPSP  ADPPGGASKP  RKLLVSELAE  -1144
HSV1-DJL       ELDAAAPGDE  PAPPAALPSP  AKRPRETPSP  ADPPGGASKP  RKLLVSELAE  -1144
HSV1-F         ELDAAAPGDE  PAPPAALPSP  AKRPRETPLH  ADPPGGASKP  RKLLVSELAE  -1144

HSV2-MS        DPGYAIARGV  PLNTDYYFSH  LLGAACVTFK  ALFGNNAKIT  ESLLKRFIPE  -1197
HSV2-186       DPGYAIARGV  PLNTDYYFSH  LLGAACVTFK  ALFGNNAKIT  ESLLKRFIPE  -1199
HSV-Kos        DPAYAIAHGV  ALNTDYYFSH  LLGAACVTFK  ALFGNNAKIT  ESLLKRFIPE  -1194
HSV1-Patton    DPAYAIAHGV  ALNTDYYFSH  LLGAACVTFK  ALFGNNAKIT  ESLLKRFIPE  -1194
HSV1-DJL       DPAYAIAHGV  ALNTDYYFSH  LLGAACVTFK  ALFGNNAKIT  ESLLKRFIPE  -1194
HSV1-F         DPAYAIAHGV  ALNTDYYFSH  LLGAACVTFK  ALFGNNAKIT  ESLLKRFIPE  -1194

HSV2-MS        TWHPPDDVAA  RLRAAGFGPA  GAGATAEETR  RMLHRAFDTL  A*  -1238
HSV2-186       TWHPPDDVAA  RLRAAGFGPA  GAGATAEETR  RMLHRAFDTL  A*  -1240
HSV-Kos        VWHPPDDVAA  RLRAAGFGAV  GAGATAEETR  RMLHRAFDTL  A*  -1235
HSV1-Patton    VWHPPDDVTA  RLRAAGFGAV  GAGATAEETR  RMLHRAFDTL  A*  -1235
HSV1-DJL       VWHPPDDVAA  RLRTAGFGAV  GAGATAEETR  RMLHRAFDTL  A*  -1235
```

Figure 4D   Comparison of Wild type HSV-1 and HSV-2 DNA Polymerases Amino Acid Sequences Alligned by Amino Acid Homology*

```
HSV1-F      VWHPPDDVAA RLRAAGFGAV GAGATAEETR RMLHRAFDTL A*  -1235
```

*Amino acid alignment demonstrates difference in amino acid's sequences.

*The gaps "....." indicate missing amino acids relative to other stanins.

*Wild HSV2-MS is listed as SEQ. ID NO 14.

*Wild HSV2-186 is listed as SEQ. ID NO 15.

*Wild HSV-Kos is listed as SEQ. ID NO 16.

*Wild HSV1-Patton is listed as SEQ. ID NO 17.

*Wild HSV1-DJL is listed as SEQ. ID NO 18.

*Wild HSV1-F is listed as SEQ. ID NO 19.

Figure 5A DNA and amino acid sequence list

SEQ. ID. NO. 1 DNA sequence of DNA polymerase gene for HSV2-MS-M1

1 ATGTTTTGTG CCGCGGGCGG CCCGACTTCC CCCGGGGGGA AGTCGGCGGC
51 TCGGGCGGCG TCTGGGTTTT TTGCCCCCCA CAACCCCCGG GGAGCCACCC
101 AGACGGCACC GCCGCCTTGC CGCCGGCAGA ACTTCTACAA CCCCCACCTC
151 GCTCAGACCG GAACGCAGCC AAAGGCCCCC GGGCCGGCTC AGCGCCATAC
201 GTACTACAGC GAGTGCGACG AATTTCGATT TATCGCCCCG CGTTCGCTGG
251 ACGAGGACGC CCCCGCGGAG CAGCGCACCG GGGTCCACGA CGGCCGCCTC
301 CGGCGCGCCC CTAAGGTGTA CTGCGGGGGG GACGAGCGCG ACGTCCTCCG
351 CGTGGGCCCG GAGGGCTTCT GGCCGCGTCG CTTGCGCCTG TGGGGCGGTG
401 CGGACCATGC CCCCAAGGGG TTCGACCCCA CCGTCACCGT CTTCCACGTG
451 TACGACATCC TGGAGCACGT GGAACACGCG TACAGCATGC GCGCCGCCCA
501 GCTCCACGAG CGATTTATGG ACGCCATCAC GCCCGCCGGG ACCGTCATCA
551 CGCTTCTGGG TCTGACCCCC GAAGGCCATC GCGTCGCCGT TCACGTCTAC
601 GGCACGCGGC AGTACTTTTA CATGAACAAG GCGGAGGTGG ATCGGCACCT
651 GCAGTGCCGT GCCCCGCGCG ATCTCTGCGA GCGCCTGGCG GCGGCCCTGC
701 GCGAGTCGCC GGGGGCGTCG TTCCGCGGCA TCTCCGCGGA CCACTTCGAG
751 GCGGAGGTGG TGGAGCGCGC CGACGTGTAC TATTACGAAA CGCGCCCGAC
801 CCTGTACTAC CGCGTCTTCG TGCGAAGCGG GCGCGCGCTG GCCTACCTGT
851 GCGACAACTT TTGCCCCGCG ATCAGGAAGT ACGAGGGGGG CGTCGACGCC
901 ACCACCCGGT TTATCCTGGA CAACCCGGGG TTTGTCACCT TCGGCTGGTA
951 CCGCCTCAAG CCCGGCCGCG GGAACGCGCC GGCCCAACCG CGCCCCCCGA
1001 CGGCGTTCGG AACCTCGAGC GACGTCGAGT TTAACTGCAC GGCGGACAAC
1051 CTGGCCGTCG AGGGGGCCAT GTGTGACCTG CCGGCCTACA AGCTCATGTG
1101 CTTCGATATC GAATGCAAGG CCGGGGGGGA GGACGAGCTG GCCTTTCCGG
1151 TCGCGGAACG CCCCGGAAGAC CTCGTCATCC AGATCTCCTG TCTGCTCTAC
1201 GACCTGTCCA CCACCGCCCT CGAGCACATC CTCCTGTTTT CGCTCGGATC

Figure 5B    DNA and amino acid sequence list

```
1251 CTGCGACCTC CCCGAGTCCC ACCTCAGCGA TCTCGCCTCC AGGGGCCTGC
1301 CGGCCCCCGT CGTCCTGGAG TTTGACAGCG AATTCGAGAT GCTGCTGGCC
1351 TTCATGACCT TCGTCAAGCA GTACGGCCCC GAGTTCGTGA CCGGGTACAA
1401 CATCATCAAC TTCGACTGGC CCTTCGTCCT GACCAAGCTG ACGGAGATCT
1451 ACAAGGTCCC GCTCGACGGG TACGGGCGCA TGAACGGCCG GGGTGTGTTC
1501 CGCGTGTGGG ACATCGGCCA GAGCCACTTT CAGAAGCGCA GCAAGATCAA
1551 GGTGAACGGG ATGGTGAACA TCGACATGTA CGGCATCATC ACCGACAAGG
1601 TCAAACTCTC CAGCTACAAG CTGAACGCCG TCGCCGAGGC CGTCTTGAAG
1651 GACAAGAAGA AGGATCTGAG CTACCGCGAC ATCCCCGCCT ACTACGCCTC
1701 CGGGCCCGCG CAGCGCGGGG TGATCGGCGA GTATTGTGTG CAGGACTCGC
1751 TGCTGGTCGG GCAGCTGTTC TTCAAGTTTC TGCCGCACCT GGAGCTTTCC
1801 GCCGTCGCGC GCCTGGCGGG CATCAACATC ACCCGCACCA TCTACGACGG
1851 CCAGCAGATC CGCGTCTTCA CGTGCCTCCT GCGCCTTGCG GGCCAGAAGG
1901 GCTTCATCCT GCCGGACACC CAGGGGCGGT TCGGGGCCT CGACAAGGAG
1951 GCGCCCAAGC GCCCGGCCGT GCCTCGGGGG AAGGGGAGC GGCCGGGGGA
2001 CGGGAACGGG GACGAGGATA AGGACGACGA CGAGGACGAG GACGGGGACG
2051 AGCGCGAGGA GGTCGCGCGC GAGACCGGGG GCCGGCACGT TGGGTACCAG
2101 GGGGCCCGGG TCCTCGACCC CACCTCCGGG TTTCACGTCG ACCCCGTGGT
2151 GGTGTTTGAC TTTGCCAGCC TGTACCCCAG CATCATCCAG GCCCACAACC
2201 TGTGCTTCAG TACGCTCTCC CTGCGGCCCG AGGCCGTCGC GCACCTGGAG
2251 GCGGACCGGG ACTACCTGGA GATCGAGGTG GGGGGCCGAC GGCTGTTCTT
2301 CGTGAAGGCC CACGTACGCG AGAGCCTGCT GAGCATCCTG CTGCGCGACT
2351 GGCTGGCCAT GCGAAAGCAG ATCCGCTCGC GGATCCCCCA GAGCACCCCC
2401 GAGGAGGCCG TCCTCCTCGA CAAGCAACAG CCGCCATCA AGGTGGTGTG
2451 CAACTCGGTG TACGGGTTCA CCGGGGCGCA GCACGGTCTT CTGCCCTGCC
2501 TGCACGTGGC CGCCACCGTG ACGACCATCG GCCGCGAGAT GCTCCTCGCG
2551 ACGCGCGCGT ACGTGCACGC GCGCTGGGCG GAGTTCGATC AGCTGCTGGC
```

Figure 5C    DNA and amino acid sequence list

```
2601 CGACTTTCCG GAGGCGGCCG GCATGCGCGC CCCCGGTCCG TACTCCATGC
2651 GCATCATCTA CGGGGACACG GACTCCATTT TCGTTTTGTG CCGCGGCCTC
2701 ACGGCCGCGG GCCTGGTGGC CATGGGCGAC AAGATGGCGA GCCACATCTC
2751 GCGCGCGCTG TTCCTCCCCC CGATCAAGCT CGAGTGCGAA AAAACGTTCA
2801 CCAAGCTGCT GCTCATCGCC AAGAAAAAGT ACATCGGCGT CATCTGCGGG
2851 GGCAAGATGC TCATCAAGGG CGTGGATCTG GTGCGCAAAA ACAACTGCGC
2901 GTTTATCAAC CGCACCTCCA GGGCCCTGGT CGACCTGCTG TTTTACGACG
2951 ATACCGTATC CGGAGCGGCC GCCGCGTTAG CCGAGCGCCC CGCAGAGGAG
3001 TGGCTGGCGC GACCCCTGCC CGAGGGACTG CAGGCGTTCG GGGCCGTCCT
3051 CGTAGACGCC CATCGGCGCA TCACCGACCC GGAGAGGGAC ATCCAGGACT
3101 TTGTCCTCAC CGCCGAACTG AGCAGACACC CGCGCGCGTA CACCAACAAG
3151 CGCCTGGCCC ACCTGACGGT GTATTACAAG CTCATGGCCC GCCGCGCGCA
3201 GGTCCCGTCC ATCAAGGACC GGATCCCGTA CGTGATCGTG GCCCAGACCC
3251 GCGAGGTAGA GGAGACGGTC GCGCGGCTGG CCGCCCTCCG CGAGCTAGAC
3301 GCCGCCGCCC CAGGGGACGA GCCCGCCCCC CCAGCGGCCC TGCCCTCCCC
3351 GGCCAAGCGC CCCCGGGAGA CGCCGTCGCA TGCCGACCCC CCGGGAGGCG
3401 CGTCCAAGCC CCGCAAGCTG CTGGTGTCCG AGCTGGCGGA GGATCCCGGG
3451 TACGCCATCG CCCGGGGCGT TCCGCTCAAC ACGGACTATT ACTTCTCGCA
3501 CCTGCTGGGG GCGGCCTGCG TGACGTTCAA GGCCCTGTTT GGAAATAACG
3551 CCAAGATCAC CGAGAGTCTG TTAAAGAGGT TTATTCCCGA GACGTGGCAC
3601 CCCCCGGACG ACGTGGCCGC GCGGCTCAGG GCCGCGGGGT TCGGGCCGGC
3651 GGGGGCCGGC GCTACGGCGG AGGAAACTCG TCGAATGTTG CATAGAGCCT
3701 TTGATACTCT AGCATGA
```

Figure 5D    DNA and amino acid sequence list

SEQ. ID. NO. 2    Amino acid sequence of DNA polymerase for HSV2-MS-M1

```
   1 MFCAAGGPTS PGGKSAARAA SGFFAPHNPR GATQTAPPPC RRQNFYNPHL
  51 AQTGTQPKAP GPAQRHTYYS ECDEFRFIAP RSLDEDAPAE QRTGVHDGRL
 101 RRAPKVYCGG DERDVLRVGP EGFWPRRLRL WGGADHAPKG FDPTVTVFHV
 151 YDILEHVEHA YSMRAAQLHE RFMDAITPAG TVITLLGLTP EGHRVAVHVY
 201 GTRQYFYMNK AEVDRHLQCR APRDLCERLA AALRESPGAS FRGISADHFE
 251 AEVVERADVY YYETRPTLYY RVFVRSGRAL AYLCDNFCPA IRKYEGGVDA
 301 TTRFILDNPG FVTFGWYRLK PGRGNAPAQP RPPTAFGTSS DVEFNCTADN
 351 LAVEGAMCDL PAYKLMCFDI ECKAGGEDEL AFPVAERPED LVIQISCLLY
 401 DLSTTALEHI LLFSLGSCDL PESHLSDLAS RGLPAPVVLE FDSEFEMLLA
 451 FMTFVKQYGP EFVTGYNIIN FDWPFVLTKL TEIYKVPLDG YGRMNGRGVF
 501 RVWDIGQSHF QKRSKIKVNG MVNIDMYGII TDKVKLSSYK LNAVAEAVLK
 551 DKKKDLSYRD IPAYYASGPA QRGVIGEYCV QDSLLVGQLF FKFLPHLELS
 601 AVARLAGINI TRTIYDGQQI RVFTCLLRLA GQKGFILPDT QGRFRGLDKE
 651 APKRPAVPRG EGERPGDGNG DEDKDDDEDE DGDEREEVAR ETGGRHVGYQ
 701 GARVLDPTSG FHVDPVVVFD FASLYPSIIQ AHNLCFSTLS LRPEAVAHLE
 751 ADRDYLEIEV GGRRLFFVKA HVRESLLSIL LRDWLAMRKQ IRSRIPQSTP
 801 EEAVLLDKQQ AAIKVVCNSV YGFTGAQHGL LPCLHVAATV TTIGREMLLA
 851 TRAYVHARWA EFDQLLADFP EAAGMRAPGP YSMRIIYGDT DSIFVLCRGL
 901 TAAGLVAMGD KMASHISRAL FLPPIKLECE KTFTKLLLIA KKKYIGVICG
 951 GKMLIKGVDL VRKNNCAFIN RTSRALVDLL FYDDTVSGAA AALAERPAEE
1001 WLARPLPEGL QAFGAVLVDA HRRITDPERD IQDFVLTAEL SRHPRAYTNK
1051 RLAHLTVYYK LMARRAQVPS IKDRIPYVIV AQTREVEETV ARLAALRELD
1101 AAAPGDEPAP PAALPSPAKR PRETPSHADP PGGASKPRKL LVSELAEDPG
1151 YAIARGVPLN TDYYFSHLLG AACVTFKALF GNNAKITESL LKRFIPETWH
1201 PPDDVAARLR AAGFGPAGAG ATAEETRRML HRAFDTLA*
```

Figure 5E  DNA and amino acid sequence list

SEQ.ID.NO. 3  DNA sequence of DNA polymerase gene for HSV2-186-M1

```
   1 ATGTTTTGTG CCGCGGGCGG CCCGGCTTCC CCCGGGGGGA AGTCGGCGGC
  51 TCGGGCGGCG TCTGGGTTTT TTGCCCCCCA CAACCCCCGG GGAGCCACCC
 101 AGACGGCACC GCCGCCTTGC CGCCGGCAGA ACTTCTACAA CCCCCACCTC
 151 GCTCAGACCG GAACGCAGCC AAAGGCCCCC GGGCCGGCTC AGCGCCATAC
 201 GTACTACAGC GAGTGCGACG AATTTCGATT TATCGCCCCG CGTTCGCTGG
 251 ACGAGGACGC CCCCGCGGAG CAGCGCACCG GGGTCCACGA CGGCCGCCTC
 301 CGGCGCGCCC CTAAGGTGTA CTGCGGGGGG GACGAGCGCG ACGTCCTCCG
 351 CGTGGGCCCG GAGGGCTTCT GGCCGCGTCG CTTGCGCCTG TGGGGCGGTG
 401 CGGACCATGC CCCCGAGGGG TTCGACCCCA CCGTCACCGT CTTCCACGTG
 451 TACGACATCC TGGAGCACGT GGAACACGCG TACAGCATGC GCGCCGCCCA
 501 GCTCCACGAG CGATTTATGG ACGCCATCAC GCCCGCCGGG ACCGTCATCA
 551 CGCTTCTGGG TCTGACCCCC GAAGGCCATC GCGTCGCCGT TCACGTCTAC
 601 GGCACGCGGC AGTACTTTTA CATGAACAAG GCGGAGGTGG ATCGGCACCT
 651 GCAGTGCCGT GCCCCGCGCG ATCTCTGCGA GCGCCTGGCG GCGGCCCTGC
 701 GCGAGTCGCC GGGGGCGTCG TTCCGCGGCA TCTCCGCGGA CCACTTCGAG
 751 GCGGAGGTGG TGGAGCGCGC CGACGTGTAC TATTACGAAA CGCGCCCGAC
 801 CCTGTACTAC CGCGTCTTCG TGCGAAGCGG GCGCGCGCTG GCCTACCTGT
 851 GCGACAACTT TTGCCCCGCG ATCAGGAAGT ACGAGGGGGG CGTCGACGCC
 901 ACCACCCGGT TATCCTGGA CAACCCGGGG TTTGTCACCT TCGGCTGGTA
 951 CCGCCTCAAG CCCGGCCGCG GGAACGCGCC GGCCCAACCG CGCCCCCCGA
1001 CGGCGTTCGG AACCTCGAGC GACGTCGAGT TAACTGCAC GGCGGACAAC
1051 CTGGCCGTCG AGGGGGCCAT GTGTGACCTG CCGGCCTACA AGCTCATGTG
1101 CTTCGATATC GAATGCAAGG CCGGGGGGGA GGACGAGCTG GCCTTTCCGG
1151 TCGCGGAACG CCCGGAAGAC CTCGTCATCC AGATCTCCTG TCTGCTCTAC
1201 GACCTGTCCA CCACCGCCCT CGAGCACATC CTCCTGTTTT CGCTCGGATC
```

Figure 5F   DNA and amino acid sequence list

```
1251 CTGCGACCTC CCCGAGTCCC ACCTCAGCGA TCTCGCCTCC AGGGGCCTGC
1301 CGGCCCCCGT CGTCCTGGAG TTTGACAGCG AATTCGAGAT GCTGCTGGCC
1351 TTCATGACCT TCGTCAAGCA GTACGGCCCC GAGTTCGTGA CCGGGTACAA
1401 CATCATCAAC TTCGACTGGC CCTTCGTCCT GACCAAGCTG ACGGAGATCT
1451 ACAAGGTCCC GCTCGACGGG TACGGGCGCA TGAACGGCCG GGGTGTGTTC
1501 CGCGTGTGGG ACATCGGCCA GAGCCACTTT CAGAAGCGCA GCAAGATCAA
1551 GGTGAACGGG ATGGTGAACA TCGACATGTA CGGCATCATC ACCGACAAGG
1601 TCAAACTCTC CAGCTACAAG CTGAACGCCG TCGCCGAGGC CGTCTTGAAG
1651 GACAAGAAGA AGGATCTGAG CTACCGCGAC ATCCCCGCCT ACTACGCCTC
1701 CGGGCCCGCG CAGCGCGGGG TGATCGGCGA GTATTGTGTG CAGGACTCGC
1751 TGCTGGTCGG GCAGCTGTTC TTCAAGTTTC TGCCGCACCT GGAGCTTTCC
1801 GCCGTCGCGC GCCTGGCGGG CATCAACATC ACCCGCACCA TCTACGACGG
1851 CCAGCAGATC CGCGTCTTCA CGTGCCTCCT GCGCCTTGCG GGCCAGAAGG
1901 GCTTCATCCT GCCGGACACC CAGGGGCGGT TCGGGGCCT CGACAAGGAG
1951 GCGCCCAAGC GCCCGGCCGT GCCTCGGGGG GAAGGGGAGC GGCCGGGGGA
2001 CGGGAACGGG GACGAGGATA AGGACGACGA CGAGGACGGG GACGAGGACG
2051 GGGACGAGCG CGAGGAGGTC GCGCGCGAGA CCGGGGGCCG GCACGTTGGG
2101 TACCAGGGGG CCCGGGTCCT CGACCCCACC TCCGGGTTTC ACGTCGACCC
2151 CGTGGTGGTG TTTGACTTTG CCAGCCTGTA CCCCAGCATC ATCCAGGCCC
2201 ACAACCTGTG CTTCAGTACG CTCTCCCTGC GGCCCGAGGC CGTCGCGCAC
2251 CTGGAGGCGG ACCGGGACTA CCTGGAGATC GAGGTGGGGG CCGACGGCT
2301 GTTCTTCGTG AAGGCCCACG TACGCGAGAG CCTGCTGAGC ATCCTGCTGC
2351 GCGACTGGCT GGCCATGCGA AAGCAGATCC GCTCGCGGAT CCCCCAGAGC
2401 CCCCCCGAGG AGGCCGTCCT CCTCGACAAG CAACAGGCCG CCATCAAGGT
2451 GGTGTGCAAC TCGGTGTACG GGTTCACCGG GGCGCAGCAC GGTCTTCTGC
2501 CCTGCCTGCA CGTGGCCGCC ACCGTGACGA CCATCGGCCG CGAGATGCTC
```

Figure 5G    DNA and amino acid sequence list

```
2551 CTCGCGACGC GCGCGTACGT GCACGCGCGC TGGGCGGAGT TCGATCAGCT

2601 GCTGGCCGAC TTTCCGGAGG CGGCCGGCAT GCGCGCCCCC GGTCCGTACT

2651 CCATGCGCAT CATCTACGGG GACACGGACT CCATTTTCGT TTTGTGCCGC

2701 GGCCTCACGG CCGCGGGCCT GGTGGCCATG GGCGACAAGA TGGCGAGCCA

2751 CATCTCGCGC GCGCTGTTCC TCCCCCCGAT CAAGCTCGAG TGCGAAAAAA

2801 CGTTCACCAA GCTGCTGCTC ATCGCCAAGA AAAGTACAT CGGCGTCATC

2851 TGCGGGGGCA AGATGCTCAT CAAGGGCGTG GATCTGGTGC GCAAAAACAA

2901 CTGCGCGTTT ATCAACCGCA CCTCCAGGGC CCTGGTCGAC CTGCTGTTTT

2951 ACGACGATAC CGTATCCGGA GCGGCCGCCG CGTTAGCCGA GCGCCCCGCA

3001 GAGGAGTGGC TGGCGCGACC CCTGCCCGAG GGACTGCAGG CGTTCGGGGC

3051 CGTCCTCGTA GACGCCCATC GGCGCATCAC CGACCCGGAG AGGGACATCC

3101 AGGACTTTGT CCTCACCGCC GAACTGAGCA GACACCCGCG CGCGTACACC

3151 AACAAGCGCC TGGCCCACCT GACGGTGTAT TACAAGCTCA TGGCCCGCCG

3201 CGCGCAGGTC CCGTCCATCA AGGACCGGAT CCCGTACGTG ATCGTGGCCC

3251 AGACCCGCGA GGTAGAGGAG ACGGTCGCGC GGCTGGCCGC CCTCCGCGAG

3301 CTAGACGCCG CCGCCCCAGG GGACGAGCCC GCCCCCCCAG CGGCCCTGCC

3351 CTCCCCGGCC AAGCGCCCCC GGGAGACGCC GTCGCATGCC GACCCCCCGG

3401 GAGGCGCGTC CAAGCCCCGC AAGCTGCTGG TGTCCGAGCT GGCGGAGGAT

3451 CCCGGGTACG CCATCGCCCG GGGCGTTCCG CTCAACACGG ACTATTACTT

3501 CTCGCACCTG CTGGGGGCGG CCTGCGTGAC GTTCAAGGCC CTGTTTGGAA

3551 ATAACGCCAA GATCACCGAG AGTCTGTTAA AGAGGTTTAT TCCCGAGACG

3601 TGGCACCCCC CGGACGACGT GGCCGCGCGG CTCAGGGCCG CGGGGTTCGG

3651 GCCGGCGGGG GCCGGCGCTA CGGCGGAGGA AACTCGTCGA ATGTTGCATA

3701 GAGCCTTTGA TACTCTAGCA TGA
```

Figure 5H  DNA and amino acid sequence list

SEQ.ID.NO. 4   Amino acid sequence of DNA polymerase for HSV2-186-M1

```
   1 MFCAAGGPAS PGGKSAARAA SGFPAPHNPR GATQTAPPPC RRQNFYNPHL
  51 AQTGTQPKAP GPAQRHTYYS ECDEFRFIAP RSLDEDAPAE QRTGVHDGRL
 101 RRAPKVYCGG DERDVLRVGP EGFWPRRLRL WGGADHAPEG FDPTVTVFHV
 151 YDILEHVEHA YSMRAAQLHE RFMDAITPAG TVITLLGLTP EGHRVAVHVY
 201 GTRQYFYMNK AEVDRHLQCR APRDLCERLA AALRESPGAS FRGISADHFE
 251 AEVVERADVY YYETRPTLYY RVFVRSGRAL AYLCDNFCPA IRKYEGGVDA
 301 TTRFILDNPG FVTFGWYRLK PGRGNAPAQP RPPTAFGTSS DVEFNCTADN
 351 LAVEGAMCDL PAYKLMCFDI ECKAGGEDEL AFPVAERPED LVIQISCLLY
 401 DLSTTALEHI LLFSLGSCDL PESHLSDLAS RGLPAPVVLE FDSEFEMLLA
 451 FMTFVKQYGP EFVTGYNIIN FDWPFVLTKL TEIYKVPLDG YGRMNGRGVF
 501 RVWDIGQSHF QKRSKIKVNG MVNIDMYGII TDKVKLSSYK LNAVAEAVLK
 551 DKKKDLSYRD IPAYYASGPA QRGVIGEYCV QDSLLVGQLF FKFLPHLELS
 601 AVARLAGINI TRTIYDGQQI RVFTCLLRLA GQKGFILPDT QGRFRGLDKE
 651 APKRPAVPRG EGERPGDGNG DEDKDDDEDG DEDGDEREEV ARETGGRHVG
 701 YQGARVLDPT SGFHVDPVVV FDFASLYPSI IQAHNLCFST LSLRPEAVAH
 751 LEADRDYLEI EVGGRRLFFV KAHVRESLLS ILLRDWLAMR KQIRSRIPQS
 801 PPEEAVLLDK QQAAIKVVCN SVYGFTGAQH GLLPCLHVAA TVTTIGREML
 851 LATRAYVHAR WAEFDQLLAD FPEAAGMRAP GPYSMRIIYG DTDSIFVLCR
 901 GLTAAGLVAM GDKMASHISR ALFLPPIKLE CEKTFTKLLL IAKKKYIGVI
 951 CGGKMLIKGV DLVRKNNCAF INRTSRALVD LLFYDDTVSG AAAALAERPA
1001 EEWLARPLPE GLQAFGAVLV DAHRRITDPE RDIQDFVLTA ELSRHPRAYT
1051 NKRLAHLTVY YKLMARRAQV PSIKDRIPYV IVAQTREVEE TVARLAALRE
1101 LDAAAPGDEP APPAALPSPA KRPRETPSHA DPPGGASKPR KLLVSELAED
1151 PGYAIARGVP LNTDYYPSHL LGAACVTFKA LFGNNAKITE SLLKRFIPET
1201 WHPPDDVAAR LRAAGFGPAG AGATAEETRR MLHRAFDTLA *
```

Figure 5I    DNA and amino acid sequence list

SEQ.ID.NO. 5    DNA sequence of DNA polymerase gene for HSV1-KOS-M1

```
   1 ATGTTTTCCG GTGGCGGCGG CCCGCTGTCC CCCGGAGGAA AGTCGGCGGC
  51 CAGGGCGGCG TCCGGGTTTT TTGCGCCCGC CGGCCCTCGC GGAGCCGGCC
 101 GGGGACCCCC GCCTTGTTTG AGGCAAAACT TTTACAACCC CTACCTCGCC
 151 CCAGTCGGGA CGCAACAGAA GCCGACCGGG CCAACCCAGC GCCATACGTA
 201 CTATAGCGAA TGCGATGAAT TTCGATTCAT CGCCCCGCGG GTGCTGGACG
 251 AGGATGCCCC CCCGGAGAAG CGCGCCGGGG TGCACGACGG TCACCTCAAG
 301 CGCGCCCCCA AGGTGTACTG CGGGGGGGAC GAGCGCGACG TCCTCCGCGT
 351 CGGGTCGGGC GGCTTCTGGC CGCGGCGCTC GCGCCTGTGG GGCGGCGTGG
 401 ACCACGCCCC GGCGGGGTTC AACCCCACCG TCACCGTCTT TCACGTGTAC
 451 GACATCCTGG AGAACGTGGA GCACGCGTAC GGCATGCGCG CGGCCCAGTT
 501 CCACGCGCGG TTTATGGACG CCATCACACC GACGGGGACC GTCATCACGC
 551 TCCTGGGCCT GACTCCGGAA GGCCACCGGG TGGCCGTTCA CGTTTACGGC
 601 ACGCGGCAGT ACTTTTACAT GAACAAGGAG GAGGTTGACA GGCACCTACA
 651 ATGCCGCGCC CCACGAGATC TCTGCGAGCG CATGGCCGCG GCCCTGCGCG
 701 AGTCCCCGGG CGCGTCGTTC CGCGGCATCT CCGCGGACCA CTTCGAGGCG
 751 GAGGTGGTGG AGCGCACCGA CGTGTACTAC TACGAGACGC GCCCCGCTCT
 801 GTTTTACCGC GTCTACGTCC GAAGCGGGCG CGTGCTGTCG TACCTGTGCG
 851 ACAACTTCTG CCCGGCCATC AAGAAGTACG AGGGTGGGGT CGACGCCACC
 901 ACCCGGTTCA TCCTGGACAA CCCCGGGTTC GTCACCTTCG GCTGGTACCG
 951 TCTCAAACCG GGCCGGAACA ACACGCTAGC CCAGCCGCGG GCCCCGATGG
1001 CCTTCGGGAC ATCCAGCGAC GTCGAGTTTA ACTGTACGGC GGACAACCTG
1051 GCCATCGAGG GGGGCATGAG CGACCTACCG GCATACAAGC TCATGTGCTT
1101 CGATATCGAA TGCAAGGCGG GGGGGGAGGA CGAGCTGGCC TTTCCGGTGG
1151 CCGGGCACCC GGAGGACCTG GTTATTCAGA TATCCTGTCT GCTCTACGAC
1201 CTGTCCACCA CCGCCCTGGA GCACGTCCTC CTGTTTTCGC TCGGTTCCTG
```

Figure 5J   DNA and amino acid sequence list

```
1251 CGACCTCCCC GAATCCCACC TGAACGAGCT GGCGGCCAGG GGCCTGCCCA
1301 CGCCCGTGGT TCTGGAATTC GACAGCGAAT TCGAGATGCT GTTGGCCTTC
1351 ATGACCCTTG TGAAACAGTA CGGCCCCGAG TTCGTGACCG GGTACAACAT
1401 CATCAACTTC GACTGGCCCT TCTTGCTGGC CAAGTTGACG GACATTTACA
1451 AGGTCCCCCT GGACGGGTAC GGCCGCATGA ACGGCCGGGG CGTGTTTCGC
1501 GTGTGGGACA TAGGCCAGAG CCACTTCCAG AAGCGCAGCA AGATAAAGGT
1551 GAACGGCATG GTGAACATCG ACATGTACGG GATCATAACC GACAAGATCA
1601 AGCTCTCGAG CTACAAGCTC AACGCCGTGG CCGAAGCCGT CCTGAAGGAC
1651 AAGAAGAAGG ACCTGAGCTA TCGCGACATC CCCGCCTACT ACGCCGCCGG
1701 GCCCGCGCAA CGCGGGGTGA TCGGCGAGTA CTGCATACAG GATTCCCTGC
1751 TGGTGGGCCA GCTGTTTTTT AAGTTTTTGC CCCATCTGGA GCTCTCGGCC
1801 GTCGCGCGCT TGGCGGGTAT TAACATCACC CGCACCATCT ACGACGGCCA
1851 GCAGATCCGC GTCTTTACGT GCCTGCTGCG CCTGGCCGAC CAGAAGGGCT
1901 TTATTCTGCC GGACACCCAG GGGCGATTTA GGGGCGCCGG GGGGGAGGCG
1951 CCCAAGCGTC CGGCCGCAGC CCGGGAGGAC GAGGAGCGGC CAGAGGAGGA
2001 GGGGAGGAC GAGGACGAAC GCGAGGAGGG CGGGGGCGAG CGGGAGCCGG
2051 AGGGCGCGCG GGAGACCGCC GGCCGGCACG TGGGGTACCA GGGGGCCAGG
2101 GTCCTTGACC CCACTTCCGG GTTTCACGTG AACCCCGTGG TGGTGTTCGA
2151 CTTTGCCAGC CTGTACCCCA GCATCATCCA GGCCCACAAC CTGTGCTTCA
2201 GCACGCTCTC CCTGAGGGCC GACGCAGTGG CGCACCTGGA GGCGGGCAAG
2251 GACTACCTGG AGATCGAGGT GGGGGGGCGA CGGCTGTTCT TCGTCAAGGC
2301 TCACGTGCGA GAGAGCCTCC TCAGCATCCT CCTGCGGGAC TGGCTCGCCA
2351 TGCGAAAGCA GATCCGCTCG CGGATTCCCC AGAGCAGCCC CGAGGAGGCC
2401 GTGCTCCTGG ACAAGCAGCA GGCCGCCATC AAGGTCGTGT GTAACTCGGT
2451 GTACGGGTTC ACGGGAGCGC AGCACGGACT CCTGCCGTGC CTGCACGTTG
2501 CCGCGACGGT GACGACCATC GGCCGCGAGA TGCTGCTCGC GACCCGCGAG
```

Figure 5K    DNA and amino acid sequence list

```
2551 TACGTCCACG CGCGCTGGGC GGCCTTCGAA CAGCTCCTGG CCGATTTCCC
2601 GGAGGCGGCC GACATGCGCG CCCCCGGGCC CTATTCCATG CGCATCATCT
2651 ACGGGGACAC GGACTCCATA TTTGTGCTGT GCCGCGGCCT CACGGCCGCC
2701 GGGCTGACGG CCATGGGCGA CAAGATGGCG AGCCACATCT CGCGCGCGCT
2751 GTTTCTGCCC CCCATCAAAC TCGAGTGCGA AAAGACGTTC ACCAAGCTGC
2801 TGCTGATCGC CAAGAAAAAG TACATCGGCG TCATCTACGG GGGTAAGATG
2851 CTCATCAAGG GCGTGGATCT GGTGCGCAAA AACAACTGCG CGTTTATCAA
2901 CCGCACCTCC AGGGCCCTGG TCGACCTGCT GTTTTACGAC GATACCGTAT
2951 CCGGAGCGGC CGCCGCGTTA GCCGAGCGCC CCGCAGAGGA GTGGCTGGCG
3001 CGACCCCTGC CCGAGGGACT GCAGGCGTTC GGGGCCGTCC TCGTAGACGC
3051 CCATCGGCGC ATCACCGACC CGGAGAGGGA CATCCAGGAC TTTGTCCTCA
3101 CCGCCGAACT GAGCAGACAC CCGCGCGCGT ACACCAACAA GCGCCTGGCC
3151 CACCTGACGG TGTATTACAA GCTCATGGCC CGCCGCGCGC AGGTCCCGTC
3201 CATCAAGGAC CGGATCCCGT ACGTGATCGT GGCCCAGACC CGCGAGGTAG
3251 AGGAGACGGT CGCGCGGCTG GCCGCCCTCC GCGAGCTAGA CGCCGCCGCC
3301 CCAGGGGACG AGCCCGCCCC CCCCGCGGCC CTGCCCTCCC CGGCCAAGCG
3351 CCCCCGGGAG ACGCCGTCGC ATGCCGACCC CCCGGGAGGC GCGTCCAAGC
3401 CCCGCAAGCT GCTGGTGTCC GAGCTGGCCG AGGATCCCGC ATACGCCATT
3451 GCCCACGGCG TCGCCCTGAA CACGGACTAT TACTTCTCCC ACCTGTTGGG
3501 GGCGGCGTGC GTGACATTCA AGGCCCTGTT TGGGAATAAC GCCAAGATCA
3551 CCGAGAGTCT GTTAAAAAGG TTTATTCCCG AAGTGTGGCA CCCCCCGGAC
3601 GACGTGGCCG CGCGGCTCCG GGCCGCAGGG TTCGGGGCGG TGGGTGCCGG
3651 CGCTACGGCG GAGGAAACTC GTCGAATGTT GCATAGAGCC TTTGATACTC
3701 TAGCATGA
```

Figure 5L    DNA and amino acid sequence list

SEQ.ID.NO. 6    Amino acid sequence of DNA polymerase for HSV1-KOS-M1

```
   1  MFSGGGGPLS PGGKSAARAA SGFFAPAGPR GAGRGPPPCL RQNFYNPYLA
  51  PVGTQQKPTG PTQRHTYYSE CDEFRFIAPR VLDEDAPPEK RAGVHDGHLK
 101  RAPKVYCGGD ERDVLRVGSG GFWPRRSRLW GGVDHAPAGF NPTVTVFHVY
 151  DILENVEHAY GMRAAQFHAR FMDAITPTGT VITLLGLTPE GHRVAVHVYG
 201  TRQYFYMNKE EVDRHLQCRA PRDLCERMAA ALRESPGASF RGISADHFEA
 251  EVVERTDVYY YETRPALFYR VYVRSGRVLS YLCDNFCPAI KKYEGGVDAT
 301  TRFILDNPGF VTFGWYRLKP GRNNTLAQPR APMAFGTSSD VEFNCTADNL
 351  AIEGGMSDLP AYKLMCFDIE CKAGGEDELA FPVAGHPEDL VIQISCLLYD
 401  LSTTALEHVL LFSLGSCDLP ESHLNELAAR GLPTPVVLEF DSEFEMLLAF
 451  MTLVKQYGPE FVTGYNIINF DWPFLLAKLT DIYKVPLDGY GRMNGRGVFR
 501  VWDIGQSHFQ KRSKIKVNGM VNIDMYGIIT DKIKLSSYKL NAVAEAVLKD
 551  KKKDLSYRDI PAYYAAGPAQ RGVIGEYCIQ DSLLVGQLFF KFLPHLELSA
 601  VARLAGINIT RTTYDGQQIR VFTCLLRLAD QKGFILPDTQ GRFRGAGGEA
 651  PKRPAAARED EERPEEEGED EDEREEGGGE REPEGARETA GRHVGYQGAR
 701  VLDPTSGFHV NPVVVFDFAS LYPSIIQAHN LCFSTLSLRA DAVAHLEAGK
 751  DYLEIEVGGR RLFFVKAHVR ESLLSILLRD WLAMRKQIRS RIPQSSPEEA
 801  VLLDKQQAAI KVVCNSVYGF TGAQHGLLPC LHVAATVTTI GREMLLATRE
 851  YVHARWAAFE QLLADFPEAA DMRAPGPYSM RIIYGDTDSI FVLCRGLTAA
 901  GLTAMGDKMA SHISRALFLP PIKLECEKTF TKLLLIAKKK YIGVIYGGKM
 951  LIKGVDLVRK NNCAFINRTS RALVDLLFYD DTVSGAAAAL AERPAEEWLA
1001  RPLPEGLQAF GAVLVDAHRR ITDPERDIQD FVLTAELSRH PRAYTNKRLA
1051  HLTVYYKLMA RRAQVPSIKD RIPYVIVAQT REVEETVARL AALRELDAAA
1101  PGDEPAPPAA LPSPAKRPRE TPSHADPPGG ASKPRKLLVS ELAEDPAYAI
1151  AHGVALNTDY YFSHLLGAAC VTFKALFGNN AKITESLLKR FIPEVWHPPD
1201  DVAARLRAAG FGAVGAGATA EETRRMLHRA FDTLA*
```

Figure 5M    DNA and amino acid sequence list

SEQ.ID.NO. 7    DNA sequence of HSV polymerase gene for HSV1-F-M1

```
   1  ATGTTTTCCG GTGGCGGCGG CCCGCTGTCC CCCGGAGGAA AGTCGGCGGC
  51  CAGGGCGGCG TCCGGGTTTT TTGCGCCCGC CGGCCCTCGC GGAGCCGGCC
 101  GGGGACCCCC GCCTTGCTTG AGGCAAAACT TTTACAACCC CTACCTCGCC
 151  CCAGTCGGGA CGCAACAGAA GCCGACCGGG CCAACCCAGC GCCATACGTA
 201  CTATAGCGAA TGCGATGAAT TTCGATTCAT CGCCCCGCGG GTGCTGGACG
 251  AGGATGCCCC CCCGGAGAAG CGCGCCGGGG TGCACGACGG TCACCTCAAG
 301  CGCGCCCCCA AGGTGTACTG CGGGGGGGAC GAGCGCGACG TCCTCCGCGT
 351  CGGGTCGGGC GGCTTCTGGC CGCGGCGCTC GCGCCTGTGG GGCGGCGTGG
 401  ACCACGCCCC GGCGGGGTTC AACCCCACCG TCACCGTCTT TCACGTGTAC
 451  GACATCCTGG AGAACGTGGA GCACGCGTAC GGCATGCGCG CGGCCCAGTT
 501  CCACGCGCGG TTTATGGACG CCATCACACC GACGGGGACC GTCATCACGC
 551  TCCTGGGCCT GACTCCGGAA GGCCACCGGG TGGCCGTTCA CGTTTACGGC
 601  ACGCGGCAGT ACTTTTACAT GAACAAGGAG GAGGTCGACA GGCACCTACA
 651  ATGCCGCGCC CCACGAGATC TCTGCGAGCG CATGGCCGCG GCCCTGCGCG
 701  AGTCCCCGGG CGCGTCGTTC CGCGGCATTT CCGCGGACCA CTTCGAGGCG
 751  GAGGTGGTGG AGCGCACCGA CGTGTACTAC TACGAGACGC GCCCCGCTCT
 801  GTTTTACCGC GTCTACGTCC GAAGCGGGCG CGTGCTGTCG TACCTGTGCG
 851  ACAACTTCTG CCCGGCCATC AAGAAGTACG AGGGTGGGGT CGACGCCACC
 901  ACCCGGTTCA TCCTGGACAA CCCCGGGTTC GTCACCTTCG GCTGGTACCG
 951  TCTCAAACCG GGCCGGAACA ACACGCTAGC CCAGCCGCGG GCCCCGATGG
1001  CCTTCGGGAC ATCCAGCGAC GTCGAGTTTA ACTGTACGGC GGACAACCTG
1051  GCCATCGAGG GGGCATGAG CGACCTACCG GCATACAAGC TCATGTGCTT
1101  CGATATCGAA TGCAAGGCGG GGGGGAGGA CGAGCTGGCC TTTCCGGTGG
1151  CCGGGCACCC GGAGGACCTG GTCATCCAGA TATCCTGTCT GCTCTACGAC
1201  CTGTCCACCA CCGCCCTGGA GCACGTCCTC CTGTTTTCGC TCGGTTCCTG
1251  CGACCTCCCC GAATCCCACC TGAACGAGCT GGCGGCCAGG GGCCTGCCCA
```

Figure 5N   DNA and amino acid sequence list

```
1301  CGCCCGTGGT TCTGGAATTC GACAGCGAAT TCGAGATGCT GTTGGCCTTC
1351  ATGACCCTTG TGAAACAGTA CGGCCCCGAG TTCGTGACCG GGTACAACAT
1401  CATCAACTTC GACTGGCCCT TCTTGCTGGC CAAGCTGACG GACATTTACA
1451  AGGTCCCCCT GGACGGGTAC GGCCGCATGA ACGGCCGGGG CGTGTTTCGC
1501  GTGTGGGACA TAGGCCAGAG CCACTTCCAG AAGCGCAGCA AGATAAAGGT
1551  GAACGGCATG GTGAACATCG ACATGTACGG GATTATAACC GACAAGATCA
1601  AGCTCTCGAG CTACAAGCTC AACGCCGTGG CCGAAGCCGT CCTGAAGGAC
1651  AAGAAGAAGG ACCTGAGCTA TCGCGACATC CCGCCTACT ACGCCGCCGG
1701  GCCCGCGCAA CGCGGGGTGA TCGGCGAGTA CTGCATACAG GATTCCCTGC
1751  TGGTGGGCCA GCTGTTTTTT AAGTTTTTGC CCCATCTGGA GCTCTCGGCC
1801  GTCGCGCGCT TGGCGGGTAT TAACATCACC CGCACCATCT ACGACGGCCA
1851  GCAGATCCGC GTCTTTACGT GCCTGCTGCG CCTGGCCGAC CAGAAGGGCT
1901  TTATTCTGCC GGACACCCAG GGGCGATTTA GGGCGGCGG GGGGAGGCG
1951  CCCAAGCGTC CGGCCGCAGC CCGGGAGGAC GAGGAGCGGC CAGAGGAGGA
2001  GGGGAGGAC GAGGACGAAC GCGAGGAGGG CGGGGGCGAG CGGGAGCCGG
2051  AGGGCGCGCG GGAGACCGCC GGCCGGCACG TGGGGTACCA GGGGGCCAGG
2101  GTCCTTGACC CCACTTCCGG GTTTCATGTG AACCCCGTGG TGGTGTTCGA
2151  CTTTGCCAGC CTGTACCCCA GCATCATCCA GGCCCACAAC CTGTGCTTCA
2201  GCACGCTCTC CCTGAGGGCC GACGCAGTGG CGCACCTGGA GGCGGGCAAG
2251  GACTACCTGG AGATCGAGGT GGGGGGGCGA CGGCTGTTCT TCGTCAAGGC
2301  TCACGTGCGA GAGAGCCTCC TCAGCATCCT CCTGCGGGAC TGGCTCGCCA
2351  TGCGAAAGCA GATCCGCTCG CGGATTCCCC AGAGCAGCCC CGAGGAGGCC
2401  GTGCTCCTGG ACAAGCAGCA GGCCGCCATC AAGGTCGTGT GTAACTCGGT
2451  TTACGGGTTC ACGGGAGCGC AGCACGGACT CCTGCCGTGC CTGCACGTTG
2501  CCGCGACGGT GACGACCATC GGCCGCGAGA TGCTGCTCGC GACCCGCGAG
2551  TACGTCCACG CGCGCTGGGC GGCCTTCGAA CAGCTCCTGG CCGATTTCCC
2601  GGAGGCGGCC GACATGCGCG CCCCGGGCC CTATTCCATG CGCATCATCT
```

Figure 5O DNA and amino acid sequence list

```
2651  ACGGGGACAC GGACTCCATC TTTGTGCTGT GCCGCGGCCT CACGGCCGCC
2701  GGGCTGACGG CCGTGGGCGA CAAGATGGCG AGCCACATCT CGCGCGCGCT
2751  GTTTCTGTCC CCCATCAAAC TCGAGTGCGA AAAGACGTTC ACCAAGCTGC
2801  TGCTGATCGC CAAGAAAAAG TACATCGGCG TCATCTACGG GGGTAAGATG
2851  CTCATCAAGG GCGTGGATCT GGTGCGCAAA AACAACTGCG CGTTTATCAA
2901  CCGCACCTCC AGGGCCCTGG TCGACCTGCT GTTTTACGAC GATACCGTAT
2951  CCGGAGCGGC CGCCGCGTTA GCCGAGCGCC CCGCAGAGGA GTGGCTGGCG
3001  CGACCCCTGC CCGAGGGACT GCAGGCGTTC GGGGCCGTCC TCGTAGACGC
3051  CCATCGGCGC ATCACCGACC CGGAGAGGGA CATCCAGGAC TTTGTCCTCA
3101  CCGCCGAACT GAGCAGACAC CCGCGCGCGT ACACCAACAA GCGCCTGGCC
3151  CACCTGACGG TGTATTACAA GCTCATGGCC CGCCGCGCGC AGGTCCCGTC
3201  CATCAAGGAC CGGATCCCGT ACGTGATCGT GGCCCAGACC CGCGAGGTAG
3251  AGGAGACGGT CGCGCGGCTG GCCGCCCTCC GCGAGCTCGA CGCCGCCGCC
3301  CCAGGGGACG AGCCCGCCCC CCCCGCGGCC CTGCCCTCCC CGGCCAAGCG
3351  CCCCCGGGAG ACGCCGTTGC ATGCCGACCC CCCGGGAGGC GCGTCCAAGC
3401  CCCGCAAGCT GCTGGTGTCC GAGCTGGCCG AGGATCCCGC ATACGCCATT
3451  GCCCACGGCG TCGCCCTGAA CACGGACTAT TACTTCTCCC ACCTGTTGGG
3501  GGCGGCGTGC GTGACATTCA AGGCCCTGTT TGGGAATAAC GCCAAGATCA
3551  CCGAGAGTCT GTTAAAAAGG TTTATTCCCG AAGTGTGGCA CCCCCCGGAC
3601  GACGTGGCCG CGCGGCTCCG GGCCGCAGGG TTCGGGGCGG TGGGTGCCGG
3651  CGCTACGGCG GAGGAAACTC GTCGAATGTT GCATAGAGCC TTTGATACTC
3701  TAGCATGA
```

Figure 5P DNA and amino acid sequence list

SEQ.ID.NO. 8    Amino acid sequence of DNA polymerase for HSV1-F-M1

```
   1 MFSGGGGPLS PGGKSAARAA SGFFAPAGPR GAGRGPPPCL RQNFYNPYLA

51 PVGTQQKPTG PTQRHTYYSE CDEFRFIAPR VLDEDAPPEK RAGVHDGHLK

101 RAPKVYCGGD ERDVLRVGSG GFWPRRSRLW GGVDHAPAGF NPTVTVFHVY

151 DILENVEHAY GMRAAQFHAR FMDAITPTGT VITLLGLTPE GHRVAVHVYG

201 TRQYFYMNKE EVDRHLQCRA PRDLCERMAA ALRESPGASF RGISADHFEA

251 EVVERTDVYY YETRPALFYR VYVRSGRVLS YLCDNFCPAI KKYEGGVDAT

301 TRFILDNPGF VTFGWYRLKP GRNNTLAQPR APMAFGTSSD VEFNCTADNL

351 AIEGGMSDLP AYKLMCFDIE CKAGGEDELA FPVAGHPEDL VIQISCLLYD

401 LSTTALEHVL LFSLGSCDLP ESHLNELAAR GLPTPVVLEF DSEFEMLLAF

451 MTLVKQYGPE FVTGYNIINF DWPFLLAKLT DIYKVPLDGY GRMNGRGVFR

501 VWDIGQSHFQ KRSKIKVNGM VNIDMYGIIT DKIKLSSYKL NAVAEAVLKD

551 KKKDLSYRDI PAYYAAGPAQ RGVIGEYCIQ DSLLVGQLFF KFLPHLELSA

601 VARLAGINIT RTIYDGQQIR VFTCLLRLAD QKGFILPDTQ GRFRGGGGEA

651 PKRPAAARED EERPEEEGED EDEREEGGGE REPEGARETA GRHVGYQGAR

701 VLDPTSGFHV NPVVVFDFAS LYPSIIQAHN LCFSTLSLRA DAVAHLEAGK

751 DYLEIEVGGR RLFFVKAHVR ESLLSILLRD WLAMRKQIRS RIPQSSPEEA

801 VLLDKQQAAI KVVCNSVYGF TGAQHGLLPC LHVAATVTTI GREMLLATRE

851 YVHARWAAFE QLLADFPEAA DMRAPGPYSM RIIYGDTDSI FVLCRGLTAA

901 GLTAVGDKMA SHISRALFLS PIKLECEKTF TKLLLIAKKK YIGVIYGGKM

951 LIKGVDLVRK NNCAFINRTS RALVDLLFYD DTVSGAAAAL AERPAEEWLA

1001 RPLPEGLQAF GAVLVDAHRR ITDPERDIQD FVLTAELSRH PRAYTNKRLA

1051 HLTVYYKLMA RRAQVPSIKD RIPYVIVAQT REVEETVARL AALRELDAAA

1101 PGDEPAPPAA LPSPAKRPRE TPLHADPPGG ASKPRKLLVS ELAEDPAYAI

1151 AHGVALNTDY YFSHLLGAAC VTFKALFGNN AKITESLLKR FIPEVWHPPD

1201 DVAARLRAAG FGAVGAGATA EETRRMLHRA FDTLA*
```

Figure 5Q  DNA and amino acid sequence list

SEQ.ID.NO. 9    DNA sequence of HSV polymerase gene for HSV1-DJL-M1

```
   1 ATGTTTTCCG GTGGCGGCGG CCCGCTGTCC CCCGGAGGAA AGTCGGCGGC
  51 CAGGGCGGCG TCCGGGTTTT TTGCGCCCGC CGGCCCTCGC GGAGCCGGCC
 101 GGGGACCCCC GCCTTGTTTG AGGCAAAACT TTTACAACCC CTACCTCGCC
 151 CCAGTCGGGA CGCAACAGAA GCCGACCGGG CCAACCCAGC GCCATACGTA
 201 CTATAGCGAA TGCGATGAAT TCGATTCAT CGCCCCGCGG GTGCTGGACG
 251 AGGATGCCCC CCCGGAGAAG CGCGCCGGGG TGCACGACGG TCACCTCAAG
 301 CGCGCCCCCA AGGTGTACTG CGGGGGGGAC GAGCGCGACG TCCTCCGCGT
 351 CGGGTCGGGC GGCTTCTGGC CGCGGCGCTC GCGCCTGTGG GGCGGCGTGG
 401 ACCACGCCCC GGCGGGGTTC AACCCCACCG TCACCGTCTT TCACGTGTAT
 451 GACATCCTGG AGAACGTGGA GCACGCGTAC GGCATGCGCG CGGCCCAGTT
 501 CCACGCGCGG TTTATGGACG CCATCACACC GACGGGGACC GTCATCACGC
 551 TCCTGGGCCT GACTCCGGAA GGCCACCGGG TGGCCGTTCA CGTTTACGGC
 601 ACGCGGCAGT ACTTTTACAT GAACAAGGAG GAGGTTGACA GGCACCTACA
 651 ATGCCGCGCC CCACGAGATC TCTGCGAGCG CATGGCCGCG GCCCTGCGCG
 701 AGTCCCCGGG CGCGTCGTTC CGCGGCATCT CCGCGGACCA CTTCGAGGCG
 751 GAGGTGGTGG AGCGCACCGA CGTGTACTAC TACGAGACGC GCCCCGCTCT
 801 GTTTTACCGC GTCTACGTCC GAAGCGGGCG CGTGCTGTCG TACCTGTGCG
 851 ACAACTTCTG CCCGGCCATC AAGAAGTACG AGGGTGGGGT CGACGCCACC
 901 ACCCGGTTCA TCCTGGACAA CCCCGGGTTC GTCACCTTCG GCTGGTACCG
 951 TCTCAAACCG GGCCGGAACA ACACGCTAGC CCAGCCGCGG GCCCCGATGG
1001 CCTTCGGGAC ATCCAGCGAT GTCGAGTTTA ACTGTACGGC GGACAACCTG
1051 GCCATCGAGG GGGGCATGAG CGACCTACCG GCATACAAGC TCATGTGCTT
1101 CGATATCGAA TGCAAGGCGG GGGGGGAGGA CGAGCTGGCC TTTCCGGTGG
1151 CCGGGCACCC GGAGGACCTG GTCATCCAGA TATCCTGTCT GCTCTACGAC
1201 CTGTCCACCA CCGCCCTGGA GCACGTCCTC CTGTTTTCGC TCGGTTCCTG
1251 CGACCTCCCC GAATCCCACC TGAACGAGCT GGCGGCCAGG GGCCTGCCCA
```

Figure 5R    DNA and amino acid sequence list

1301 CGCCCGTGGT TCTGGAATTC GACAGCGAAT TCGAGATGCT GTTGGCCTTC

1351 ATGACCCTTG TGAAACAGTA CGGCCCCGAG TTCGTGACCG GGTACAACAT

1401 AATCAACTTC GACTGGCCCT TCTTGCTGGC CAAGCTGACG GACATTTACA

1451 AGGTCCCCCT GGACGGGTAC GGCCGCATGA ACGGCCGGGG CGTGTTTCGC

1501 GTGTGGGACA TAGGCCAGAG CCACTTCCAG AAGCGCAGCA AGATAAAGGT

1551 GAACGGCATG GTGAACATCG ACATGTACGG GATTATAACC GACAAGATCA

1601 AGCTCTCGAG CTACAAGCTC AACGCCGTGG CCGAAGCCGT CCTGAAGGAC

1651 AAGAAGAAGG ACCTGAGCTA TCGCGACATC CCCACCTACT ACGCCGCCGG

1701 GCCCGCGCAA CGCGGGGTGA TCGGCGAGTA CTGCATACAG GATTCCCTGC

1751 TGGTGGGCCA GCTGTTTTTT AAGTTTTGC CCCATCTGGA GCTCTCGGCC

1801 GTCGCGCGCT GGCGGGTAT TAACATCACC CGCACCATCT ACGACGGCCA

1851 GCAGATCCGC GTCTTTACGT GCCTGCTGCG CCTGGCCGAC CAGAAGGGCT

1901 TTATTCTGCC GGACACCCAG GGGCGATTTA GGGGCGCCGG GGGGGAGGCG

1951 CCCAAGCGTC CGGCCGCAGC CCGGGAGGAC GAGGAGCGGC CAGAGGAGGA

2001 GGGGGAGGAC GAGAACGAAC GCGAGGAGGG CGGGGGCGAG CGGGAGCCGG

2051 AGGGCGCGCG GGAGACCGCC GGCCGGCACG TGGGGTACCA GGGGGCCAGG

2101 GTCCTTGACC CCACTTCCGG GTTTCACGTG AACCCCGTGG TGGTGTTCGA

2151 CTTTGCCAGC CTGTACCCCA GCATCATCCA GGCCCACAAC CTGTGCTTCA

2201 GCACGCTCTC CCTGAGGGCC GACGCAGTGG CGCACCTGGA GGCGGGCAAG

2251 GACTACCTGG AGATCGAGGT GGGGGGGCGA CGGCTGTTCT TCGTCAAGGC

2301 TCACGTGCGA GAGAGCCTCC TCAGCATCCT CCTGCGGGAC TGGCTCGCCA

2351 TGCGAAAGCA GATCCGCTCG CGGATTCCCC AGAGCAGCCC CGAGGAGGCC

2401 GTGCTCCTGG ACAAGCAGCA GGCCGCCATC AAGGTCGTGT GTAACTCGGT

2451 TTACGGGTTC ACGGGAGCGC AGCACGGACT CCTGCCGTGC CTGCACGTTG

2501 CCGCGACGGT GACGACCATC GGCCGCGAGA TGCTGCTCGC GACCCGCGAG

2551 TACGTCCACG CGCGCTGGGC GGCCTTCGAA CAGCTCCTGG CCGATTTCCC

Figure 5S DNA and amino acid sequence list

```
2601 GGAGGCGGCC GACATGCGCG CCCCCGGGCC CTATTCCATG CGCATCATCT
2651 ACGGGGACAC GGACTCCATA TTTGTGCTGT GCCGCGGCCT CACGGCCGCC
2701 GGGCTGACGG CCGTGGGCGA CAAGATGGCG AGCCACATCT CGCGCGCGCT
2751 GTTTCTGCCC CCCATCAAAC TCGAGTGCGA AAAGACGTTC ACCAAGCTGC
2801 TGCTGATCGC CAAGAAAAAG TACATCGGCG TCATCTACGG GGGTAAGATG
2851 CTCATCAAGG GCGTGGATCT GGTGCGCAAA AACAACTGCG CGTTTATCAA
2901 CCGCACCTCC AGGGCCCTGG TCGACCTGCT GTTTTACGAC GATACCGTAT
2951 CCGGAGCGGC CGCCGCGTTA GCCGAGCGCC CCGCAGAGGA GTGGCTGGCG
3001 CGACCCCTGC CCGAGGGACT GCAGGCGTTC GGGGCCGTCC TCGTAGACGC
3051 CCATCGGCGC ATCACCGACC CGGAGAGGGA CATCCAGGAC TTTGTTCTCA
3101 CCGCCGAACT GAGCAGACAC CCGCGCGCGT ACACCAACAA GCGCCTGGCC
3151 CACCTGACGG TGTATTACAA GCTCATGGCC CGCCGCGCGC AGGTCCCGTC
3201 CATCAAGGAC CGGATCCCGT ACGTGATCGT GGCCCAGACC CGCGAGGTAG
3251 AGGAGACGGT CGCGCGGCTG GCCGCCCTCC GCGAGCTAGA CGCCGCCGCC
3301 CCAGGGGACG AGCCCGCCCC CCCCGCGGCC CTGCCCTCCC CGGCCAAGCG
3351 CCCCCGGGAG ACGCCGTCGC CTGCCGACCC CCCGGGAGGC GCGTCCAAGC
3401 CCCGCAAGCT GCTGGTGTCC GAGCTGGCCG AGGATCCCGC ATACGCCATT
3451 GCCCACGGCG TCGCCCTGAA CACGGACTAT TACTTCTCCC ACCTGTTGGG
3501 GGCGGCGTGC GTGACATTCA AGGCCCTGTT TGGGAATAAC GCCAAGATCA
3551 CCGAGAGTCT GTTAAAAAGG TTTATTCCCG AAGTGTGGCA CCCCCCGGAC
3601 GACGTGGCCG CGCGGCTCCG GACCGCAGGG TTCGGGGCGG TGGGTGCCGG
3651 CGCTACGGCG GAGGAAACTC GTCGAATGTT GCATAGAGCC TTTGATACTC
3701 TAGCATGA
```

Figure 5T   DNA and amino acid sequence list

SEQ.ID.NO. 10   Amino acid sequence of DNA polymerase for HSV1-DJL-M1

```
   1 MFSGGGGPLS PGGKSAARAA SGFFAPAGPR GAGRGPPPCL RQNFYNPYLA
  51 PVGTQQKPTG PTQRHTYYSE CDEFRFIAPR VLDEDAPPEK RAGVHDGHLK
 101 RAPKVYCGGD ERDVLRVGSG GFWPRRSRLW GGVDHAPAGF NPTVTVFHVY
 151 DILENVEHAY GMRAAQPHAR FMDAITPTGT VITLLGLTPE GHRVAVHVYG
 201 TRQYFYMNKE EVDRHLQCRA PRDLCERMAA ALRESPGASF RGISADHFEA
 251 EVVERTDVYY YETRPALFYR VYVRSGRVLS YLCDNFCPAI KKYEGGVDAT
 301 TRFILDNPGF VTFGWYRLKP GRNNTLAQPR APMAFGTSSD VEFNCTADNL
 351 AIEGGMSDLP AYKLMCFDIE CKAGGEDELA FPVAGHPEDL VIQISCLLYD
 401 LSTTALEHVL LFSLGSCDLP ESHLNELAAR GLPTPVVLEF DSEFEMLLAF
 451 MTLVKQYGPE FVTGYNIINF DWPFLLAKLT DIYKVPLDGY GRMNGRGVFR
 501 VWDIGQSHFQ KRSKIKVNGM VNIDMYGIIT DKIKLSSYKL NAVAEAVLKD
 551 KKKDLSYRDI PTYYAAGPAQ RGVIGEYCIQ DSLLVGQLFF KFLPHLELSA
 601 VARLAGINIT RTIYDGQQIR VFTCLLRLAD QKGFILPDTQ GRFRGAGGEA
 651 PKRPAAARED EERPEEEGED ENEREEGGGE REPEGARETA GRHVGYQGAR
 701 VLDPTSGFHV NPVVVFDFAS LYPSIIQAHN LCFSTLSLRA DAVAHLEAGK
 751 DYLEIEVGGR RLFFVKAHVR ESLLSILLRD WLAMRKQIRS RIPQSSPEEA
 801 VLLDKQQAAI KVVCNSVYGF TGAQHGLLPC LHVAATVTTI GREMLLATRE
 851 YVHARWAAFE QLLADPPEAA DMRAPGPYSM RIIYGDTDSI FVLCRGLTAA
 901 GLTAVGDKMA SHISRALFLP PIKLECEKTF TKLLLIAKKK YIGVIYGGKM
 951 LIKGVDLVRK NNCAFINRTS RALVDLLFYD DTVSGAAAAL AERPAEEWLA
1001 RPLPEGLQAF GAVLVDAHRR ITDPERDIQD FVLTAELSRH PRAYTNKRLA
1051 HLTVYYKLMA RRAQVPSIKD RIPYVIVAQT REVEETVARL AALRELDAAA
1101 PGDEPAPPAA LPSPAKRPRE TPSPADPPGG ASKPRKLLVS ELAEDPAYAI
1151 AHGVALNTDY YFSHLLGAAC VTFKALFGNN AKITESLLKR FIPEVWHPPD
1201 DVAARLRTAG FGAVGAGATA EETRRMLHRA FDTLA*
```

Figure 5U  DNA and amino acid sequence list

SEQ.ID.NO. 11  DNA sequence of DNA polymerase gene for HMCV-AD169-M1

```
   1 ATGTTTTTCA ACCCGTATCT GAGCGGCGGC GTGACCGGCG GTGCGGTCGC
  51 GGGTGGCCGG CGTCAGCGTT CGCAGCCCGG CTCCGCGCAG GGCTCGGGCA
 101 AGCGGCCGCC ACAGAAACAG TTTTTGCAGA TCGTGCCGCG AGGTGTCATG
 151 TTCGACGGTC AGACGGGGTT GATCAAGCAT AAGACGGGAC GGCTGCCTCT
 201 CATGTTCTAT CGAGAGATTA AACATTTGTT GAGTCATGAC ATGGTTTGGC
 251 CGTGTCCTTG GCGCGAGACC CTGGTGGGTC GCGTGGTGGG ACCTATTCGT
 301 TTTCACACCT ACGATCAGAC GGACGCCGTG CTCTTCTTCG ACTCGCCCGA
 351 AAACGTGTCG CCGCGCTATC GTCAGCATCT GGTGCCTTCG GGGAACGTGT
 401 TGCGTTTCTT CGGGGCCACA GAACACGGCT ACAGTATCTG CGTCAACGTT
 451 TTCGGGCAGC GCAGCTACTT TTACTGTGAG TACAGCGACA CCGATAGGCT
 501 GCGTGAGGTC ATTGCCAGCG TGGGCGAACT AGTGCCCGAA CCGCGGACGC
 551 CATACGCCGT GTCTGTCACG CCGGCCACCA AGACCTCCAT CTATGGGTAC
 601 GGGACGCGAC CCGTGCCCGA TTTGCAGTGT GTGTCTATCA GCAACTGGAC
 651 CATGGCCAGA AAAATCGGCG AGTATCTGCT GGAGCAGGGT TTTCCCGTGT
 701 ACGAGGTCCG TGTGGATCCG CTGACGCGTT TGGTCATCGA TCGGCGGATC
 751 ACCACGTTCG GCTGGTGCTC CGTGAATCGT TACGACTGGC GGCAGCAGGG
 801 TCGCGCGTCG ACTTGTGATA TCGAGGTAGA CTGCGATGTC TCTGACCTGG
 851 TGGCTGTGCC CGACGACAGC TCGTGGCCGC GCTATCGATG CCTGTCCTTC
 901 GATATCGAGT GCATGAGCGG CGAGGGTGGT TTTCCCTGCG CCGAGAAGTC
 951 CGATGACATT GTCATTCAGA TCTCGTGCGT GTGCTACGAG ACGGGGGGAA
1001 ACACCGCCGT GGATCAGGGG ATCCCAAACG GAACGATGG TCGGGGCTGC
1051 ACTTCGGAGG GTGTGATCTT TGGGCACTCG GGTCTTCATC TCTTTACGAT
1101 CGGCACCTGC GGGCAGGTGG CCCAGACGT GGACGTCTAC GAGTTCCCTT
1151 CCGAATACGA GCTGCTGCTG GGCTTTATGC TTTTCTTTCA ACGGTACGCG
1201 CCGGCCTTTG TGACCGGTTA CAACATCAAC TCTTTTGACT TGAAGTACAT
```

Figure 5V   DNA and amino acid sequence list

```
1251 CCTCACGCGT CTCGAGTACC TGTATAAGGT GGACTCGCAG CGCTTCTGCA
1301 AGTTGCCTAC GGCGCAGGGC GGCCGTTTCT TTTTACACAG CCCCGCCGTG
1351 GGTTTTAAGC GGCAGTACGC CGCCGCTTTT CCCTCGGCTT CTCACAACAA
1401 TCCGGCCAGC ACGGCCGCCA CCAAGGTGTA TATTGCGGGT TCGGTGGTTA
1451 TCGACATGTA CCCTGTATGC ATGGCCAAGA CTAACTCGCC CAACTATAAG
1501 CTCAACACTA TGGCCGAGCT TTACCTGCGG CAACGCAAGG ATGACCTGTC
1551 TTACAAGGAC ATCCCGCGTT GTTTCGTGGC TAATGCCGAG GGCCGCGCCC
1601 AGGTAGGCCG TTACTGTCTG CAGGACGCCG TATTGGTGCG CGATCTGTTC
1651 AACACCATTA ATTTTCACTA CGAGGCCGGG GCCATCGCGC GGCTGGCTAA
1701 AATTCCGTTG CGGCGTGTCA TCTTTGACGG ACAGCAGATC CGTATCTACA
1751 CCTCGCTGCT GGACGAGTGC GCCTGCCGCG ATTTTATCCT GCCCAACCAC
1801 TACAGCAAAG GTACGACGGT GCCCGAAACG AATAGCGTTG CTGTGTCACC
1851 TAACGCTGCT ATCATCTCTA CCGCCGCTGT GCCCGGCGAC GCGGGTTCTG
1901 TGGCGGCTAT GTTTCAGATG TCGCCGCCCT TGCAATCTGC GCCGTCCAGT
1951 CAGGACGGCG TTTCACCCGG CTCCGGCAGT AACAGTAGTA GCAGCGTCGG
2001 CGTTTTCAGC GTCGGCTCCG GCAGTAGTGG CGGCGTCGGC GTTTCCAACG
2051 ACAATCACGG CGCCGGCGGT ACTGCGGCGG TTTCGTACCA GGGCGCCACG
2101 GTGTTTGAGC CCGAGGTGGG TTACTACAAC GACCCCGTGG CCGTGTTCGA
2151 CTTTGCCAGC CTCTACCCTT CCATCATCAT GGCCCACAAC CTCTGCTACT
2201 CCACCCTGCT GGTGCCGGGT GGCGAGTACC CTGTGGACCC CGCCGACGTA
2251 TACAGCGTCA CGCTAGAGAA CGGCGTGACC CACCGCTTTG TGCGTGCTTC
2301 GGTGCGCGTC TCGGTGCTCT CGGAACTGCT CAACAAGTGG GTTTCGCAGC
2351 GGCGTGCCGT GCGCGAATGC ATGCGCGAGT GTCAAGACCC TGTGCGCCGT
2401 ATGCTGCTCG ACAAGGAACA GATGGCGCTC AAAGTAACGT GCAACGCTTT
2451 CTACGGTTTT ACCGGCGCGC TGAACGGTAT GATGCCGTGT CTGCCCATCG
2501 CCGCCAGCAT CACGCGCATC GGTCGCGACA TGCTAGAGCG CACGGCGCGG
```

Figure 5W   DNA and amino acid sequence list

```
2551 TTCATCAAAG ACAACTTTTC AGAGCCGTGT TTTTTGCACA ATTTTTTTAA
2601 TCAGGAAGAC TATGTAGTGG GAACGCGGGA GGGGGATTCG GAGGAGAGCA
2651 GCGCGTTACC GGAGGGGCTC GAAACATCGT CAGGGGGCTC GAACGAACGG
2701 CGGGTGGAGG CGCGGGTCAT CTACGGGGAC ACGGACAGCG TGTTTGTCCG
2751 CTTTCGTGGC CTGACGCCGC AGGCTCTGGT GGCGCGTGGG CCCAGCCTGG
2801 CGCACTACGT GACGGCCTGT CTTTTTGTGG AGCCCGTCAA GCTGGAGTTT
2851 GAAAAGGTCT TCGTCTCTCT TATGATGATC TGCAAGAAAC GTTACATCGG
2901 CAAAGTGGAG GGCGCCTCGG GTCTGAGCAT GAAGGGCGTG GATCTGGTGC
2951 GCAAGACGGC CTGCGAGTTC GTCAAGGGCG TCACGCGTGA CGTCCTCTCG
3001 CTGCTCTTTG AGGATCGCGA GGTCTCGGAA GCAGCCGTGC GCCTGTCGCG
3051 CCTCTCACTC GATGAAGTCA AGAAGTACGG CGTGCCACGC GGTTTCTGGC
3101 GTATCTTACG CCGCTTGGTG CAGGCCCGCG ACGATCTGTA CCTGCACCGT
3151 GTGCGTGTCG AGGACCTGGT GCTTTCGTCG GTGCTCTCTA AGGACATCTC
3201 GCTGTACCGT CAATCTAACC TGCCGCACAT TGCCGTCATT AAGCGATTGG
3251 CGGCCCGTTC TGAGGAGCTA CCCTCGGTCG GGATCGGGT CTTTTACGTT
3301 CTGACGGCGC CCGGTGTCCG GACGGCGCCG CAGGGTTCCT CCGACAACGG
3351 TGATTCTGTA ACCGCCGGCG TGGTTTCCCG GTCGGACGCG ATTGATGGCA
3401 CGGACGACGA CGCTGACGGC GGCGGGGTAG AGGAGAGCAA CAGGAGAGGA
3451 GGAGAGCCGG CAAAGAAGAG GGCGCGGAAA CCACCGTCGG CCGTGTGCAA
3501 CTACGAGGTA GCCGAAGATC CGAGCTACGT GCGCGAGCAC GGCGTGCCCA
3551 TTCACGCCGA CAAGTACTTT GAGCAGGTTC TCAAGGCTGT AACTAACGTG
3601 CTGTCGCCCG TCTTTCCCGG CGGCGAAACC GCGCGCAAGG ACAAGTTTTT
3651 GCACATGGTG CTGCCGCGGC GCTTGCACTT GGAGCCGGCT TTTCTGCCGT
3701 ACAGTGTCAA GGCGCACGAA TGCTGTTGA
```

Figure 5X  DNA and amino acid sequence list

SEQ.ID.NO.12  Amino acid sequence of DNA polymerase for HCMV-AD169-M1

```
   1 MFFNPYLSGG VTGGAVAGGR RQRSQPGSAQ GSGKRPPQKQ FLQIVPRGVM
  51 FDGQTGLIKH KTGRLPLMFY REIKHLLSHD MVWPCPWRET LVGRVVGPIR
 101 FHTYDQTDAV LFFDSPENVS PRYRQHLVPS GNVLRFFGAT EHGYSICVNV
 151 FGQRSYFYCE YSDTDRLREV IASVGELVPE PRTPYAVSVT PATKTSIYGY
 201 GTRPVPDLQC VSISNWTMAR KIGEYLLEQG FPVYEVRVDP LTRLVIDRRI
 251 TTFGWCSVNR YDWRQQGRAS TCDIEVDCDV SDLVAVPDDS SWPRYRCLSF
 301 DIECMSGEGG FPCAEKSDDI VIQISCVCYE TGGNTAVDQG IPNGNDGRGC
 351 TSEGVIFGHS GLHLFTIGTC GQVGPDVDVY EFPSEYELLL GFMLFFQRYA
 401 PAFVTGYNIN SFDLKYILTR LEYLYKVDSQ RFCKLPTAQG GRFFLHSPAV
 451 GFKRQYAAAF PSASHNNPAS TAATKVYIAG SVVIDMYPVC MAKTNSPNYK
 501 LNTMAELYLR QRKDDLSYKD IPRCFVANAE GRAQVGRYCL QDAVLVRDLF
 551 NTINFHYEAG AIARLAKIPL RRVIFDGQQI RIYTSLLDEC ACRDFILPNH
 601 YSKGTTVPET NSVAVSPNAA IISTAAVPGD AGSVAAMFQM SPPLQSAPSS
 651 QDGVSPGSGS NSSSSVGVFS VGSGSSGGVG VSNDNHGAGG TAAVSYQGAT
 701 VFEPEVGYYN DPVAVFDFAS LYPSIIMAHN LCYSTLLVPG GEYPVDPADV
 751 YSVTLENGVT HRFVRASVRV SVLSELLNKW VSQRRAVREC MRECQDPVRR
 801 MLLDKEQMAL KVTCNAFYGF TGALNGMMPC LPIAASITRI GRDMLERTAR
 851 FIKDNFSEPC FLHNFFNQED YVVGTREGDS EESSALPEGL ETSSGGSNER
 901 RVEARVIYGD TDSVFVRFRG LTPQALVARG PSLAHYVTAC LFVEPVKLEF
 951 EKVFVSLMMI CKKRYIGKVE GASGLSMKGV DLVRKTACEF VKGVTRDVLS
1001 LLFEDREVSE AAVRLSRLSL DEVKKYGVPR GFWRILRRLV QARDDLYLHR
1051 VRVEDLVLSS VLSKDISLYR QSNLPHIAVI KRLAARSEEL PSVGDRVFYV
1101 LTAPGVRTAP QGSSDNGDSV TAGVVSRSDA IDGTDDDADG GGVEESNRRG
1151 GEPAKKRARK PPSAVCNYEV AEDPSYVREH GVPIHADKYF EQVLKAVTNV
1201 LSPVFPGGET ARKDKFLHMV LPRRLHLEPA FLPYSVKAHE CC*
```

Figure 6

SEQ.ID.NO.13   Amino acid sequence of DNA polymerase for HCMV-AD169

```
  1  MFFNP.YLSGG VTGGAVAGGR RQRSQPGSAQ GSGKRPPQKQ FLQIVPRGVM
 51  FDGQTGLIKH KTGRLPLMFY REIKHLLSHD MVWPCPWRET LVGRVVGPIR
101  FHTYDQTDAV LFFDSPENVS PRYRQHLVPS GNVLRFFGAT EHGYSICVNV
151  FGQRSYFYCE YSDTDRLREV IASVGELVPE PRTPYAVSVT PATKTSIYGY
201  GTRPVPDLQC VSISNWTMAR KIGEYLLEQG FPVYEVRVDP LTRLVIDRRI
251  TTFGWCSVNR YDWRQQGRAS TCDIEVDCDV SDLVAVPDDS SWPRYRCLSF
301  DIECMSGEGG FPCAEKSDDI VIQISCVCYE TGGNTAVDQG IPNGNDGRGC
351  TSEGVIFGHS GLHLFTIGTC GQVGPDVDVY EFPSEYELLL GFMLFFQRYA
401  PAFVTGYNIN SFDLKYILTR LEYLYKVDSQ RFCKLPTAQG GRFFLHSPAV
451  GFKRQYAAAF PSASHNNPAS TAATKVYIAG SVVIDMYPVC MAKTNSPNYK
501  LNTMAELYLR QRKDDLSYKD IPRCFVANAE GRAQVGRYCL QDAVLVRDLF
551  NTINFHYEAG AIARLAKIPL RRVIFDGQQI RIYTSLLDEC ACRDFILPNH
601  YSKGTTVPET NSVAVSPNAA IISTAAVPGD AGSVAAMFQM SPPLQSAPSS
651  QDGVSPGSGS NSSSSVGVFS VGSGSSGGVG VSNDNHGAGG TAAVSYQGAT
701  VFEPEVGYYN DPVAVFDFAS LYPSIIMAHN LCYSTLLVPG GEYPVDPADV
751  YSVTLENGVT HRFVRASVRV SVLSELLNKW VSQRRAVREC MRECQDPVRR
801  MLLDKEQMAL KVTCNAFYGF TGVVNGMMPC LPIAASITRI GRDMLERTAR
851  FIKDNFSEPC FLHNFFNQED YVVGTREGDS EESSALPEGL ETSSGGSNER
901  RVEARVIYGD TDSVFVRFRG LTPQALVARG PSLAHYVTAC LFVEPVKLEF
951  EKVFVSLMMI CKKRYIGKVE GASGLSMKGV DLVRKTACEF VKGVTRDVLS
1001 LLFEDREVSE AAVRLSRLSL DEVKKYGVPR GFWRILRRLV QARDDLYLHR
1051 VRVEDLVLSS VLSKDISLYR QSNLPHIAVI KRLAARSEEL PSVGDRVFYV
1101 LTAPGVRTAP QGSSDNGDSV TAGVVSRSDA IDGTDDDADG GGVEESNRRG
1151 GEPAKKRARK PPSAVCNYEV AEDPSYVREH GVPIHADKYF EQVLKAVTNV
1201 LSPVFPGGET ARKDKFLHMV LPRRLHLEPA FLPYSVKAHE CC*
```

METHOD FOR TREATING HERPES VIRUSES

CROSS REFERENCE

This application claims the benefit of the following provisional applications: U.S. Ser. No: 60/218,118, filed Jul. 13, 2000; Ser. No: 60/283,880, filed Apr. 13, 2001 under 35 USC 119(e)(i).

FIELD OF THE INVENTION

The present invention relates to a method for selecting an anti-herpes viral compound and a method for selectively inhibiting herpes viruses in a human host in need of such treatment.

BACKGROUND OF THE INVENTION

The herpesviruses comprise a large family of double stranded DNA viruses. Eight of the herpes viruses, herpes simplex virus types 1 and 2 (HSV-1 and HSV-2), varicella zoster virus (VZV), human cytomegalovirus (HCMV), Epstein-Barr virus (EBV), and human herpes viruses 6, 7, and 8 (HHV-6, HHV-7, and HHV-8), have been shown to infect humans. Several of these viruses are important human pathogens.

HSV-1 is estimated to affect 100 million people in the U.S. Primary infection of HSV-1 usually occurs between the ages of one and four. Cold sores, the visible symptom, typically appear at a later age, with 20–45% of the population over the age of fifteen affected (Whitley, Clin. Intect. Dis., 26:541–555, 1998).

Genital herpes (HSV-2) is the second most common sexually transmitted disease, with approximately 22% of the U.S population infected with this virus (Fleming 1997).

VZV is the causative agent of chicken pox upon primary infection and can recur in adults as zoster.

EBV results in approximately two million cases of infectious mononucleosis in the U.S. each year. It can also cause lymphomas in immunocompromised patients and has been associated with Burkitt's lymphoma, nasopharyngeal carcinoma, and Hodgkins disease.

Infection with HCMV often occurs during childhood and is typically asymptomatic except in immunocompriomised patients where it causes significant morbidity and mortality.

HHV-6 is the causitive agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

These viruses are capable of residing in a latent state within the host. Reactivation of latent virus results from response to environmental stimuli (ex. UV exposure, stress, etc.). Infections or recurrence can be life threatening in immunocompromised patients such as AIDS or transplant patients where HCMV can result in retinitis, pneumonia, and gastrointestinal disease.

The increased immunocompromised population has created an unmet medical need for antivirals against herpesviruses because current therapies do not have a sufficiently broad spectrum against this family of viruses and/or they have limited utility due to toxicity. The present invention provides a method for selectively inhibiting herpesviruses DNA polymerase with compounds that have broad spectrum activity. The method offers a distinct advantage in the treatment of patients in need, particularly immunocompromised patients at risk of infection or reactivation by many members of the herpesvirus family.

SUMMARY OF THE INVENTION

The present invention provides a method of selecting compounds that inhibit herpes viruses comprising:
a) measuring $IC_{50}$ of a compound of interest that inhibits a wild type herpes virus,
b) measuring $IC_{50}$ of the same compound that inhibits a binding domain mutant herpes virus which is the same strain of the wild type herpes virus,
c) comparing $IC_{50}$ of step a with $IC_{50}$ of step b; and
d) selecting the compound of interest wherein the $IC_{50}$ of step b is at least 3 times greater than the $IC_{50}$ of step a.

In above method, the order of step a and step b are interchangeable.

The present invention further provides a method of selecting compounds that inhibit herpes viruses comprising:
a) measuring $IC_{50}$ of a compound of interest that inhibits a wild type HSV-1,
b) measuring $IC_{50}$ of the same compound that inhibits a binding domain mutant HSV-1 which is the same strain of the wild type herpes virus,
c) comparing $IC_{50}$ of step a with $IC_{50}$ of step b; and
d) selecting the compound of interest wherein the $IC_{50}$ of step b is at least 3 times greater than the $IC_{50}$ of step a.

In above method, the order of step a and step b are interchangeable.

The present invention further provides a method of selecting compounds that inhibit herpes viruses comprising:
a) measuring $IC_{50}$ of a compound of interest that inhibits a wild type HSV-2,
b) measuring $IC_{50}$ of the same compound that inhibits a binding domain mutant HSV-2 which is the same strain of the wild type herpes virus,
c) comparing $IC_{50}$ of step a with $IC_{50}$ of step b; and
d) selecting the compound of interest wherein the $IC_{50}$ of step b is at least 3 times greater than the $IC_{50}$ of step a.

In above method, the order of step a and step b are interchangeable.

The present invention further provides a method of selecting compounds that inhibit herpes viruses comprising:
a) measuring $IC_{50}$ of a compound of interest that inhibits a wild type HCMV,
b) measuring $IC_{50}$ of the same compound that inhibits a binding domain mutant HCMV which is the same strain of the wild type herpes virus,
c) comparing $IC_{50}$ of step a with $IC_{50}$ of step b; and
d) selecting the compound of interest wherein the $IC_{50}$ of step b is at least 3 times greater than the $IC_{50}$ of step a.

In above method, the order of step a and step b are interchangeable.

The present invention further provides a method for selectively treating diseases caused by herpes viruses in a human host comprising administering a compound to a human in need of such treatment wherein said compound inhibits herpes viruses by interaction with the binding domain in the viral DNA polymerase.

The present invention further provides method for selectively inhibiting herpes viruses in a human host comprising administering a compound to a human in need of such treatment wherein $IC_{50}$ of the compound that inhibits a binding domain mutant herpes virus is at lease 3 times greater than $IC_{50}$ of the compound that inhibits a wild type herpes virus which is the same strain as the mutant herpes virus.

The present invention further provides a compound for treating herpesviral infections in a human host wherein $IC_{50}$ of the compound that inhibits a binding domain mutant herpes virus is at lease 5 times greater than $IC_{50}$ of the compound that inhibits a wild type herpes virus which is the same strain as the mutant herpes virus.

The present invention further provides a compound for treating herpesviral infections in a human host wherein said compound inhibits the herpesvirus by interacting with the binding domain in the viral DNA polymerase.

The present invention further provides a compound for the inhibiting of herpesvirus DNA polymerases wherein serial passage of a wild type herpes virus in the presence of said compound results in a change of the wild type HSV-1 polymerase at amino acid 823 from valine to alanine.

The present invention further provides a compound for inhibiting herpesvirus DNA polymerases wherein serial passage of a wild type herpes virus in the presence of said compound results a change of the wild type HCMV polymerase at amino acid 823 from valine to alanine and at amino acid 824 from valine to leucine.

The present invention further provides a mutant herpesvirus DNA molecule having a nucleotide sequence selected from a group consisting of SEQ.ID.NO. 1; SEQ.ID.NO. 3; SEQ.ID.NO. 5; SEQ.ID.NO. 7; SEQ.ID.NO. 9; and SEQ.ID.NO. 11.

The present invention further provides a mutant herpesvirus polymerase amino acid molecule having an amino acid sequence selected from a group consisting of SEQ.ID.NO. 2; SEQ.ID.NO. 4; SEQ.ID.NO. 6; SEQ.ID.NO. 8; SEQ.ID.NO. 10 and SEQ.ID.NO. 12.

BRIEF DESCRIPTION OF THE DRAWINGS

FIG. 1—examples of 4-oxo-DHQ and 4-oxo-DHTP compounds.

FIG. 2—Herpesvirus' polymerases amino acid conserved region.

FIG. 3—Recovered virus after serial passage of HSV-1 in presence of 20 μM of compound No. 17.

FIG. 4—Comparision of Wild HSV-1 and HSV-2 herpesvirus DNA polymerase amino acid sequences alligned by amino acid homology. (Seq. No: 14–19)

FIG. 5—Mutant Herpes Virus DNA and amino acid sequence list. (Seq. No: 1–12)

FIG. 6—Wild HCMV herpesvirus DNA polymerases amino acid sequence. (Seq. No 13)

DETAILED DESCRIPTION OF THE INVENTION

A key enzyme in the replication of all herpesviruses is the virus-coded DNA polymerase. Most of the currently available anti-herpes drugs target the viral DNA polymerase. Drugs such as Foscarnet acts by direct inhibition of the viral polymerase. These drugs are non-nucleoside inhibitors of herpesvirus DNA polymerases. Others such as the nucleoside analogs, Acyclovir, Penciclovir and Ganciclovir must first be phosphorylated to the monophosphate forms by virus encoded kinases and, further phosphorylated to triphosphate by cellular enzymes before they are active inhibitors. The triphosphate forms of these nucleoside analogs inhibit polymerases by competing with the binding of natural triphosphates and their subsequent insertion into growing DNA strands. These drugs are known as nucleoside inhibitors of herpesvirus DNA polymerases.

One of the limitations of the currently available drugs is that they are active against only a few of the eight human herpesviruses. For example, Acyclovir and Penciclovir inhibit HSV and VZV replication but have poor activity against CMV.

In order to identify antiviral compounds that would have the potential to inhibit replication of most of the human herpesviruses, compounds are in vitro screened for inhibitors of herpesvirus DNA polymerase activity. Because portions of the amino acid sequence of the polymerases are highly conserved within the herpesvirus family it is possible to discover small molecules that inhibit herpesvirus polymerases but not cellular DNA polymerases. Using this biochemical approach, several new classes of compounds such as the 4-hydroxyquinoline derivatives (4-HQ), 4-oxo-dihydroquinoline derivatives (4-oxo-DHQ) and 4-oxo-dihydrothienopyridine derivatives (4-oxo-DHTP) were discovered as potent, non-nucleoside herpesvirus DNA polymerase inhibitors. In vitro polymerase assays and/or in vivo cell culture assays have demonstrated that these compounds inhibit HSV-1, HSV-2, HCMV, VZV, EBV, and HHV-8 replication.

4-Oxo-DHQ and 4-oxo-DHTP are derivatives of formula I

I 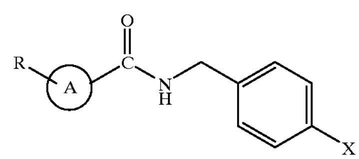 wherein ring A is a saturated or unsaturated fused double or triple heterocyclic ring having 1, 2, 3 or 4 heteroatoms selected from group consisting of oxygen, sulfur, or nitrogen; and wherein R and X are the appropriated substitutents, respectively.

Examples of 4-HQ compounds, 4-oxo-DHQ compounds and 4-oxo-DHTP compounds are illustrated in FIG. 1.

Antiviral activity of these examples are shown in Table 1 below. As shown in Table 1, these compounds inhibit HSV-1 and HSV-2 as well or better than the current commercially available drug Acyclovir.

TABLE 1

Antiviral Activity of 4-oxo DHQ/4-oxo DTHP Against HSV-1 and HSV-2

| | Compound $IC_{50}$ (uM) | | | | | |
|---|---|---|---|---|---|---|
| virus | 1 | 2 | 3 | 4 | 5 | ACV |
| HSV-1 KOS | 2.0 | 3.8 | 3.2 | 3.2 | 3.3 | 3.6 |
| HSV-1 F | 2.5 | 2.3 | 2.2 | 2.1 | 2.6 | 1.3 |
| HSV-1 DJL | 2.5 | 2.6 | 1.8 | 2.2 | 2.7 | 1.8 |
| HSV-1 Patton | ND | 5.3 | 7.7 | 4.3 | 10 | 9.3 |
| HSV-2 MS | 2.0 | 2.5 | 2.8 | 2.5 | 2.5 | 10 |
| HSV-2 35D | ND | 5.4 | 5.0 | 3.2 | 8.1 | 6.0 |
| HSV-2 186 | 2.0 | 2.3 | 3.2 | 2.3 | 4.2 | >10 |

It has also been discovered that point mutations within the HSV-1 polymerase gene that confer resistance to Acyclovir and other nucleoside analogs do not result in resistance to the 4-HQ, 4-oxo-DHQs or 4-oxo-DHTPs. Serial passage of wild type HSV-1 in the presence of 4-oxo-DHQ results in the isolation of mutants that are highly resistant (>20 fold increase in the IC$_{50}$) to these compounds while retaining sensitivity to nucleoside inhibitors such as Acyclovir.

In order to determine the mechanism of action of 4-HQ, 4-oxo-DHQ and 4-oxo-DHTP compounds against herpes viruses, mutants resistant to these compounds are isolated by serial passage of the virus in the presence of a 4-oxo-DHQ compound. Sequencing analysis of HSV-1 and HSV-2 strains resistant to the 4-oxo-DHQ identifies that HSV-1 (KOS strain) polymerase protein and its homologous HSV-2 have a conserved region (a binding domain), which is a critical contact point for these compounds. While amino acid numbering of the DNA polymerase may vary between strains of HSV-1 and HSV-2, this binding domain encompassing the HSV-1 (KOS) strain amino acid 823 is highly conserved in herpesviruses and can be identified by alligning the homologous amino acids of this domain as shown in FIG. 2.

In HSV-1 and HSV-2 strains resistant to the 4-oxo-DHQ and similar compounds, a change of valine to an alanine at the binding domain provides full resistance.

In the HSV-1 DNA polymerase, resistance is also found when a valine changes to methionine at amino acid 823 but only when accompanied by a second amino acid change.

Isolation of HCMV resistant to 4-oxo-DHQ's is found to be very difficult. Comparison of the amino acid sequence of the HSV polymerase (Y-G-F-T-G-V-Q-H-G) and HCMV polymerase (Y-G-F-T-G-V-V-N-G) in the region of amino acid 823 (underlined amino acid) shows that there is a second valine at position 824 in the HCMV polymerase. In vitro assay using mutant HCMV polymerases demonstrates that full resistance to the 4-oxo-DHQs requires changes at both amino acids 823 (a valine to alanine) and 824 (a valine to leucine). A HCMV polymerase gene containing V823A and V824L mutations is used in marker rescue experiments to generate a viral mutant. This mutant has an $IC_{50}$ approximately 7-fold above that of wild-type HCMV.

The HSV-1, HSV-2 and HCMV mutants are also found to be resistant to other non-nucleoside inhibitors such as the 4-oxo-DHTP and similar compounds. However, when the binding domain mutants (e. g. HSV-1 V823A, HSV-2-MS V826A, HSV-2–186 V828A, and HCMV V823A/V824L mutants) are tested in plaque reduction assays against a series of nucleoside polymerase inhibitors and the non-nucleoside inhibitor such as Foscarnet, replication of the mutants is found to be inhibited by all of the currently marketed anti-herpes polymerase inhibitors tested.

These studies demonstrate that certain non-nucleosides like 4-HQ, 4-oxo-DHQ and 4-oxo-DHTP compounds bind to a different site on the herpes polymerase than the nucleoside inhibitors and Foscarnet. The valine at the binding domain is conserved in the DNA polymerases of six of the eight human herpesviruses and several animal herpesviruses, and appears to play a critical role in the antiviral activity of the 4-HQ, 4-oxo-DHQ and 4-oxo-DHTP compounds. (See FIG. 2)

Since mutation at the binding domain negates these non-nucleoside inhibitors' activities, compounds could be tested against wild type polymerases and the mutant polymerases to establish the probability of similar binding. We refer to this property of compounds as interaction with the binding domain. Since compounds that interact with the binding domain have exhibited broad-spectrum activity against herpesviruses, this invention provides a method for selecting compounds to treat individuals such as immunocompromised patients who are afflicted with multple herpesvirus infections.

Definitions

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene.

In contrast, the term "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

$IC_{50}$ refers to concentration of a drug that inhibits virus growth by 50%.

Wild type HSV-1 and HSV-2 strains are listed in FIG. 4.

Wild type HCMV is listed in SEQ. ID. NO.13.

The term "Iudr" refers to antiviral drug Iododeoxyuridine.

The term "Bvdu" refers to antiviral drug Bromovinyldeoxyuridine.

The term "ACV" refers to antiviral drug Acyclovir.

The term "AraC" refers to antiviral drug Arabinosylcytidine.

The term "AraT" refers to antiviral drug Arabinosylthymine.

The term "AraA" refers to antiviral drug Arabinosyladenine.

The term "GCV" refers to antiviral drug Ganciclovir.

The term "CDV" refers to antiviral drug Cidofovir.

The term "PFA" refers to antiviral drug Foscarnet.

The term "binding domain" refers to a conserved region in herpesvirus DNA polymerases. The herpesvirus DNA polymerases have seven (7) conserved regions. The binding domain is within the thrid conserved region (see FIG. 2). When the binding domain contacts with an inhibitor, at least one amino acid in the binding domain mutates and provides the resistance. In general, the binding domain is at an amino acid sequence position 818–829 of the HSV-1 DNA polymerase or the homologous region in other herpes virus DNA polymerases (see FIG. 2).

The term "a binding domain mutant herpes virus" refers to a herpes virus containing a binding domain mutation.

More specifically, the binding domain in HSV-1 strains, KOS, F, DJL and Patton are at amino acid sequence position 823. The binding domain in HSV-2 MS-M1 strain is at amino acid sequence position 826. The binding domain in HSV-2 186 strain is at amino acid sequence position 828. The binding domain in HCMV AD 169 strains is at amino acid sequence position 823–824.

The term "XxxxY" refers to an amino acid sequence position xxx, a single amino acid X in wild type is changed to an amino acid Y.

For example, the term "V823A" refers to an amino acid sequence position 823, a Valine found in wild type is changed to alanine in mutant strain.

The term "V824L" refers to an amino acid sequence position 824, a Valine found in wild type is changed to Leucine in mutant strain.

The term "V826A" refers to an amino acid sequence position 826, a Valine found in wild type is change to alanine in mutant strain.

The term "V828A" refers to an amino acid sequence position 828, a Valine found in wild type is change to alanine in mutant strain.

A table of amino acids and their representative abbreviations, symbols and codons is set forth below in the following Table.

| Amino acid | Abbrev. | Symbol | Codon(s) |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Material and Methods

Cell and Viruses

African green monkey kidney cells (Vero) and human foreskin fibroblast cells (HFF) and herpes viruses can be obtained from the American Type Culture Collection (ATCC). Media is defined as Dulbecco's modified Eagle media (DMEM) containing 10% fetal bovine serum (FBS) and supplemented with antibiotics. Cells are maintained in media at 37° C. in a humidified atmosphere of 5% $CO^2$. HSV-1 strains F, Patton and DJL, HSV-2 strains MS, 35D and 186, and HCMV strain AD 169 are used in these studies. Strain DJL is a clinical isolate of HSV-1 isolated in our lab from a primary oral lesion.

Measuring $IC_{50}$ of a Compound of Interest That Inhibits Herpes Viruses

Preparation of Virus Stocks

HSV-1 and HSV-2 stocks are grown in Vero cells. HCMV stocks are grown in HFF cells. Approximately 1 ml of media containing sufficient virus to infect approximately 0.1% to 1% of the cells (multiplicity of infection of 0.001 to 0.01 PFU/cell) is added to a T-150 cell culture flask containing a confluent monolayer of cells. The cells are incubated at 37° C. for approximately I hour. Approximately 50 ml of media is then added to the flask and the cells are incubated at 37° C. until viral cytopathic effect (cpe) is apparent in 100% of the cells. The flask is then placed at −80° C. for at least 30 min. The flask containing frozen media and cells is placed in a 37° C. water bath until the media is thawed. This process disrupts the cells and releases virus into the media. 1 ml aliquots of media containing virus are dispensed into tubes and stored at −80° C. These aliquots of media containing virus are referred to as virus stocks.

Titrating Virus Stocks

Aliquots of virus are thawed at 37° C. and serially diluted (10 fold dilutions) in media. 0.1 ml of each dilution of virus is placed in a single well of 24-well cell culture dish containing a confluent monolayer of cells (Vero cells for HSV-1 and HSV-2, HFF cells for HCMV) and incubated at 37° C. for 1 h. The virus innoculum is then removed and 1 ml of media containing 0.8% carboxymethylcellulose (CMC) is added to each well of the dish. The dish is incubated at 37° C. for approximately 2–3 days (HSV-1 and HSV-2) or 6–9 days (HCMV) to allow sufficient growth of virus to form plaques in the cell monolayer. Plaques can be observed and counted microscopically or by staining the cells with 0.1% crystal violet in 20% ethanol. The virus titer which is expressed as plaque forming units (PFU) per ml is obtained by counting the plaques in a well and correcting for the dilution of the viral innoculum.

Plaque Reduction Assays

Antiviral activity of compounds against herpesviruses such as HSV-1, HSV-2, or HCMV can be measured using plaque reduction assays. 0.1 ml of media containing approximately 50 PFU of virus is added to each well of a 24-well cell culture dish containing a confluent monolayer of cells (Vero cells for HSV-1 and HSV-2, HFF cells for HCMV). Compounds are dissolved in 100% DMSO and diluted in 100% DMSO as 200× stocks of the desired final drug concentration. Typically 5–6 two-fold dilutions are prepared for each compound. Dilutions of compounds are then added to media containing 0.8% CMC resulting in a final 1× drug concentration. After the virus-infected cells have incubated for 1 h at 37° C., the virus innoculum is removed and 1 ml of media containing 0.8% CMC and the various concentrations of compound is added to each well of the dish. The dish is incubated at 37° C. for approximately 2–3 days (HSV-1 and HSV-2) or 6–9 days (HCMV) to allow sufficient growth of virus to form plaques in the cell monolayer. Plaques can be observed and counted microscopically or by staining the cells with 0.1% crystal violet in 20% ethanol. Virus inhibition is determined for each drug concentration by comparing the number of plaques in drug-containing wells to control wells that did not contain drug. Antiviral activity of a compound is expressed as the concentration of compound predicted to reduce the number of plaques in a well by 50% ($IC_{50}$). The $IC_{50}$ values are calculated by plotting the per cent inhibition vs. concentration of compound using EXCEL software for linear regression.

Selection of 4-oxo-DHQ Resistant HSV-1 and HSV-2

Vero cells are plated out at a density of $3.5 \times 10^5$ cells per well in a six well tissue culture plate. Cells are infected with HSV-1 KOS at a multiplicity of infection (moi) of 0.1 pfu/cell and 1 h post infection the cells are overlayed with 3 ml media containing 20 uM of a 4-oxo-DHQ. Cultures are incubated for 20 h at 37° C., freeze/thawed to release cell-associated virus, and 0.1 ml of culture is used to infect a new monolayer of Vero cells (one passage). Serial passage is repeated seven times in the presence of 20 uM drug. Virus isolates are then plaque purified three times prior to preparation of stocks. Virus recovered from each passage in the presence of compound No. 17 is shown in FIG. 3. 4-oxo-DHQ resistant HSV-1 and HSV-2 may also be selected by the marker transfer method described below using wild-type HSV DNA and the corresponding mutant HSV polymerase gene.

Marker Transfer of a HCMV Mutation

A plasmid containing the wild-type HCMV polymerase gene is modified to contain the V823A or V823A and V824L mutations using a site-directed mutagenesis Kit (Stratagene Corp.) and following the manufactures's protocol. HFF cells are plated into T25 tissue culture flasks to achieve 80% confluency at the time of the transfection. Wild type HCMV AD 169 DNA and plasmid DNA containing the mutant HCMV polymerase gene are mixed at a ratio of 1:2 (2 ug of viral DNA to 4 ug of plasmid DNA). DNA's are transfected using superfect transfection reagent according to methods recommended by the manufacturer (Quiagen Inc.). Cells are harvested five days posttransfection, freeze-thawed to release virus and half of the sample is used to infect HFF cell monolayers. Cells are overlayed with media containing 20 uM 4-oxo-DHQ compound 2 (see FIG. 1). Serial passage is repeated seven times in the presence of 20 uM compound 2 and virus isolates are then plaque purified three times prior to preparation of viral stock.

Isolation of HSV and HCMV Viral DNA

HSV DNA is purified from the cytoplasm of infected Vero cells. Vero cells (50% confluent) are infected at an multiplicity of 0.01 PFU/cell. At 3–5 days postinfection infected cells (100% cpe) are harvested by centrifugation at 1000 rpm in a Beckman GS-6R centrifuge. The pelleted cells are resuspended in TE buffer and placed on ice for 15 minutes. NP-40 is then added to a final concentration of 0.2% and incubated on ice for a further 15 minutes. The cells are centrifuged at 2000 rpm for 10 minutes in a Beckman GS-6R centrifuge. The supernatant is removed and EDTA is added to a final concentration of 20 mM followed by the addition of SDS to a final concentration of 0.3% and proteinase K to a concentration of 50 ug/ml then incubated at 45 C. for 2 hours. HCMV DNA is isolated by infecting HFF cells (25% confluency) with HCMV at an multiplicity of 0.1 PFU/cell. Cells and media are harvested 5–7 days postinfection (100% cpe) and subjected to low speed centrifugation to remove intact cells and cell debris followed by a high speed spin to pellet virus particles (2500 rpm's in a Beckman SW28 rotor for 1 hour). Following incubation of the HSV and HCMV samples, 1.5 volumes of saturated NaI is added to the digested extract and the refractive index is adjusted to 1.434–1.435. Ethidium bromide is added to a final concentration of 50 ug/ml. The samples are loaded into a VTI 50 centrifuge tube and spun for 24 hours at 45,000 rpm. The DNA band is harvested extracted three times with n-butanol, then dialyzed against TE buffer followed by a dialysis against 95% ethanol and a final dialysis against TE buffer.

DNA Sequencing

HSV-1, HSV-2 or HCMV viral DNA's are sequenced directly using an ABI377 fluorescence sequencer (Perkin Elmer Applied Biosystems, Foster City, Calif.) and the ABI BigDye PRISMTM dRhodamine Terminator Cycle Sequencing Ready Reaction Kit with AmpliTaq FSTM DNA polymerase (PE Applied Biosystems). Each cycle sequencing reaction contained about 1.0 ug of purified viral DNA. Cycle-sequencing is performed using an initial denaturation at 98° C. for 1 min, followed by 50 cycles: 98° C. for 30 sec, annealing at 50° C. for 30 sec, and extension at 60° C. for 4 min. Temperature cycles and times are controlled by a Perkin-Elmer 9700 thermocycler. Extension products are purified using CentriflexTM gel filtration cartridges (Edge BioSystems, Gaithersburg, Md.). Each reaction product is loaded by pipette onto the column, which is then centrifuged in a swinging bucket centrifuge (Sorvall model RT6000B table top centrifuge) at 750×g for 1.5 min at room temperature. Column-purified samples are dried under vacuum for about 40 min and then dissolved in 4 ul of a DNA loading solution (83% deionized formamide, 8.3 mM EDTA, and 1.6 mg/ml Blue Dextran). The samples are then heated to 90° C. for two min, and held at 4° C. until loading. 1.5 ul of each sample is loaded into a single well of the ABI377 sequencer. Sequence chromatogram data files from the ABI377 are analyzed with the computer program Sequencher (Gene Codes, Ann Arbor, Md., for assembly of sequence fragments and correction of ambiguous base calls. Generally sequence reads of 600–700 bp are obtained. Potential sequencing errors are minimized by obtaining sequence information from both DNA strands and by re-sequencing difficult areas using primers at different locations until all sequencing ambiguities are removed.

The entire coding region of the polymerase genes from both the parent strains and the resistant viruses are sequenced. The DNA sequencing is done using viral DNA as the template thus avoiding cloning of the polymerase genes. The amino acid sequence of the DNA polymerases of HSV-1 KOS, F, Patton and DJL and HSV-2 MS and 186 are compared in FIG. 4. Amino acids that are identical for the six polymerases are shaded in black while regions where amino acid differences are found are shaded in gray. The amino acid sequence of the four HSV-1 polymerases are essentially identical with only a few minor changes noted between the different HSV-1 strains. The majority of amino acid changes are found when the sequences of the HSV-1 and HSV-2 polymerases are compared.

Isolation and Characterization of HSV-1 and HSV-2 Mutants That Are Resistant To the 4-oxo-DHQ's and 4-oxo-DHTP Compounds A panel of viruses consisting of four strains of HSV-1 (KOS, F, DJL, Patton) and three strains of HSV-2 (MS, 35D, 186) are tested in a plaque reduction assay against four different 4-oxo-DHQ compounds (#1, 2, 4, 5 as shown in FIG. 1), and one 4-oxo-DHTP compound (#3 as shown in FIG. 1) and against Acyclovir. The six drugs inhibited replication of the seven virus strains with $IC_{50}$ values ranging from 2–10 μM (Table 1). In order to select for 4-oxo-DHQ resistant mutants, HSV-1 strains KOS, F, and DJL along with HSV-2 strains 186 and MS are serially passaged in the presence of 20 uM compound 1. Following the seventh passage, 4-oxo-DHQ resistant virus from each strain are plaque purified three times and high-titer stocks are made. All of the resistant HSV mutants grew to high titers in Vero cells, indicating that the mutations in the resistant isolates did not significantly impair their growth. The mutants selected with 4-oxo-DHQ compound 1 exhibited >10 fold increase in $IC_{50}$ when tested in a plaque reduction assay against 4-oxo-DHQ compound 1 Data are shown in Table 2.

TABLE 2

4-oxo-DHQ Resistant Virus of HSV-1 and HSV-2

| Virus Mutants | Compound 1 $IC_{50}$ (uM) | Amino Acid Change in HSV DNA Polymerase |
| --- | --- | --- |
| HSV-1 Kos-M1 | >20 | −V823A |
| HSV-1 F-M1 | >20 | −V823A |
| HSV-1 DJL-M1 | >20 | −V823A |
| HSV-2 MS-M1 | >20 | −V826A |
| HSV-2 186-M1 | >20 | −V828A |

*HSV-1 and HSV-2 isolates grown in the presence of 4-oxo-DHQ select for resistant virus.

DNA sequence analysis of the 4-oxo-DHQ resistant mutants (HSV-1 KOS-M1, HSV-1 F-M1, HSV-1 DJL-M1, HSV-2 186-MI, HSV-2 MS-M1) demonstrated that all five mutants contained a single point mutation of T to C at the binding domain resulting in a Valine to Alanine amino acid change.

Isolation and Characterization of a HCMV Mutant that is Resistant to The 4-oxo-DHQ's and 4-oxo-DHTP Compounds In order to select for a 4-oxo-DHQ HCMV resistant mutant, virus (strain AD169) is serially passaged in the presence of 20 uM a 4-oxo-DHQ. Although we could readily select for HSV mutants using this procedure we failed to isolate an HCMV mutant, even when the virus is passaged at low drug concentrations (<5 uM). Comparison of the amino acid sequence of the HSV polymerase, Y-G-F-T-G-V-Q-H-G, and HCMV polymerase, Y-G-F-T-G-V-V-N-G, in the region of amino acid 823 (underlined amino acid) showed that there is a second valine at position 824 in the HCMV polymerase. In order to determine if both valines need to be changed in order to confer resistance to the 4-oxo-DHQ's, in vitro polymerase assays are done using mutant HCMV polymerases containing either V823A or V823A plus V824L (Table 3).

TABLE 3

HCMV Mutant Polymerase Exhibits Resistance to 4-oxo-DHQ*

| Polymerase | Compound 1 $IC_{50}$ (uM) |
|---|---|
| HCMV (wild) | 4.6 |
| HCMV V823A | 17.2 |
| HCMV V823A/V824L | 42.9 |

*Generation of the valine to alanine at amino acid 823 of HCMV results in a 3.5-fold increase in resistance.
*Mutation of the amino acid from valine to alanine and amino acid 824 from valine to leucine results in an 9-fold increase in resistance, relative to wild type.

The V823A alone resulted in a 3.5-fold increase in the $IC_{50}$ while the polymerase with the double amino acid change had nearly 10-fold increase in the $IC_{50}$. In order to isolate an HCMV resistant mutant marker rescue experiments are done. Plasmids containing the mutant polymerase genes are transfected into HFF cells along with wild type HCMV AD169 DNA. The resulting virus is then serially passaged in the presence of 20 uM compound 1 (see FIG. 1). A 4-oxo-DHQ resistant virus is isolated from marker rescue studies done with the HCMV polymerase gene containing mutations that result in the V823A, V824L amino acid changes, but not with the gene containing V823A change alone. The mutant selected with compound 1 (HCMV AD169–M1) exhibited ~7-fold increase in $IC_{50}$ when tested in a plaque reduction assay compared to Ganciclovir and cidofovir which has a <2-fold change in sensitivity (Table 4).

TABLE 4

Plaque reduction assay of 4-oxo-DHQ resistant HCMV*

| Drug | HCMV AD169 $IC_{50}$ ($\mu$M) | HCMV AD169 - M1 $IC_{50}$ ($\mu$M) |
|---|---|---|
| Compound 1 | 0.7 | 4.7 |
| Ganciclovir | 0.9 | 1.0 |
| Cidofovir | 0.3 | 0.6 |

*Recombination of wild-type HCMV with a polymerase gene containing the valine to alanine at amino acid 823 and the valine to leucine at amino acid 824 allowed for selection of resistant virus with about 7-fold less sensitivity to compound 1.
*Sensitivity of resistant HCMV virus to Ganciclovir and Cidofovir verifies that the 4-oxo-DHQ's mechanism for inhibiting the polymerase protein is unique The entire coding region of the HCMV polymerase genes from both the parent strain and the resistant virus are sequenced. The DNA sequencing is again done using viral DNA as the template thus avoiding cloning of the polymerase genes. Comparison of the DNA sequence of the two polymerase genes demonstrated that the resistant mutant contained two point mutations that resulted in the predicted V823A, V824L amino acid changes. As with the HSV resistant viruses these results demonstrate the critical role of the region encompassing amino acid 823 for inhibition of polymerase activity by these compounds.

Antiviral Activity of Nucleoside and Non-Nucleoside Polymerase Inhibitors Against 4-oxo-DHQ Resistant Mutants In order to determine if the 4-HQ binding domain mutations alter the sensitivity of the HSV-1, HSV-2 and HCMV mutants to both non-nucleoside (4-oxo-DHQ's) and nucleoside inhibitors (e.g Acyclovir and ganciclovir) several of the mutants are tested in plaque reduction assays against a series of non-nucleoside compounds including Foscarnet (PFA), 4–HQ's 4-oxo-DHQ's and 4-oxo-DHTP's (Table 5). The mutants are also tested against a series of nucleoside inhibitors including acyclovir and ganciclovir (Table 5). The activity of these compounds against the mutants is compared to their activity against the wild type strains that are used to isolate the HSV and HCMV mutants. When tested against a number of 4–HQ's, 4-oxo-DHQ's and 4-oxo-DHTP's and other related classes of compounds all of the drugs are found to inhibit the wild type virus with $IC_{50}$ values ranging from <0.1 uM to 30 uM. When these drugs are tested against the resistant viruses they are found to have $IC_{50}$ values 5 to 10 fold higher then the parent virus. There is little if any difference in the $IC_{50}$ values of the nucleoside compounds and the non-nucleoside PFA between the wild type and mutant HSV-1, HSV-2, and HCMV viruses. These results demonstrate that the amino acid change in the binding domain (V823A in the HSV-1 polymerase, V826A in the HSV2-MS polymerase, V828A in the HSV2–186 polymerase, and the V823A/V824L changes in the HCMV polymerase) resulted in resistance to the 4-oxo-DHQ's and 4-oxo-DHTP's, which provides further evidence that these classes of compounds share an affinity for a region we refer to as the binding domain. In contrast, these amino acid changes did not alter the activity of these viruses to other classes of polymerase inhibitors.

TABLE 5

Antiviral activity of nucleoside and non-nucleoside polymerase inhibitors against HSV-1, HSV-2, and HCMV Isolates selected for 4-oxo-DHQ resistance*

Plaque Reduction Assay - $IC_{50}$ ($\mu$M)

| Drug | HSV-2 MS | HSV-2 MS-M1 | HSV-1 KOS | HSV-1 KOS-M1 | HCMV AD169 | HCMV AD169-M1 |
|---|---|---|---|---|---|---|
| 6 | 28.8 | >50 | 24.6 | >50 | 5.1 | >16 |
| 7 | 8.8 | 27.9 | 6.5 | >50 | 0.3 | 3.4 |
| 8 | 2.3 | >50 | 5.1 | >50 | <0.1 | 1.1 |
| 9 | 0.9 | 48.7 | 1.9 | >50 | <0.1 | 3.1 |
| 10 | 29.2 | >50 | 15.8 | >50 | 1.1 | >16 |
| 11 | 3.0 | >50 | 3.1 | >50 | 0.7 | 3.9 |
| 12 | 0.4 | 12.5 | 1.3 | >50 | 0.2 | 1.1 |
| 13 | 5.3 | >50 | 5.5 | <25 | 2.7 | >16 |
| 14 | 1.6 | >50 | 28.4 | >50 | 0.9 | 18.4 |
| 2 | 1.3 | >50 | 3.3 | >50 | 0.4 | 4.0 |
| 4 | 2.1 | 28.4 | 4.2 | >50 | 0.6 | 2.1 |
| 3 | 0.8 | >50 | 4.0 | >50 | 1.5 | 6.2 |
| 15 | 5.9 | >50 | >50 | >50 | 0.7 | 7.7 |
| Iudr | 5.0 | 6.1 | 1.1 | 0.8 | ND | ND |
| Bvdu | 5.8 | 5.9 | 2.1 | 0.1 | ND | ND |
| ACV | 2.4 | 2.8 | 3.9 | 4.4 | ND | ND |
| AraC | 0.2 | 0.1 | 0.2 | 0.2 | ND | ND |
| AraT | 6.6 | 3.6 | 11.6 | 3.6 | ND | ND |
| AraA | 10.6 | 18.2 | 26.1 | 27.2 | ND | ND |
| GCVir | ND | ND | ND | ND | 0.8 | 0.8 |
| CDV | ND | ND | ND | ND | 0.4 | 0.3 |
| PFA | ND | ND | ND | ND | 38 | <20 |

*HSV-2 MS, HSV-1 KOS, HCMV AD169: wild type strains
*HSV-2 MS-M1, HSV-1 KOS-M1, HCMV AD169-M1: mutants selected for 4-oxo-DHQ resistance
ND - Not Done.

Antiviral compounds identified by the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Science by E. W. Martin (Mark Publ. Co., 15th Ed., 1975).

Antiviral compounds identified by the present invention and their compositions can be administered parenterally (for example, by intravenous, intraperitoneal or intramuscular injection), topically, orally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Antiviral compounds identified by the present invention and their compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The exact regimen for administration of the compounds and compositions disclosed herein will necessarily be dependent upon the needs of the individual subject being treated, the type of treatment and, of course, the judgment of the attending practitioner.

The antiviral activity of a compound of the invention can be determined using pharmacological models which are well known to the art, or using Test A described below.

The compounds of formula (I) and pharmaceutically acceptable salts thereof are useful as antiviral agents. Thus, they are useful to combat viral infections in animals, including man. The compounds are generally active against herpes viruses, and are particularly useful against the varicella zoster virus, the Epstein-Barr virus, the herpes simplex virus, the human herpes virus type 8 (HHV-8) and the cytomegalovirus (CMV).

We claim:

1. A method of selecting a compound for inhibiting the replication of herpes viruses comprising the steps of:
   a) measuring $IC_{50}$ of a compound of interest that inhibits the replication of a wild type herpes virus;
   b) measuring $IC_{50}$ of the compound of interest that inhibits the replication of a mutant herpes virus which is the same strain as the wild type herpes virus and has a mutation in its binding domain;
   c) comparing the $IC_{50}$ of step a) with the $IC_{50}$ of step b); and
   d) selecting the compound of interest when the $IC_{50}$ of step b) is at least 3 times greater than the $IC_{50}$ of step a).

2. A method of selecting a compound for inhibiting the replication of herpes viruses comprising the steps of:

a) measuring $IC_{50}$ of a compound of interest that inhibits the replication of a mutant herpes virus which has a mutation in its binding domain;

b) measuring $IC_{50}$ of the compound of interest that inhibits the replication of a wild type herpes virus which is the same strain as the mutant herpes virus;

c) comparing the $IC_{50}$ of step a) with the $IC_{50}$ of step b); and d) selecting the compound of interest when the $IC_{50}$ of step a) is at least 3 times greater than the $IC_{50}$ of step b).

3. A method of selecting a compound that inhibits the replication of herpes viruses which comprises the steps of:

a) measuring $IC_{50}$ of a compound of interest that inhibits the replication of a wild type HSV-1;

b) measuring $IC_{50}$ of the compound of interest that inhibits the replication of a mutant HSV-1 which is the same strain as the wild type HSV-1 and has a mutation in its binding domain;

c) comparing the $IC_{50}$ of step a) with the $IC_{50}$ of step b); and d) selecting the compound of interest when the $IC_{50}$ of step b) is at least 3 times greater than the $IC_{50}$ of step a).

4. A method of selecting a compound of interest that inhibits the replication of herpes viruses which comprises the steps of:

a) measuring $IC_{50}$ of a compound of interest that inhibits the replication of a mutant HSV-1 which has a mutation in its binding domain;

b) measuring $IC_{50}$ of the compound of interest that inhibits the replication of a wild type HSV-1 which is the same strain as the mutant HSV-1;

c) comparing the $IC_{50}$ of step a) which the $IC_{50}$ of step b); and d) selecting the compound of interest when the $IC_{50}$ of step a) is at least 3 times greater than the $IC_{50}$ of step b).

5. A method of selecting a compound that inhibits the replication of herpes viruses which comprise the steps of:

a) measuring $IC_{50}$ of a compound of interest that inhibits the replication of a wild type HSV-2;

b) measuring $IC_{50}$ of the compound of interest that inhibits the replication of a mutant HSV-2 which is the same strain as the wild type HSV-2 and has a mutation in its binding domain;

c) comparing the $IC_{50}$ of step a) with the $IC_{50}$ of step b); and d) selecting the compound of interest when the $IC_{50}$ of step b) is at least three times greater than the $IC_{50}$ of step a).

6. A method of selecting a compound for inhibiting the replication of herpes viruses comprising the steps of:

a) measuring $IC_{50}$ of a compound of interest that inhibits the replication of a mutant HSV-2 which has a mutation in its binding domain;

b) measuring $IC_{50}$ of the compound of interest that inhibits the replication of a wild type HSV-2 which is the same strain as the mutant HSV-2;

c) comparing the $IC_{50}$ of step a) with the $IC_{50}$ of step b); and d) selecting the compound of interest when the $IC_{50}$ of step a) is at least 3 times greater than the $IC_{50}$ of step b).

7. A method of selecting a compound that inhibits the replication of herpes viruses which comprises the steps of:

a) measuring $IC_{50}$ of a compound of interest that inhibits the replication of a wild type HCMV;

b) measuring $IC_{50}$ of the compound of interest that inhibits the replication of a mutant HCMV which is the same strain as the wild type HCMV and ha a mutation in its binding domain;

c) comparing the $IC_{50}$ of step a) with the $IC_{50}$ of step b); and d) selecting the compound of interest when the $IC_{50}$ of step b) is at least 3 times greater than the $IC_{50}$ of step a).

8. A method of selecting a compound that inhibits the replication of herpes viruses which comprises the steps of:

a) measuring $IC_{50}$ of a compound of interest that inhibits the replication of a mutant HCMV which has a mutation in its binding domain;

b) measuring $IC_{50}$ for the compound of interest that inhibits the replication of a wild type HCMV which is the same strain as the mutant HCMV;

c) comparing the $IC_{50}$ of step a) with the $IC_{50}$ of step b); and d) selecting the compound of interest when the $IC_{50}$ step a) is at least three times greater than the $IC_{50}$ of step b).

9. The method of claim 1 or 2 wherein the herpes virus is HSV-1, HSV-2, HCMV, VZV, EBV, or HHV-8.

10. The method of claim 3 or 4 wherein HSV-1 is HSV-1 KOS, HSV-1 F, HSV-1 DJL or HSV-1 Patton.

11. The method of claim 3 or 4 wherein the mutation of a wild type herpes virus to mutant herpes virus is at amino acid 823 from valine to alanine.

12. The method of claim 5 or 6 wherein HSV-2 is HSV-2 MS, HSV-2 35D, or HSV-2 186.

13. The method of claim 7 or 8 wherein HCMV is HCMV AD169.

14. The methods of claims 1, 3, 5 or 7 wherein $IC_{50}$ of step b is at least 5 times greater than the $IC_{50}$ of step a.

15. The methods of claims 2, 4, 6 or 8 wherein $IC_{50}$ of step a is at least 5 times greater than the $IC_{50}$ of step b.

* * * * *

SEQUENCE LISTING

<160> NUMBER OF SEQ ID NOS: 19

<210> SEQ ID NO 1
<211> LENGTH: 3717
<212> TYPE: DNA
<213> ORGANISM: herpes simplex

<400> SEQUENCE: 1

```
atgttttgtg ccgcgggcgg cccgacttcc cccgggggga agtcggcggc tcgggcggcg      60
tctgggtttt ttgcccccca caaccccogg ggagccaccc agacggcacc gccgccttgc     120
cgccggcaga acttctacaa cccccacctc gctcagaccg gaacgcagcc aaaggccccc     180
gggccggctc agcgccatac gtactacagc gagtgcgacg aatttcgatt tatcgcccg      240 cgttcgctgg acgaggacgc ccccgcggag cagcgcaccg gggtccacga cggccgcctc     300
cggcgcgccc ctaaggtgta ctgcgggggg gacgagcgcg acgtcctccg cgtgggcccg     360
gagggcttct ggccgcgtcg cttgcgcctg tggggcggtg cggaccatgc ccccaagggg     420
ttcgacccca ccgtcaccgt cttccacgtg tacgacatcc tggagcacgt ggaacacgcg     480
tacagcatgc gcgccgccca gctccacgag cgatttatgg acgccatcac gcccgccggg     540
accgtcatca cgcttctggg tctgaccccc gaaggccatc gcgtcgccgt tcacgtctac     600
ggcacgcggc agtacttta catgaacaag gcggaggtgg atcggcacct gcagtgccgt     660
gccccgcgcg atctctgcga gcgcctggcg gcggccctgc gcgagtcgcc gggggcgtcg     720
ttccgcggca tctccgcgga ccacttcgag gcggaggtgg tggagcgcgc cgacgtgtac     780
tattacgaaa cgcgcccgac cctgtactac cgcgtcttcg tgcgaagcgg gcgcgcgctg     840
gcctacctgt gcgacaactt ttgccccgcg atcaggaagt acgaggggg cgtcgacgcc     900 accacccggt ttatcctgga caacccgggg tttgtcacct tcggctggta ccgcctcaag     960
cccggccgcg ggaacgcgcc ggcccaaccg cgccccccga cggcgttcgg aacctcgagc    1020
gacgtcgagt ttaactgcac ggcggacaac ctggccgtcg aggggggccat gtgtgacctg    1080 ccggcctaca agctcatgtg cttcgatatc gaatgcaagg ccgggggggga ggacgagctg    1140 gcctttccgg tcgcggaacg cccggaagac ctcgtcatcc agatctcctg tctgctctac    1200
gacctgtcca ccaccgccct cgagcacatc ctcctgtttt cgctcggatc ctgcgacctc    1260
cccgagtccc acctcagcga tctcgcctcc aggggcctgc cggcccccgt cgtcctggag    1320
tttgacagcg aattcgagat gctgctggcc ttcatgacct tcgtcaagca gtacggcccc    1380
```

-continued

```
gagttcgtga ccgggtacaa catcatcaac ttcgactggc ccttcgtcct gaccaagctg    1440
acggagatct acaaggtccc gctcgacggg tacgggcgca tgaacggccg gggtgtgttc    1500
cgcgtgtggg acatcggcca gagccacttt cagaagcgca gcaagatcaa ggtgaacggg    1560
atggtgaaca tcgacatgta cggcatcatc accgacaagg tcaaactctc cagctacaag    1620
ctgaacgccg tcgccgaggc cgtcttgaag gacaagaaga aggatctgag ctaccgcgac    1680
atccccgcct actacgcctc cgggcccgcg cagcgcgggg tgatcggcga gtattgtgtg    1740
caggactcgc tgctggtcgg gcagctgttc ttcaagtttc tgccgcacct ggagctttcc    1800
gccgtcgcgc gcctggcggg catcaacatc acccgcacca tctacgacgg ccagcagatc    1860
cgcgtcttca cgtgcctcct cgccttgcg ggccagaagg gcttcatcct gccggacacc    1920
caggggcggt tcggggcct cgacaaggag gcgcccaagc gcccggccgt gcctcggggg    1980 gaagggagc ggccggggga cgggaacggg gacgaggata aggacgacga cgaggacgag    2040
gacggggacg agcgcgagga ggtcgcgcgc gagaccgggg gccggcacgt tgggtaccag    2100
ggggcccggg tcctcgaccc cacctccggg tttcacgtcg accccgtggt ggtgtttgac    2160
tttgccagcc tgtacccag catcatccag gcccacaacc tgtgcttcag tacgctctcc    2220
ctgcggcccg aggccgtcgc gcacctggag gcggaccggg actacctgga gatcgaggtg    2280
gggggccgac ggctgttctt cgtgaaggcc cacgtacgcg agagcctgct gagcatcctg    2340
ctgcgcgact ggctggccat gcgaaagcag atccgctcgc ggatccccca gagcaccccc    2400
gaggaggccg tcctcctcga caagcaacag gccgccatca aggtggtgtg caactcggtg    2460
tacgggttca ccggggcgca gcacggtctt ctgccctgcc tgcacgtggc cgccaccgtg    2520
acgaccatcg gccgcgagat gctcctcgcg acgcgcgcgt acgtgcacgc gcgctgggcg    2580
gagttcgatc agctgctggc cgactttccg gaggcggccg gcatgcgcgc ccccggtccg    2640
tactccatgc gcatcatcta cggggacacg gactccattt tcgttttgtg ccgcggcctc    2700
acggccgcgg gcctggtggc catgggcgac aagatggcga ccacatctc gcgcgcgctg    2760 ttcctccccc cgatcaagct cgagtgcgaa aaaacgttca ccaagctgct gctcatcgcc    2820
aagaaaaagt acatcggcgt catctgcggg ggcaagatgc tcatcaaggg cgtggatctg    2880
gtgcgcaaaa acaactgcgc gtttatcaac cgcacctcca gggccctggt cgacctgctg    2940
ttttacgacg ataccgtatc cggagcggcc gccgcgttag ccgagcgccc cgcagaggag    3000
tggctggcgc gaccccctgcc cgagggactg caggcgttcg gggccgtcct cgtagacgcc    3060
catcggcgca tcaccgaccc ggagagggac atccaggact tgtcctcac cgccgaactg    3120 agcagacacc cgcgcgcgta caccaacaag cgcctggccc acctgacggt gtattacaag    3180
ctcatggccc gccgcgcgca ggtcccgtcc atcaaggacc ggatcccgta cgtgatcgtg    3240
gcccagaccc gcgaggtaga ggagacggtc gcgcggctgg ccgccctccg cgagctagac    3300
gccgccgccc caggggacga gcccgccccc ccagcggccc tgccctcccc ggccaagcgc    3360
ccccgggaga cgccgtcgca tgccgacccc cgggaggcg cgtccaagcc ccgcaagctg    3420
ctggtgtccg agctggcgga ggatcccggg tacgccatcg cccggggcgt tccgctcaac    3480
acggactatt acttctcgca cctgctgggg gcggcctgcg tgacgttcaa ggccctgttt    3540
ggaaataacg ccaagatcac cgagagtctg ttaaagaggt ttattcccga cgtgtggcac    3600 cccccgacg acgtggccgc gcggctcagg gccgcgggt tcgggccggc ggggccggc    3660 gctacggcgg aggaaactcg tcgaatgttg catagagcct ttgatactct agcatga       3717
```

```
<210> SEQ ID NO 2
<211> LENGTH: 1238
<212> TYPE: PRT
<213> ORGANISM: herpes simplex

<400> SEQUENCE: 2

Met Phe Cys Ala Ala Gly Gly Pro Thr Ser Pro Gly Gly Lys Ser Ala
1               5                   10                  15

Ala Arg Ala Ala Ser Gly Phe Phe Ala Pro His Asn Pro Arg Gly Ala
            20                  25                  30

Thr Gln Thr Ala Pro Pro Cys Arg Arg Gln Asn Phe Tyr Asn Pro
        35                  40                  45

His Leu Ala Gln Thr Gly Thr Gln Pro Lys Ala Pro Gly Pro Ala Gln
    50                  55                  60

Arg His Thr Tyr Tyr Ser Glu Cys Asp Glu Phe Arg Phe Ile Ala Pro
65                  70                  75                  80

Arg Ser Leu Asp Glu Asp Ala Pro Ala Glu Gln Arg Thr Gly Val His
                85                  90                  95

Asp Gly Arg Leu Arg Arg Ala Pro Lys Val Tyr Cys Gly Gly Asp Glu
            100                 105                 110

Arg Asp Val Leu Arg Val Gly Pro Glu Gly Phe Trp Pro Arg Arg Leu
        115                 120                 125

Arg Leu Trp Gly Gly Ala Asp His Ala Pro Lys Gly Phe Asp Pro Thr
    130                 135                 140

Val Thr Val Phe His Val Tyr Asp Ile Leu Glu His Val Glu His Ala
145                 150                 155                 160

Tyr Ser Met Arg Ala Ala Gln Leu His Glu Arg Phe Met Asp Ala Ile
                165                 170                 175

Thr Pro Ala Gly Thr Val Ile Thr Leu Leu Gly Leu Thr Pro Glu Gly
            180                 185                 190

His Arg Val Ala Val His Val Tyr Gly Thr Arg Gln Tyr Phe Tyr Met
        195                 200                 205

Asn Lys Ala Glu Val Asp Arg His Leu Gln Cys Arg Ala Pro Arg Asp
    210                 215                 220

Leu Cys Glu Arg Leu Ala Ala Ala Leu Arg Glu Ser Pro Gly Ala Ser
225                 230                 235                 240

Phe Arg Gly Ile Ser Ala Asp His Phe Glu Ala Glu Val Val Glu Arg
                245                 250                 255

Ala Asp Val Tyr Tyr Tyr Glu Thr Arg Pro Thr Leu Tyr Tyr Arg Val
            260                 265                 270

Phe Val Arg Ser Gly Arg Ala Leu Ala Tyr Leu Cys Asp Asn Phe Cys
        275                 280                 285

Pro Ala Ile Arg Lys Tyr Glu Gly Gly Val Asp Ala Thr Thr Arg Phe
    290                 295                 300

Ile Leu Asp Asn Pro Gly Phe Val Thr Phe Gly Trp Tyr Arg Leu Lys
305                 310                 315                 320

Pro Gly Arg Gly Asn Ala Pro Gln Pro Arg Pro Thr Ala Phe
                325                 330                 335

Gly Thr Ser Ser Asp Val Glu Phe Asn Cys Thr Ala Asp Asn Leu Ala
            340                 345                 350

Val Glu Gly Ala Met Cys Asp Leu Pro Ala Tyr Lys Leu Met Cys Phe
        355                 360                 365

Asp Ile Glu Cys Lys Ala Gly Gly Glu Asp Glu Leu Ala Phe Pro Val
    370                 375                 380
```

-continued

```
Ala Glu Arg Pro Glu Asp Leu Val Ile Gln Ile Ser Cys Leu Leu Tyr
385                 390                 395                 400

Asp Leu Ser Thr Thr Ala Leu Glu His Ile Leu Leu Phe Ser Leu Gly
            405                 410                 415

Ser Cys Asp Leu Pro Glu Ser His Leu Ser Asp Leu Ala Ser Arg Gly
            420                 425                 430

Leu Pro Ala Pro Val Val Leu Glu Phe Asp Ser Glu Phe Glu Met Leu
            435                 440                 445

Leu Ala Phe Met Thr Phe Val Lys Gln Tyr Gly Pro Glu Phe Val Thr
450                 455                 460

Gly Tyr Asn Ile Ile Asn Phe Asp Trp Pro Phe Val Leu Thr Lys Leu
465                 470                 475                 480

Thr Glu Ile Tyr Lys Val Pro Leu Asp Gly Tyr Gly Arg Met Asn Gly
                485                 490                 495

Arg Gly Val Phe Arg Val Trp Asp Ile Gly Gln Ser His Phe Gln Lys
            500                 505                 510

Arg Ser Lys Ile Lys Val Asn Gly Met Val Asn Ile Asp Met Tyr Gly
            515                 520                 525

Ile Ile Thr Asp Lys Val Lys Leu Ser Ser Tyr Lys Leu Asn Ala Val
530                 535                 540

Ala Glu Ala Val Leu Lys Asp Lys Lys Asp Leu Ser Tyr Arg Asp
545                 550                 555                 560

Ile Pro Ala Tyr Tyr Ala Ser Gly Pro Ala Gln Arg Gly Val Ile Gly
                565                 570                 575

Glu Tyr Cys Val Gln Asp Ser Leu Leu Val Gly Gln Leu Phe Phe Lys
            580                 585                 590

Phe Leu Pro His Leu Glu Leu Ser Ala Val Ala Arg Leu Ala Gly Ile
            595                 600                 605

Asn Ile Thr Arg Thr Ile Tyr Asp Gly Gln Gln Ile Arg Val Phe Thr
            610                 615                 620

Cys Leu Leu Arg Leu Ala Gly Gln Lys Gly Phe Ile Leu Pro Asp Thr
625                 630                 635                 640

Gln Gly Arg Phe Arg Gly Leu Asp Lys Glu Ala Pro Lys Arg Pro Ala
                645                 650                 655

Val Pro Arg Gly Glu Gly Glu Arg Pro Gly Asp Gly Asn Gly Asp Glu
            660                 665                 670

Asp Lys Asp Asp Asp Glu Asp Gly Asp Glu Arg Glu Glu Val
            675                 680                 685

Ala Arg Glu Thr Gly Gly Arg His Val Gly Tyr Gln Gly Ala Arg Val
690                 695                 700

Leu Asp Pro Thr Ser Gly Phe His Val Asp Pro Val Val Phe Asp
705                 710                 715                 720

Phe Ala Ser Leu Tyr Pro Ser Ile Ile Gln Ala His Asn Leu Cys Phe
                725                 730                 735

Ser Thr Leu Ser Leu Arg Pro Glu Ala Val Ala His Leu Glu Ala Asp
            740                 745                 750

Arg Asp Tyr Leu Glu Ile Glu Val Gly Gly Arg Arg Leu Phe Phe Val
            755                 760                 765

Lys Ala His Val Arg Glu Ser Leu Leu Ser Ile Leu Arg Asp Trp
            770                 775                 780

Leu Ala Met Arg Lys Gln Ile Arg Ser Arg Ile Pro Gln Ser Thr Pro
785                 790                 795                 800

Glu Glu Ala Val Leu Leu Asp Lys Gln Gln Ala Ala Ile Lys Val Val
```

```
                    805                 810                 815
Cys Asn Ser Val Tyr Gly Phe Thr Gly Ala Gln His Gly Leu Leu Pro
            820                 825                 830
Cys Leu His Val Ala Ala Thr Val Thr Thr Ile Gly Arg Glu Met Leu
            835                 840                 845
Leu Ala Thr Arg Ala Tyr Val His Ala Arg Trp Ala Glu Phe Asp Gln
            850                 855                 860
Leu Leu Ala Asp Phe Pro Glu Ala Ala Gly Met Arg Ala Pro Gly Pro
865                 870                 875                 880
Tyr Ser Met Arg Ile Ile Tyr Gly Asp Thr Asp Ser Ile Phe Val Leu
            885                 890                 895
Cys Arg Gly Leu Thr Ala Ala Gly Leu Val Ala Met Gly Asp Lys Met
            900                 905                 910
Ala Ser His Ile Ser Arg Ala Leu Phe Leu Pro Pro Ile Lys Leu Glu
            915                 920                 925
Cys Glu Lys Thr Phe Thr Lys Leu Leu Leu Ile Ala Lys Lys Lys Tyr
            930                 935                 940
Ile Gly Val Ile Cys Gly Gly Lys Met Leu Ile Lys Gly Val Asp Leu
945                 950                 955                 960
Val Arg Lys Asn Asn Cys Ala Phe Ile Asn Arg Thr Ser Arg Ala Leu
            965                 970                 975
Val Asp Leu Leu Phe Tyr Asp Asp Thr Val Ser Gly Ala Ala Ala Ala
            980                 985                 990
Leu Ala Glu Arg Pro Ala Glu Glu Trp Leu Ala Arg Pro Leu Pro Glu
            995                 1000                1005
Gly Leu Gln Ala Phe Gly Ala Val Leu Val Asp Ala His Arg Arg
            1010                1015                1020
Ile Thr Asp Pro Glu Arg Asp Ile Gln Asp Phe Val Leu Thr Ala
            1025                1030                1035
Glu Leu Ser Arg His Pro Arg Ala Tyr Thr Asn Lys Arg Leu Ala
            1040                1045                1050
His Leu Thr Val Tyr Tyr Lys Leu Met Ala Arg Arg Ala Gln Val
            1055                1060                1065
Pro Ser Ile Lys Asp Arg Ile Pro Tyr Val Ile Val Ala Gln Thr
            1070                1075                1080
Arg Glu Val Glu Glu Thr Val Ala Arg Leu Ala Ala Leu Arg Glu
            1085                1090                1095
Leu Asp Ala Ala Ala Pro Gly Asp Glu Pro Ala Pro Pro Ala Ala
            1100                1105                1110
Leu Pro Ser Pro Ala Lys Arg Pro Arg Glu Thr Pro Ser His Ala
            1115                1120                1125
Asp Pro Pro Gly Gly Ala Ser Lys Pro Arg Lys Leu Leu Val Ser
            1130                1135                1140
Glu Leu Ala Glu Asp Pro Gly Tyr Ala Ile Ala Arg Gly Val Pro
            1145                1150                1155
Leu Asn Thr Asp Tyr Tyr Phe Ser His Leu Leu Gly Ala Ala Cys
            1160                1165                1170
Val Thr Phe Lys Ala Leu Phe Gly Asn Asn Ala Lys Ile Thr Glu
            1175                1180                1185
Ser Leu Leu Lys Arg Phe Ile Pro Glu Thr Trp His Pro Pro Asp
            1190                1195                1200
Asp Val Ala Ala Arg Leu Arg Ala Ala Gly Phe Gly Pro Ala Gly
            1205                1210                1215
```

Ala Gly Ala Thr Ala Glu Glu  Thr Arg Arg Met Leu His Arg Ala
    1220              1225             1230

Phe Asp  Thr Leu Ala
    1235

<210> SEQ ID NO 3
<211> LENGTH: 3723
<212> TYPE: DNA
<213> ORGANISM: herpes simplex

<400> SEQUENCE: 3

| | | | | | | |
|---|---|---|---|---|---|---|
| atgttttgtg | ccgcgggcgg | cccggcttcc | cccgggggga | agtcggcggc | tcgggcggcg | 60 |
| tctgggtttt | ttgcccccca | caaccccgg | ggagccaccc | agacggcacc | gccgccttgc | 120 |
| cgccggcaga | acttctacaa | cccccacctc | gctcagaccg | gaacgcagcc | aaaggccccc | 180 |
| gggccggctc | agcgccatac | gtactacagc | gagtgcgacg | aatttcgatt | tatcgccccg | 240 |
| cgttcgctgg | acgaggacgc | ccccgcggag | cagcgcaccg | gggtccacga | cggccgcctc | 300 |
| cggcgcgccc | ctaaggtgta | ctgcgggggg | gacgagcgcg | acgtcctccg | cgtgggcccg | 360 |
| gagggcttct | ggccgcgtcg | cttgcgcctg | tggggcggtg | cggaccatgc | ccccgagggg | 420 |
| ttcgaccccca | ccgtcaccgt | cttccacgtg | tacgacatcc | tggagcacgt | ggaacacgcg | 480 |
| tacagcatgc | gcgccgccca | gctccacgag | cgatttatgg | acgccatcac | gcccgccggg | 540 |
| accgtcatca | cgcttctggg | tctgaccccc | gaaggccatc | gcgtcgccgt | tcacgtctac | 600 |
| ggcacgcggc | agtacttta | catgaacaag | gcggaggtgg | atcggcacct | gcagtgccgt | 660 |
| gccccgcgcg | atctctgcga | gcgcctggcg | gcggccctgc | gcgagtcgcc | ggggcgtcg | 720 |
| ttccgcggca | tctccgcgga | ccacttcgag | gcggaggtgg | tggagcgcgc | cgacgtgtac | 780 |
| tattacgaaa | cgcgcccgac | cctgtactac | cgcgtcttcg | tgcgaagcgg | gcgcgcgctg | 840 |
| gcctacctgt | gcgacaactt | tgccccgcg | atcaggaagt | acgaggggg | cgtcgacgcc | 900 |
| accaccggt | ttatcctgga | caacccgggg | tttgtcacct | tcggctggta | ccgcctcaag | 960 |
| cccggccgcg | ggaacgcgcc | ggcccaaccg | cgcccccga | cggcgttcgg | aacctcgagc | 1020 |
| gacgtcgagt | ttaactgcac | ggcggacaac | ctggccgtcg | aggggccat | gtgtgacctg | 1080 |
| ccggcctaca | agctcatgtg | cttcgatatc | gaatgcaagg | ccggggggga | ggacgagctg | 1140 |
| gcctttccgg | tcgcggaacg | cccggaagac | ctcgtcatcc | agatctcctg | tctgctctac | 1200 |
| gacctgtcca | ccaccgccct | cgagcacatc | ctcctgtttt | cgctcggatc | ctgcgacctc | 1260 |
| cccgagtccc | acctcagcga | tctcgcctcc | aggggcctgc | cggcccccgt | cgtcctggag | 1320 |
| tttgacagcg | aattcgagat | gctgctggcc | ttcatgacct | tcgtcaagca | gtacggcccc | 1380 |
| gagttcgtga | ccgggtacaa | catcatcaac | ttcgactggc | ccttcgtcct | gaccaagctg | 1440 |
| acggagatct | acaaggtccc | gctcgacggg | tacggcgca | tgaacggccg | gggtgtgttc | 1500 |
| cgcgtgtggg | acatcggcca | gagccacttt | cagaagcgca | gcaagatcaa | ggtgaacggg | 1560 |
| atggtgaaca | tcgacatgta | cggcatcatc | accgacaagg | tcaaactctc | cagctacaag | 1620 |
| ctgaacgccg | tcgccgaggc | cgtcttgaag | gacaagaaga | aggatctgag | ctaccgcgac | 1680 |
| atccccgcct | actacgcctc | cgggcccgcg | cagcgcgggg | tgatcggcga | gtattgtgtg | 1740 |
| caggactcgc | tgctggtcgg | gcagctgttc | ttcaagtttc | tgccgcacct | ggagctttcc | 1800 |
| gccgtcgcgc | gcctggcggg | catcaacatc | cccgcacca | tctacgacgg | ccagcagatc | 1860 |
| cgcgtcttca | cgtgcctcct | gcgccttgcg | ggccagaagg | gcttcatcct | gccggacacc | 1920 |

-continued

```
cagggggcggt tcggggcct cgacaaggag gcgcccaagc gcccggccgt gcctcggggg    1980 gaagggagc ggccgggga cgggaacggg gacgaggata aggacgacga cgaggacggg    2040
gacgaggacg gggacgagcg cgaggaggtc gcgcgcgaga ccgggggccg gcacgttggg    2100
taccaggggg cccgggtcct cgaccccacc tccgggtttc acgtcgaccc cgtggtggtg    2160
tttgactttg ccagcctgta ccccagcatc atccaggccc acaacctgtg cttcagtacg    2220
ctctccctgc ggcccgaggc cgtcgcgcac ctggaggcgg accgggacta cctggagatc    2280
gaggtggggg gccgacggct gttcttcgtg aaggcccacg tacgcgagag cctgctgagc    2340
atcctgctgc gcgactggct ggccatgcga aagcagatcc gctcgcggat cccccagagc    2400 cccccgagg aggccgtcct cctcgacaag caacaggccg ccatcaaggt ggtgtgcaac    2460
tcggtgtacg ggttcaccgg ggcgcagcac ggtcttctgc cctgcctgca cgtggccgcc    2520
accgtgacga ccatcggccg cgagatgctc ctcgcgacgc gcgcgtacgt gcacgcgcgc    2580
tgggcggagt tcgatcagct gctggccgac tttccggagg cggccggcat gcgcgccccc    2640
ggtccgtact ccatgcgcat catctacggg gacacggact ccattttcgt tttgtgccgc    2700
ggcctcacgg ccgcgggcct ggtggccatg ggcgacaaga tggcgagcca catctcgcgc    2760
gcgctgttcc tccccccgat caagctcgag tgcgaaaaaa cgttcaccaa gctgctgctc    2820
atcgccaaga aaagtacat cggcgtcatc tgcggggca agatgctcat caagggcgtg    2880
gatctggtgc gcaaaaacaa ctgcgcgttt atcaaccgca cctccagggc cctggtcgac    2940
ctgctgtttt acgacgatac cgtatccgga gcggccgccg cgttagccga gcgccccgca    3000
gaggagtggc tggcgcgacc cctgcccgag ggactgcagg cgttcggggc cgtcctcgta    3060
gacgcccatc ggcgcatcac cgaccccgag agggacatcc aggactttgt cctcaccgcc    3120
gaactgagca acacccgcg cgcgtacacc aacaagcgcc tggcccacct gacggtgtat    3180
tacaagctca tggcccgccg cgcgcaggtc ccgtccatca aggaccggat cccgtacgtg    3240
atcgtggccc agacccgcga ggtagaggag acggtcgcgc ggctggccgc cctccgcgag    3300
ctagacgccg ccgccccagg ggacgagccc gccccccag cggccctgcc ctccccggcc    3360
aagcgccccc gggagacgcc gtcgcatgcc gaccccccgg gaggcgcgtc caagcccccgc    3420 aagctgctgg tgtccgagct ggcggaggat cccgggtacg ccatcgcccg gggcgttccg    3480
ctcaacacgg actattactt ctcgcacctg ctggggcgg cctgcgtgac gttcaaggcc    3540
ctgtttggaa ataacgccaa gatcaccgag agtctgttaa agaggtttat tcccgagacg    3600 tggcacccccc cggacgacgt ggccgcgcgg ctcagggccg cggggttcgg gccggcgggg    3660
gccggcgcta cggcggagga aactcgtcga atgttgcata gagcctttga tactctagca    3720
tga                                                                3723
```

<210> SEQ ID NO 4
<211> LENGTH: 1240
<212> TYPE: PRT
<213> ORGANISM: herpes simplex

<400> SEQUENCE: 4

```
Met Phe Cys Ala Ala Gly Gly Pro Ala Ser Pro Gly Gly Lys Ser Ala
1               5                   10                  15

Ala Arg Ala Ala Ser Gly Phe Phe Ala Pro His Asn Pro Arg Gly Ala
                20                  25                  30

Thr Gln Thr Ala Pro Pro Pro Cys Arg Arg Gln Asn Phe Tyr Asn Pro
            35                  40                  45
```

```
His Leu Ala Gln Thr Gly Thr Gln Pro Lys Ala Pro Gly Pro Ala Gln
    50                  55                  60

Arg His Thr Tyr Tyr Ser Glu Cys Asp Glu Phe Arg Phe Ile Ala Pro
 65                  70                  75                  80

Arg Ser Leu Asp Glu Asp Ala Pro Ala Glu Gln Arg Thr Gly Val His
                 85                  90                  95

Asp Gly Arg Leu Arg Arg Ala Pro Lys Val Tyr Cys Gly Gly Asp Glu
             100                 105                 110

Arg Asp Val Leu Arg Val Gly Pro Glu Gly Phe Trp Pro Arg Arg Leu
             115                 120                 125

Arg Leu Trp Gly Gly Ala Asp His Ala Pro Glu Gly Phe Asp Pro Thr
        130                 135                 140

Val Thr Val Phe His Val Tyr Asp Ile Leu Glu His Val Glu His Ala
145                 150                 155                 160

Tyr Ser Met Arg Ala Ala Gln Leu His Glu Arg Phe Met Asp Ala Ile
                165                 170                 175

Thr Pro Ala Gly Thr Val Ile Thr Leu Leu Gly Leu Thr Pro Glu Gly
            180                 185                 190

His Arg Val Ala Val His Val Tyr Gly Thr Arg Gln Tyr Phe Tyr Met
            195                 200                 205

Asn Lys Ala Glu Val Asp Arg His Leu Gln Cys Arg Ala Pro Arg Asp
        210                 215                 220

Leu Cys Glu Arg Leu Ala Ala Ala Leu Arg Glu Ser Pro Gly Ala Ser
225                 230                 235                 240

Phe Arg Gly Ile Ser Ala Asp His Phe Glu Ala Glu Val Val Glu Arg
                245                 250                 255

Ala Asp Val Tyr Tyr Glu Thr Arg Pro Thr Leu Tyr Tyr Arg Val
            260                 265                 270

Phe Val Arg Ser Gly Arg Ala Leu Ala Tyr Leu Cys Asp Asn Phe Cys
        275                 280                 285

Pro Ala Ile Arg Lys Tyr Glu Gly Gly Val Asp Ala Thr Thr Arg Phe
290                 295                 300

Ile Leu Asp Asn Pro Gly Phe Val Thr Phe Gly Trp Tyr Arg Leu Lys
305                 310                 315                 320

Pro Gly Arg Gly Asn Ala Pro Ala Gln Pro Arg Pro Thr Ala Phe
                325                 330                 335

Gly Thr Ser Ser Asp Val Glu Phe Asn Cys Thr Ala Asp Asn Leu Ala
            340                 345                 350

Val Glu Gly Ala Met Cys Asp Leu Pro Ala Tyr Lys Leu Met Cys Phe
            355                 360                 365

Asp Ile Glu Cys Lys Ala Gly Gly Glu Asp Glu Leu Ala Phe Pro Val
    370                 375                 380

Ala Glu Arg Pro Glu Asp Leu Val Ile Gln Ile Ser Cys Leu Leu Tyr
385                 390                 395                 400

Asp Leu Ser Thr Thr Ala Leu Glu His Ile Leu Leu Phe Ser Leu Gly
            405                 410                 415

Ser Cys Asp Leu Pro Glu Ser His Leu Ser Asp Leu Ala Ser Arg Gly
            420                 425                 430

Leu Pro Ala Pro Val Val Leu Glu Phe Asp Ser Glu Phe Glu Met Leu
            435                 440                 445

Leu Ala Phe Met Thr Phe Val Lys Gln Tyr Gly Pro Glu Phe Val Thr
450                 455                 460

Gly Tyr Asn Ile Ile Asn Phe Asp Trp Pro Phe Val Leu Thr Lys Leu
```

-continued

```
465                 470                 475                 480
Thr Glu Ile Tyr Lys Val Pro Leu Asp Gly Tyr Gly Arg Met Asn Gly
                    485                 490                 495

Arg Gly Val Phe Arg Val Trp Asp Ile Gly Gln Ser His Phe Gln Lys
                500                 505                 510

Arg Ser Lys Ile Lys Val Asn Gly Met Val Asn Ile Asp Met Tyr Gly
            515                 520                 525

Ile Ile Thr Asp Lys Val Lys Leu Ser Ser Tyr Lys Leu Asn Ala Val
    530                 535                 540

Ala Glu Ala Val Leu Lys Asp Lys Lys Asp Leu Ser Tyr Arg Asp
545                 550                 555                 560

Ile Pro Ala Tyr Tyr Ala Ser Gly Pro Ala Gln Arg Gly Val Ile Gly
                565                 570                 575

Glu Tyr Cys Val Gln Asp Ser Leu Leu Val Gly Gln Leu Phe Phe Lys
                580                 585                 590

Phe Leu Pro His Leu Glu Leu Ser Ala Val Ala Arg Leu Ala Gly Ile
            595                 600                 605

Asn Ile Thr Arg Thr Ile Tyr Asp Gly Gln Gln Ile Arg Val Phe Thr
    610                 615                 620

Cys Leu Leu Arg Leu Ala Gly Gln Lys Gly Phe Ile Leu Pro Asp Thr
625                 630                 635                 640

Gln Gly Arg Phe Arg Gly Leu Asp Lys Glu Ala Pro Lys Arg Pro Ala
                645                 650                 655

Val Pro Arg Gly Glu Gly Glu Arg Pro Gly Asp Gly Asn Gly Asp Glu
                660                 665                 670

Asp Lys Asp Asp Glu Asp Gly Asp Glu Asp Gly Asp Glu Arg Glu
            675                 680                 685

Glu Val Ala Arg Glu Thr Gly Gly Arg His Val Gly Tyr Gln Gly Ala
    690                 695                 700

Arg Val Leu Asp Pro Thr Ser Gly Phe His Val Asp Pro Val Val
705                 710                 715                 720

Phe Asp Phe Ala Ser Leu Tyr Pro Ser Ile Ile Gln Ala His Asn Leu
                725                 730                 735

Cys Phe Ser Thr Leu Ser Leu Arg Pro Glu Ala Val Ala His Leu Glu
                740                 745                 750

Ala Asp Arg Asp Tyr Leu Glu Ile Glu Val Gly Gly Arg Arg Leu Phe
            755                 760                 765

Phe Val Lys Ala His Val Arg Glu Ser Leu Leu Ser Ile Leu Leu Arg
    770                 775                 780

Asp Trp Leu Ala Met Arg Lys Gln Ile Arg Ser Arg Ile Pro Gln Ser
785                 790                 795                 800

Pro Pro Glu Glu Ala Val Leu Leu Asp Lys Gln Gln Ala Ala Ile Lys
                805                 810                 815

Val Val Cys Asn Ser Val Tyr Gly Phe Thr Gly Ala Gln His Gly Leu
            820                 825                 830

Leu Pro Cys Leu His Val Ala Thr Val Thr Thr Ile Gly Arg Glu
                835                 840                 845

Met Leu Leu Ala Thr Arg Ala Tyr Val His Ala Arg Trp Ala Glu Phe
850                 855                 860

Asp Gln Leu Leu Ala Asp Phe Pro Glu Ala Gly Met Arg Ala Pro
865                 870                 875                 880

Gly Pro Tyr Ser Met Arg Ile Ile Tyr Gly Asp Thr Asp Ser Ile Phe
                885                 890                 895
```

-continued

```
Val Leu Cys Arg Gly Leu Thr Ala Ala Gly Leu Val Ala Met Gly Asp
            900                 905                 910
Lys Met Ala Ser His Ile Ser Arg Ala Leu Phe Leu Pro Pro Ile Lys
        915                 920                 925
Leu Glu Cys Glu Lys Thr Phe Thr Lys Leu Leu Leu Ile Ala Lys Lys
    930                 935                 940
Lys Tyr Ile Gly Val Ile Cys Gly Gly Lys Met Leu Ile Lys Gly Val
945                 950                 955                 960
Asp Leu Val Arg Lys Asn Asn Cys Ala Phe Ile Asn Arg Thr Ser Arg
                965                 970                 975
Ala Leu Val Asp Leu Leu Phe Tyr Asp Asp Thr Val Ser Gly Ala Ala
            980                 985                 990
Ala Ala Leu Ala Glu Arg Pro Ala Glu Glu Trp Leu Ala Arg Pro Leu
        995                 1000                1005
Pro Glu Gly Leu Gln Ala Phe Gly Ala Val Leu Val Asp Ala His
    1010                1015                1020
Arg Arg Ile Thr Asp Pro Glu Arg Asp Ile Gln Asp Phe Val Leu
    1025                1030                1035
Thr Ala Glu Leu Ser Arg His Pro Arg Ala Tyr Thr Asn Lys Arg
    1040                1045                1050
Leu Ala His Leu Thr Val Tyr Tyr Lys Leu Met Ala Arg Arg Ala
    1055                1060                1065
Gln Val Pro Ser Ile Lys Asp Arg Ile Pro Tyr Val Ile Val Ala
    1070                1075                1080
Gln Thr Arg Glu Val Glu Glu Thr Val Ala Arg Leu Ala Ala Leu
    1085                1090                1095
Arg Glu Leu Asp Ala Ala Ala Pro Gly Asp Glu Pro Ala Pro Pro
    1100                1105                1110
Ala Ala Leu Pro Ser Pro Ala Lys Arg Pro Arg Glu Thr Pro Ser
    1115                1120                1125
His Ala Asp Pro Pro Gly Gly Ala Ser Lys Pro Arg Lys Leu Leu
    1130                1135                1140
Val Ser Glu Leu Ala Glu Asp Pro Gly Tyr Ala Ile Ala Arg Gly
    1145                1150                1155
Val Pro Leu Asn Thr Asp Tyr Tyr Phe Ser His Leu Leu Gly Ala
    1160                1165                1170
Ala Cys Val Thr Phe Lys Ala Leu Phe Gly Asn Asn Ala Lys Ile
    1175                1180                1185
Thr Glu Ser Leu Leu Lys Arg Phe Ile Pro Glu Thr Trp His Pro
    1190                1195                1200
Pro Asp Asp Val Ala Ala Arg Leu Arg Ala Ala Gly Phe Gly Pro
    1205                1210                1215
Ala Gly Ala Gly Ala Thr Ala Glu Glu Thr Arg Arg Met Leu His
    1220                1225                1230
Arg Ala Phe Asp Thr Leu Ala
    1235                1240

<210> SEQ ID NO 5
<211> LENGTH: 3708
<212> TYPE: DNA
<213> ORGANISM: herpes simplex

<400> SEQUENCE: 5
atgttttccg gtggcggcgg cccgctgtcc cccggaggaa agtcggcggc cagggcggcg      60
```

-continued

```
tccgggtttt ttgcgcccgc cggccctcgc ggagccggcc ggggaccccc gccttgtttg     120
aggcaaaact tttacaaccc ctacctcgcc ccagtcggga cgcaacagaa gccgaccggg     180
ccaacccagc gccatacgta ctatagcgaa tgcgatgaat ttcgattcat cgccccgcgg     240
gtgctggacg aggatgcccc cccggagaag cgcgccgggg tgcacgacgg tcacctcaag     300
cgcgccccca aggtgtactg cggggggggac gagcgcgacg tcctccgcgt cgggtcgggc     360
ggcttctggc cgcggcgctc gcgcctgtgg ggcggcgtgg accacgcccc ggcggggttc     420
aaccccaccg tcaccgtctt tcacgtgtac gacatcctgg agaacgtgga gcacgcgtac     480
ggcatgcgcg cggcccagtt ccacgcgcgg tttatggacg ccatcacacc gacggggacc     540
gtcatcacgc tcctgggcct gactccggaa ggccaccggg tggccgttca cgtttacggc     600
acgcggcagt acttttacat gaacaaggag gaggttgaca ggcacctaca atgccgcgcc     660
ccacgagatc tctgcgagcg catggccgcg gccctgcgcg agtcccgggg cgcgtcgttc     720
cgcggcatct ccgcggacca cttcgaggcg gaggtggtgg agcgcaccga cgtgtactac     780
tacgagacgc gccccgctct gttttaccgc gtctacgtcc gaagcgggcg cgtgctgtcg     840
tacctgtgcg acaacttctg cccggccatc aagaagtacg agggtggggt cgacgccacc     900
acccggttca tcctggacaa ccccgggttc gtcaccttcg gctggtaccg tctcaaaccg     960
ggccggaaca acacgctagc ccagccgcgg gccccgatgg ccttcgggac atccagcgac    1020
gtcgagttta actgtacggc ggacaacctg ccatcgaggg gggcatgag cgacctaccg    1080 gcatacaagc tcatgtgctt cgatatcgaa tgcaaggcgg gggggggagga cgagctggcc    1140 tttccggtgg ccgggcaccc ggaggacctg gttattcaga tatcctgtct gctctacgac    1200
ctgtccacca ccgccctgga gcacgtcctc ctgttttcgc tcggttcctg cgacctcccc    1260
gaatcccacc tgaacgagct ggcggccagg ggcctgccca cgcccgtggt tctggaattc    1320
gacagcgaat tcgagatgct gttggccttc atgacccttg tgaaacagta cggccccgag    1380
ttcgtgaccg ggtacaacat catcaacttc gactggccct tcttgctggc caagttgacg    1440
gacatttaca aggtccccct ggacgggtac ggccgcatga acggccgggg cgtgtttcgc    1500
gtgtgggaca taggccagag ccacttccag aagcgcagca agataaaggt gaacggcatg    1560
gtgaacatcg acatgtacgg gatcataacc gacaagatca agctctcgag ctacaagctc    1620
aacgccgtgg ccgaagccgt cctgaaggac aagaagaagg acctgagcta tcgcgacatc    1680
cccgcctact acgccgccgg gcccgcgcaa cgcggggtga tcggcgagta ctgcatacag    1740
gattccctgc tggtgggcca gctgtttttt aagtttttgc cccatctgga gctctcggcc    1800
gtcgcgcgct tggcgggtat taacatcacc cgcaccatct acgacggcca gcagatccgc    1860
gtctttacgt gcctgctgcg cctggccgac cagaagggct ttattctgcc ggacacccag    1920
gggcgattta gggcgccgg gggggaggcg cccaagcgtc cggccgcagc ccggaggac     1980 gaggagcggc cagaggagga gggggaggac gaggacgaac gcgaggaggg cggggcgag     2040 cgggagccga agcgcgcgcg ggagaccgcc ggccggcacg tggggtacca gggggccagg     2100
gtccttgacc ccacttccgg gtttcacgtg aacccgtgg tggtgttcga ctttgccagc     2160
ctgtacccca gcatcatcca ggcccacaac ctgtgcttca gcacgctctc cctgagggcc     2220
gacgcagtgg cgcacctgga ggcgggcaag gactacctgg agatcgaggt gggggggcga     2280
cggctgttct tcgtcaaggc tcacgtgcga gagagcctcc tcagcatcct cctgcgggac     2340
tggctcgcca tgcgaaagca gatccgctcg cggattcccc agagcagccc cgaggaggcc     2400
```

-continued

```
gtgctcctgg acaagcagca ggccgccatc aaggtcgtgt gtaactcggt gtacgggttc    2460
acgggagcgc agcacggact cctgccgtgc ctgcacgttg ccgcgacggt gacgaccatc    2520
ggccgcgaga tgctgctcgc gacccgcgag tacgtccacg cgcgctgggc ggccttcgaa    2580
cagctcctgg ccgatttccc ggaggcggcc gacatgcgcg ccccggggcc ctattccatg    2640
cgcatcatct acggggacac ggactccata tttgtgctgt gccgcggcct cacggccgcc    2700
gggctgacgg ccatgggcga caagatggcg agccacatct cgcgcgcgct gtttctgccc    2760
cccatcaaac tcgagtgcga aaagacgttc accaagctgc tgctgatcgc caagaaaaag    2820
tacatcggcg tcatctacgg gggtaagatg ctcatcaagg gcgtggatct ggtgcgcaaa    2880
aacaactgcg cgtttatcaa ccgcacctcc agggccctgg tcgacctgct gttttacgac    2940
gataccgtat ccggagcggc cgccgcgtta gccgagcgcc ccgcagagga gtggctggcg    3000
cgacccctgc ccgagggact gcaggcgttc ggggccgtcc tcgtagacgc ccatcggcgc    3060
atcaccgacc cggagaggga catccaggac tttgtcctca ccgccgaact gagcagacac    3120
ccgcgcgcgt acaccaacaa gcgcctggcc cacctgacgg tgtattacaa gctcatggcc    3180
cgccgcgcgc aggtcccgtc catcaaggac cggatcccgt acgtgatcgt ggcccagacc    3240
cgcgaggtag aggagacggt cgcgcggctg gccgccctcc gcgagctaga cgccgccgcc    3300
ccaggggacg agcccgcccc ccccgcggcc ctgccctccc cggccaagcg ccccgggag    3360 acgccgtcgc atgccgaccc ccgggaggc gcgtccaagc cccgcaagct gctggtgtcc    3420
gagctggccg aggatcccgc atacgccatt gcccacggcg tcgccctgaa cacggactat    3480
tacttctccc acctgttggg ggcggcgtgc gtgacattca aggccctgtt tgggaataac    3540
gccaagatca ccgagagtct gttaaaaagg tttattcccg aagtgtggca ccccccggac    3600
gacgtggccg cgcggctccg ggccgcaggg ttcggggcgg tgggtgccgg cgctacggcg    3660
gaggaaactc gtcgaatgtt gcatagagcc tttgatactc tagcatga                3708
```

<210> SEQ ID NO 6
<211> LENGTH: 1235
<212> TYPE: PRT
<213> ORGANISM: herpes simplex

<400> SEQUENCE: 6

```
Met Phe Ser Gly Gly Gly Gly Pro Leu Ser Pro Gly Gly Lys Ser Ala
1               5                   10                  15

Ala Arg Ala Ala Ser Gly Phe Phe Ala Pro Ala Gly Pro Arg Gly Ala
            20                  25                  30

Gly Arg Gly Pro Pro Pro Cys Leu Arg Gln Asn Phe Tyr Asn Pro Tyr
        35                  40                  45

Leu Ala Pro Val Gly Thr Gln Gln Lys Pro Thr Gly Pro Thr Gln Arg
    50                  55                  60

His Thr Tyr Tyr Ser Glu Cys Asp Glu Phe Arg Phe Ile Ala Pro Arg
65                  70                  75                  80

Val Leu Asp Glu Asp Ala Pro Pro Glu Lys Arg Ala Gly Val His Asp
                85                  90                  95

Gly His Leu Lys Arg Ala Pro Lys Val Tyr Cys Gly Gly Asp Glu Arg
            100                 105                 110

Asp Val Leu Arg Val Gly Ser Gly Gly Phe Trp Pro Arg Arg Ser Arg
        115                 120                 125

Leu Trp Gly Gly Val Asp His Ala Pro Ala Gly Phe Asn Pro Thr Val
    130                 135                 140
```

-continued

```
Thr Val Phe His Val Tyr Asp Ile Leu Glu Asn Val Glu His Ala Tyr
145                 150                 155                 160

Gly Met Arg Ala Ala Gln Phe His Ala Arg Phe Met Asp Ala Ile Thr
                165                 170                 175

Pro Thr Gly Thr Val Ile Thr Leu Leu Gly Leu Thr Pro Glu Gly His
                180                 185                 190

Arg Val Ala Val His Val Tyr Gly Thr Arg Gln Tyr Phe Tyr Met Asn
                195                 200                 205

Lys Glu Glu Val Asp Arg His Leu Gln Cys Arg Ala Pro Arg Asp Leu
210                 215                 220

Cys Glu Arg Met Ala Ala Leu Arg Glu Ser Pro Gly Ala Ser Phe
225                 230                 235                 240

Arg Gly Ile Ser Ala Asp His Phe Glu Ala Glu Val Val Glu Arg Thr
                245                 250                 255

Asp Val Tyr Tyr Tyr Glu Thr Arg Pro Ala Leu Phe Tyr Arg Val Tyr
                260                 265                 270

Val Arg Ser Gly Arg Val Leu Ser Tyr Leu Cys Asp Asn Phe Cys Pro
        275                 280                 285

Ala Ile Lys Lys Tyr Glu Gly Gly Val Asp Ala Thr Thr Arg Phe Ile
290                 295                 300

Leu Asp Asn Pro Gly Phe Val Thr Phe Gly Trp Tyr Arg Leu Lys Pro
305                 310                 315                 320

Gly Arg Asn Asn Thr Leu Ala Gln Pro Arg Ala Pro Met Ala Phe Gly
                325                 330                 335

Thr Ser Ser Asp Val Glu Phe Asn Cys Thr Ala Asp Asn Leu Ala Ile
                340                 345                 350

Glu Gly Gly Met Ser Asp Leu Pro Ala Tyr Lys Leu Met Cys Phe Asp
                355                 360                 365

Ile Glu Cys Lys Ala Gly Gly Glu Asp Glu Leu Ala Phe Pro Val Ala
        370                 375                 380

Gly His Pro Glu Asp Leu Val Ile Gln Ile Ser Cys Leu Leu Tyr Asp
385                 390                 395                 400

Leu Ser Thr Thr Ala Leu Glu His Val Leu Leu Phe Ser Leu Gly Ser
                405                 410                 415

Cys Asp Leu Pro Glu Ser His Leu Asn Glu Leu Ala Ala Arg Gly Leu
                420                 425                 430

Pro Thr Pro Val Val Leu Glu Phe Asp Ser Glu Phe Glu Met Leu Leu
                435                 440                 445

Ala Phe Met Thr Leu Val Lys Gln Tyr Gly Pro Glu Phe Val Thr Gly
        450                 455                 460

Tyr Asn Ile Ile Asn Phe Asp Trp Pro Phe Leu Leu Ala Lys Leu Thr
465                 470                 475                 480

Asp Ile Tyr Lys Val Pro Leu Asp Gly Tyr Gly Arg Met Asn Gly Arg
                485                 490                 495

Gly Val Phe Arg Val Trp Asp Ile Gly Gln Ser His Phe Gln Lys Arg
                500                 505                 510

Ser Lys Ile Lys Val Asn Gly Met Val Asn Ile Asp Met Tyr Gly Ile
        515                 520                 525

Ile Thr Asp Lys Ile Lys Leu Ser Ser Tyr Lys Leu Asn Ala Val Ala
        530                 535                 540

Glu Ala Val Leu Lys Asp Lys Lys Asp Leu Ser Tyr Arg Asp Ile
545                 550                 555                 560

Pro Ala Tyr Tyr Ala Ala Gly Pro Ala Gln Arg Gly Val Ile Gly Glu
```

-continued

```
                565                 570                 575
Tyr Cys Ile Gln Asp Ser Leu Leu Val Gly Gln Leu Phe Lys Phe
                580                 585                 590
Leu Pro His Leu Glu Leu Ser Ala Val Ala Arg Leu Ala Gly Ile Asn
                595                 600                 605
Ile Thr Arg Thr Ile Tyr Asp Gly Gln Gln Ile Arg Val Phe Thr Cys
610                 615                 620
Leu Leu Arg Leu Ala Asp Gln Lys Gly Phe Ile Leu Pro Asp Thr Gln
625                 630                 635                 640
Gly Arg Phe Arg Gly Ala Gly Glu Ala Pro Lys Arg Pro Ala Ala
                645                 650                 655
Ala Arg Glu Asp Glu Glu Arg Pro Glu Glu Gly Glu Asp Glu Asp
                660                 665                 670
Glu Arg Glu Glu Gly Gly Glu Arg Glu Pro Glu Gly Ala Arg Glu
                675                 680                 685
Thr Ala Gly Arg His Val Gly Tyr Gln Gly Ala Arg Val Leu Asp Pro
690                 695                 700
Thr Ser Gly Phe His Val Asn Pro Val Val Phe Asp Phe Ala Ser
705                 710                 715                 720
Leu Tyr Pro Ser Ile Ile Gln Ala His Asn Leu Cys Phe Ser Thr Leu
                725                 730                 735
Ser Leu Arg Ala Asp Ala Val Ala His Leu Glu Ala Gly Lys Asp Tyr
                740                 745                 750
Leu Glu Ile Glu Val Gly Gly Arg Leu Phe Phe Val Lys Ala His
                755                 760                 765
Val Arg Glu Ser Leu Leu Ser Ile Leu Leu Arg Asp Trp Leu Ala Met
770                 775                 780
Arg Lys Gln Ile Arg Ser Arg Ile Pro Gln Ser Ser Pro Glu Glu Ala
785                 790                 795                 800
Val Leu Leu Asp Lys Gln Gln Ala Ala Ile Lys Val Val Cys Asn Ser
                805                 810                 815
Val Tyr Gly Phe Thr Gly Ala Gln His Gly Leu Leu Pro Cys Leu His
                820                 825                 830
Val Ala Ala Thr Val Thr Thr Ile Gly Arg Glu Met Leu Leu Ala Thr
                835                 840                 845
Arg Glu Tyr Val His Ala Arg Trp Ala Ala Phe Glu Gln Leu Leu Ala
850                 855                 860
Asp Phe Pro Glu Ala Ala Asp Met Arg Ala Pro Gly Pro Tyr Ser Met
865                 870                 875                 880
Arg Ile Ile Tyr Gly Asp Thr Asp Ser Ile Phe Val Leu Cys Arg Gly
                885                 890                 895
Leu Thr Ala Ala Gly Leu Thr Ala Met Gly Asp Lys Met Ala Ser His
                900                 905                 910
Ile Ser Arg Ala Leu Phe Leu Pro Pro Ile Lys Leu Glu Cys Glu Lys
                915                 920                 925
Thr Phe Thr Lys Leu Leu Ile Ala Lys Lys Lys Tyr Ile Gly Val
                930                 935                 940
Ile Tyr Gly Gly Lys Met Leu Ile Lys Gly Val Asp Leu Val Arg Lys
945                 950                 955                 960
Asn Asn Cys Ala Phe Ile Asn Arg Thr Ser Arg Ala Leu Val Asp Leu
                965                 970                 975
Leu Phe Tyr Asp Asp Thr Val Ser Gly Ala Ala Ala Ala Leu Ala Glu
                980                 985                 990
```

Arg Pro Ala Glu Glu Trp Leu Ala Arg Pro Leu Pro Glu Gly Leu Gln
       995                1000                1005

Ala Phe Gly Ala Val Leu Val Asp Ala His Arg Ile Thr Asp
       1010                1015                1020

Pro Glu Arg Asp Ile Gln Asp Phe Val Leu Thr Ala Glu Leu Ser
       1025                1030                1035

Arg His Pro Arg Ala Tyr Thr Asn Lys Arg Leu Ala His Leu Thr
       1040                1045                1050

Val Tyr Tyr Lys Leu Met Ala Arg Arg Ala Gln Val Pro Ser Ile
       1055                1060                1065

Lys Asp Arg Ile Pro Tyr Val Ile Val Ala Gln Thr Arg Glu Val
       1070                1075                1080

Glu Glu Thr Val Ala Arg Leu Ala Ala Leu Arg Glu Leu Asp Ala
       1085                1090                1095

Ala Ala Pro Gly Asp Glu Pro Ala Pro Pro Ala Ala Leu Pro Ser
       1100                1105                1110

Pro Ala Lys Arg Pro Arg Glu Thr Pro Ser His Ala Asp Pro Pro
       1115                1120                1125

Gly Gly Ala Ser Lys Pro Arg Lys Leu Leu Val Ser Glu Leu Ala
       1130                1135                1140

Glu Asp Pro Ala Tyr Ala Ile Ala His Gly Val Ala Leu Asn Thr
       1145                1150                1155

Asp Tyr Tyr Phe Ser His Leu Leu Gly Ala Ala Cys Val Thr Phe
       1160                1165                1170

Lys Ala Leu Phe Gly Asn Asn Ala Lys Ile Thr Glu Ser Leu Leu
       1175                1180                1185

Lys Arg Phe Ile Pro Glu Val Trp His Pro Pro Asp Asp Val Ala
       1190                1195                1200

Ala Arg Leu Arg Ala Ala Gly Phe Gly Ala Val Gly Ala Gly Ala
       1205                1210                1215

Thr Ala Glu Glu Thr Arg Arg Met Leu His Arg Ala Phe Asp Thr
       1220                1225                1230

Leu Ala
       1235

<210> SEQ ID NO 7
<211> LENGTH: 3708
<212> TYPE: DNA
<213> ORGANISM: herpes simplex

<400> SEQUENCE: 7
atgttttccg gtggcggcgg cccgctgtcc cccggaggaa agtcggcggc cagggcggcg     60
tccgggtttt ttgcgcccgc cggccctcgc ggagccggcc ggggacccccc gccttgcttg    120 aggcaaaact tttacaaccc ctacctcgcc ccagtcggga cgcaacagaa gccgaccggg    180
ccaacccagc gccatacgta ctatagcgaa tgcgatgaat tcgattcat cgccccgcgg     240 gtgctggacg aggatgcccc cccggagaag cgcgccgggg tgcacgacgg tcacctcaag    300
cgcgccccca aggtgtactg cggggggggac gagcgcgacg tcctccgcgt cgggtcgggc    360
ggcttctggc cgcggcgctc cgcgcctgtg ggcggcgtgg accacgcccc ggcggggttc    420
aaccccaccg tcaccgtctt tcacgtgtac gacatcctgg agaacgtgga gcacgcgtac    480
ggcatgcgcg cggcccagtt ccacgcgcgg tttatggacg ccatcacacc gacggggacc    540
gtcatcacgc tcctgggcct gactccggaa ggccaccggg tggccgttca cgtttacggc    600

```
acgcggcagt acttttacat gaacaaggag gaggtcgaca ggcacctaca atgccgcgcc    660
ccacgagatc tctgcgagcg catggccgcg ccctgcgcg agtccccggg cgcgtcgttc    720
cgcggcattt ccgcggacca cttcgaggcg gaggtggtgg agcgcaccga cgtgtactac    780
tacgagacgc gccccgctct gttttaccgc gtctacgtcc gaagcgggcg cgtgctgtcg    840
tacctgtgcg acaacttctg cccggccatc aagaagtacg agggtggggt cgacgccacc    900
acccggttca tcctggacaa ccccggggttc gtcaccttcg gctggtaccg tctcaaaccg    960
ggccggaaca acacgctagc ccagccgcgg gccccgatgg ccttcgggac atccagcgac   1020 gtcgagtttta actgtacggc ggacaacctg gccatcgagg ggggcatgag cgacctaccg   1080
gcatacaagc tcatgtgctt cgatatcgaa tgcaaggcgg ggggggagga cgagctggcc   1140
tttccggtgg ccggcaccc ggaggacctg gtcatccaga tatcctgtct gctctacgac   1200
ctgtccacca ccgccctgga gcacgtcctc ctgttttcgc tcggttcctg cgacctcccc   1260
gaatcccacc tgaacgagct ggcggccagg ggcctgccca cgcccgtggt tctggaattc   1320
gacagcgaat tcgagatgct gttggccttc atgacccttg tgaaacagta cggccccgag   1380
ttcgtgaccg ggtacaacat catcaacttc gactggccct tcttgctggc caagctgacg   1440
gacatttaca aggtcccccct ggacgggtac ggccgcatga acggccgggg cgtgtttcgc   1500
gtgtgggaca taggccagag ccacttccag aagcgcagca agataaaggt gaacggcatg   1560
gtgaacatcg acatgtacgg gattataacc gacaagatca agctctcgag ctacaagctc   1620
aacgccgtgg ccgaagccgt cctgaaggac aagaagaagg acctgagcta tcgcgacatc   1680
cccgcctact acgccgccgg gcccgcgcaa cgcggggtga tcggcgagta ctgcatacag   1740
gattccctgc tggtgggcca gctgtttttt aagtttttgc cccatctgga gctctcggcc   1800
gtcgcgcgct tggcgggtat taacatcacc cgcaccatct acgacggcca gcagatccgc   1860
gtctttacgt gcctgctgcg cctggccgac cagaagggct ttattctgcc ggacacccag   1920
gggcgattta ggggcggcgg ggggaggcg cccaagcgtc cggccgcagc ccgggaggac   1980
gaggagcggc cagaggagga ggggggaggac gaggacgaac gcgaggaggg cggggcgag    2040 cgggagccgg agggcgcgcg ggagaccgcc ggccggcacg tggggtacca gggggccagg   2100
gtccttgacc ccacttccgg gtttcatgtg aaccccgtgg tggtgttcga ctttgccagc   2160
ctgtacccca gcatcatcca ggcccacaac ctgtgcttca gcacgctctc cctgagggcc   2220
gacgcagtgg cgcacctgga ggcgggcaag gactacctgg agatcgaggt gggggggcga   2280
cggctgttct tcgtcaaggc tcacgtgcga gagagcctcc tcagcatcct cctgcgggac   2340
tggctcgcca tgcgaaagca gatccgctcg cggattcccc agagcagccc cgaggaggcc   2400
gtgctcctgg acaagcagca ggccgccatc aaggtcgtgt gtaactcggt ttacgggttc   2460
acgggagcgc agcacggact cctgccgtgc ctgcacgttg ccgcgacggt gacgaccatc   2520
ggccgcgaga tgctgctcgc gacccgcgag tacgtccacg cgcgctgggc ggccttcgaa   2580
cagctcctgc ccgatttccc ggaggcgcc gacatgcgcg ccccgggcc ctattccatg    2640 cgcatcatct acgggacac ggactccatc tttgtgctgt ccgcgcggcct cacggccgcc    2700 gggctgacgg ccgtgggcga caagatggcg agccacatct cgcgcgcgct gtttctgtcc   2760
cccatcaaac tcgagtgcga aaagacgttc accaagctgc tgctgatcgc caagaaaaag   2820
tacatcggcg tcatctacgg gggtaagatg ctcatcaagg gcgtggatct ggtgcgcaaa   2880
aacaactgcg cgtttatcaa ccgcacctcc agggccctgg tcgacctgct gttttacgac   2940
```

```
                                                -continued gataccgtat ccggagcggc cgccgcgtta gccgagcgcc ccgcagagga gtggctggcg      3000
cgacccctgc ccgagggact gcaggcgttc ggggccgtcc tcgtagacgc ccatcggcgc      3060
atcaccgacc cggagaggga catccaggac tttgtcctca ccgccgaact gagcagacac      3120
ccgcgcgcgt acaccaacaa gcgcctggcc cacctgacgg tgtattacaa gctcatggcc      3180
cgccgcgcgc aggtcccgtc catcaaggac cggatcccgt acgtgatcgt ggcccagacc      3240
cgcgaggtag aggagacggt cgcgcggctg gccgccctcc gcgagctcga cgccgccgcc      3300
ccaggggacg agcccgcccc ccccgcggcc ctgccctccc cggccaagcg ccccggggag      3360
acgccgttgc atgccgaccc cccgggaggc gcgtccaagc ccgcaagct gctggtgtcc       3420 gagctggccg aggatcccgc atacgccatt gcccacggcg tcgccctgaa cacggactat      3480
tacttctccc acctgttggg ggcggcgtgc gtgacattca aggccctgtt tgggaataac      3540
gccaagatca ccgagagtct gttaaaaagg tttattcccg aagtgtggca ccccccggac      3600
gacgtggccg cgcggctccg ggccgcaggg ttcggggcgg tgggtgccgg cgctacggcg      3660
gaggaaactc gtcgaatgtt gcatagagcc tttgatactc tagcatga                  3708

<210> SEQ ID NO 8
<211> LENGTH: 1235
<212> TYPE: PRT
<213> ORGANISM: herpes simplex

<400> SEQUENCE: 8

Met Phe Ser Gly Gly Gly Gly Pro Leu Ser Pro Gly Gly Lys Ser Ala
1               5                   10                  15

Ala Arg Ala Ala Ser Gly Phe Phe Ala Pro Ala Gly Pro Arg Gly Ala
            20                  25                  30

Gly Arg Gly Pro Pro Pro Cys Leu Arg Gln Asn Phe Tyr Asn Pro Tyr
        35                  40                  45

Leu Ala Pro Val Gly Thr Gln Gln Lys Pro Thr Gly Pro Thr Gln Arg
    50                  55                  60

His Thr Tyr Tyr Ser Glu Cys Asp Glu Phe Arg Phe Ile Ala Pro Arg
65              70                  75                  80

Val Leu Asp Glu Asp Ala Pro Pro Glu Lys Arg Ala Gly Val His Asp
            85                  90                  95

Gly His Leu Lys Arg Ala Pro Lys Val Tyr Cys Gly Gly Asp Glu Arg
        100                 105                 110

Asp Val Leu Arg Val Gly Ser Gly Gly Phe Trp Pro Arg Ser Arg
    115                 120                 125

Leu Trp Gly Gly Val Asp His Ala Pro Ala Gly Phe Asn Pro Thr Val
130                 135                 140

Thr Val Phe His Val Tyr Asp Ile Leu Glu Asn Val Glu His Ala Tyr
145             150                 155                 160

Gly Met Arg Ala Ala Gln Phe His Ala Arg Phe Met Asp Ala Ile Thr
            165                 170                 175

Pro Thr Gly Thr Val Ile Thr Leu Leu Gly Leu Thr Pro Glu Gly His
        180                 185                 190

Arg Val Ala Val His Val Tyr Gly Thr Arg Gln Tyr Phe Tyr Met Asn
    195                 200                 205

Lys Glu Glu Val Asp Arg His Leu Gln Cys Arg Ala Pro Arg Asp Leu
    210                 215                 220

Cys Glu Arg Met Ala Ala Ala Leu Arg Glu Ser Pro Gly Ala Ser Phe
225                 230                 235                 240
```

-continued

```
Arg Gly Ile Ser Ala Asp His Phe Glu Ala Glu Val Val Glu Arg Thr
                245                 250                 255

Asp Val Tyr Tyr Tyr Glu Thr Arg Pro Ala Leu Phe Tyr Arg Val Tyr
            260                 265                 270

Val Arg Ser Gly Arg Val Leu Ser Tyr Leu Cys Asp Asn Phe Cys Pro
        275                 280                 285

Ala Ile Lys Lys Tyr Glu Gly Val Asp Ala Thr Thr Arg Phe Ile
290                 295                 300

Leu Asp Asn Pro Gly Phe Val Thr Phe Gly Trp Tyr Arg Leu Lys Pro
305                 310                 315                 320

Gly Arg Asn Asn Thr Leu Ala Gln Pro Arg Ala Pro Met Ala Phe Gly
                325                 330                 335

Thr Ser Ser Asp Val Glu Phe Asn Cys Thr Ala Asp Asn Leu Ala Ile
            340                 345                 350

Glu Gly Gly Met Ser Asp Leu Pro Ala Tyr Lys Leu Met Cys Phe Asp
        355                 360                 365

Ile Glu Cys Lys Ala Gly Gly Glu Asp Glu Leu Ala Phe Pro Val Ala
370                 375                 380

Gly His Pro Glu Asp Leu Val Ile Gln Ile Ser Cys Leu Leu Tyr Asp
385                 390                 395                 400

Leu Ser Thr Thr Ala Leu Glu His Val Leu Leu Phe Ser Leu Gly Ser
                405                 410                 415

Cys Asp Leu Pro Glu Ser His Leu Asn Glu Leu Ala Ala Arg Gly Leu
            420                 425                 430

Pro Thr Pro Val Val Leu Glu Phe Asp Ser Glu Phe Glu Met Leu Leu
        435                 440                 445

Ala Phe Met Thr Leu Val Lys Gln Tyr Gly Pro Glu Phe Val Thr Gly
    450                 455                 460

Tyr Asn Ile Ile Asn Phe Asp Trp Pro Phe Leu Leu Ala Lys Leu Thr
465                 470                 475                 480

Asp Ile Tyr Lys Val Pro Leu Asp Gly Tyr Gly Arg Met Asn Gly Arg
                485                 490                 495

Gly Val Phe Arg Val Trp Asp Ile Gly Gln Ser His Phe Gln Lys Arg
            500                 505                 510

Ser Lys Ile Lys Val Asn Gly Met Val Asn Ile Asp Met Tyr Gly Ile
        515                 520                 525

Ile Thr Asp Lys Ile Lys Leu Ser Ser Tyr Lys Leu Asn Ala Val Ala
530                 535                 540

Glu Ala Val Leu Lys Asp Lys Lys Asp Leu Ser Tyr Arg Asp Ile
545                 550                 555                 560

Pro Ala Tyr Tyr Ala Ala Gly Pro Ala Gln Arg Gly Val Ile Gly Glu
                565                 570                 575

Tyr Cys Ile Gln Asp Ser Leu Leu Val Gly Gln Leu Phe Phe Lys Phe
            580                 585                 590

Leu Pro His Leu Glu Leu Ser Ala Val Ala Arg Leu Ala Gly Ile Asn
        595                 600                 605

Ile Thr Arg Thr Ile Tyr Asp Gly Gln Gln Ile Arg Val Phe Thr Cys
    610                 615                 620

Leu Leu Arg Leu Ala Asp Gln Lys Gly Phe Ile Leu Pro Asp Thr Gln
625                 630                 635                 640

Gly Arg Phe Arg Gly Gly Gly Glu Ala Pro Lys Arg Pro Ala Ala
                645                 650                 655

Ala Arg Glu Asp Glu Glu Arg Pro Glu Glu Glu Gly Glu Asp Glu Asp
```

-continued

```
                     660                 665                 670
Glu Arg Glu Glu Gly Gly Glu Arg Glu Pro Gly Ala Arg Glu
            675                 680                 685
Thr Ala Gly Arg His Val Gly Tyr Gln Gly Ala Arg Val Leu Asp Pro
    690                 695                 700
Thr Ser Gly Phe His Val Asn Pro Val Val Phe Asp Phe Ala Ser
705                 710                 715                 720
Leu Tyr Pro Ser Ile Ile Gln Ala His Asn Leu Cys Phe Ser Thr Leu
                725                 730                 735
Ser Leu Arg Ala Asp Ala Val Ala His Leu Glu Ala Gly Lys Asp Tyr
            740                 745                 750
Leu Glu Ile Glu Val Gly Gly Arg Arg Leu Phe Phe Val Lys Ala His
            755                 760                 765
Val Arg Glu Ser Leu Leu Ser Ile Leu Leu Arg Asp Trp Leu Ala Met
770                 775                 780
Arg Lys Gln Ile Arg Ser Arg Ile Pro Gln Ser Ser Pro Glu Glu Ala
785                 790                 795                 800
Val Leu Leu Asp Lys Gln Gln Ala Ala Ile Lys Val Val Cys Asn Ser
            805                 810                 815
Val Tyr Gly Phe Thr Gly Ala Gln His Gly Leu Leu Pro Cys Leu His
            820                 825                 830
Val Ala Ala Thr Val Thr Thr Ile Gly Arg Glu Met Leu Leu Ala Thr
            835                 840                 845
Arg Glu Tyr Val His Ala Arg Trp Ala Ala Phe Glu Gln Leu Leu Ala
            850                 855                 860
Asp Phe Pro Glu Ala Ala Asp Met Arg Ala Pro Gly Pro Tyr Ser Met
865                 870                 875                 880
Arg Ile Ile Tyr Gly Asp Thr Asp Ser Ile Phe Val Leu Cys Arg Gly
            885                 890                 895
Leu Thr Ala Ala Gly Leu Thr Ala Val Gly Asp Lys Met Ala Ser His
            900                 905                 910
Ile Ser Arg Ala Leu Phe Leu Ser Pro Ile Lys Leu Glu Cys Glu Lys
            915                 920                 925
Thr Phe Thr Lys Leu Leu Leu Ile Ala Lys Lys Lys Tyr Ile Gly Val
            930                 935                 940
Ile Tyr Gly Gly Lys Met Leu Ile Lys Gly Val Asp Leu Val Arg Lys
945                 950                 955                 960
Asn Asn Cys Ala Phe Ile Asn Arg Thr Ser Arg Ala Leu Val Asp Leu
                965                 970                 975
Leu Phe Tyr Asp Asp Thr Val Ser Gly Ala Ala Ala Leu Ala Glu
            980                 985                 990
Arg Pro Ala Glu Glu Trp Leu Ala Arg Pro Leu Pro Glu Gly Leu Gln
            995                 1000                1005
Ala Phe Gly Ala Val Leu Val Asp Ala His Arg Arg Ile Thr Asp
    1010                1015                1020
Pro Glu Arg Asp Ile Gln Asp Phe Val Leu Thr Ala Glu Leu Ser
    1025                1030                1035
Arg His Pro Arg Ala Tyr Thr Asn Lys Arg Leu Ala His Leu Thr
    1040                1045                1050
Val Tyr Tyr Lys Leu Met Ala Arg Arg Ala Gln Val Pro Ser Ile
    1055                1060                1065
Lys Asp Arg Ile Pro Tyr Val Ile Val Ala Gln Thr Arg Glu Val
    1070                1075                1080
```

```
Glu Glu Thr Val Ala Arg Leu Ala Ala Leu Arg Glu Leu Asp Ala
1085                1090                1095

Ala Ala Pro Gly Asp Glu Pro Ala Pro Pro Ala Ala Leu Pro Ser
1100                1105                1110

Pro Ala Lys Arg Pro Arg Glu Thr Pro Leu His Ala Asp Pro Pro
1115                1120                1125

Gly Gly Ala Ser Lys Pro Arg Lys Leu Leu Val Ser Glu Leu Ala
1130                1135                1140

Glu Asp Pro Ala Tyr Ala Ile Ala His Gly Val Ala Leu Asn Thr
1145                1150                1155

Asp Tyr Tyr Phe Ser His Leu Leu Gly Ala Ala Cys Val Thr Phe
1160                1165                1170

Lys Ala Leu Phe Gly Asn Asn Ala Lys Ile Thr Glu Ser Leu Leu
1175                1180                1185

Lys Arg Phe Ile Pro Glu Val Trp His Pro Pro Asp Asp Val Ala
1190                1195                1200

Ala Arg Leu Arg Ala Ala Gly Phe Gly Ala Val Gly Ala Gly Ala
1205                1210                1215

Thr Ala Glu Glu Thr Arg Arg Met Leu His Arg Ala Phe Asp Thr
1220                1225                1230

Leu Ala
1235

<210> SEQ ID NO 9
<211> LENGTH: 3708
<212> TYPE: DNA
<213> ORGANISM: herpes simplex

<400> SEQUENCE: 9
atgttttccg gtggcggcgg cccgctgtcc cccggaggaa agtcggcggc cagggcggcg      60
tccgggtttt ttgcgcccgc cggccctcgc ggagccggcc ggggaccccc gccttgtttg     120
aggcaaaact tttacaaccc ctacctcgcc ccagtcggga cgcaacagaa gccgaccggg     180
ccaacccagc gccatacgta ctatagcgaa tgcgatgaat tcgattcat cgccccgcgg      240 gtgctggacg aggatgcccc cccggagaag cgcgccgggg tgcacgacgg tcacctcaag     300 cgcgcccccca aggtgtactg cgggggggac gagcgcgacg tcctccgcgt cgggtcgggc    360
ggcttctggc cgcggcgctc cgcgcctgtgg ggcggcgtgg accacgcccc ggcggggttc    420
aaccccaccg tcaccgtctt tcacgtgtat gacatcctgg agaacgtgga gcacgcgtac    480
ggcatgcgcg cggcccagtt ccacgcgcgg tttatggacg ccatcacacc gacggggacc    540
gtcatcacgc tcctgggcct gactccggaa ggccaccggg tggccgttca cgtttacggc    600
acgcggcagt acttttacat gaacaaggag gaggttgaca ggcacctaca atgccgcgcc    660
ccacgagatc tctgcgagcg catggccgcg gccctgcgcg agtccccggg cgcgtcgttc    720
cgcggcatct ccgcggacca cttcgaggcg gaggtggtgg agcgcaccga cgtgtactac    780
tacgagacgc gccccgctct gttttaccgc gtctacgtcc gaagcgggcg cgtgctgtcg    840
tacctgtgcg acaacttctg cccggccatc aagaagtacg aggtgggggt cgacgccacc    900
acccggttca tcctggacaa ccccgggttc gtcaccttcg gctggtaccg tctcaaaccg    960
ggccggaaca acacgctagc ccagccgcgg gccccgatgg ccttcgggac atccagcgat    1020 gtcgagtttta actgtacggc ggacaacctg gccatcgagg ggggcatgag cgacctaccg    1080
gcatacaagc tcatgtgctt cgatatcgaa tgcaaggcgg ggggggagga cgagctggcc    1140
```

```
tttccggtgg ccgggcaccc ggaggacctg gtcatccaga tatcctgtct gctctacgac    1200
ctgtccacca ccgccctgga gcacgtcctc ctgttttcgc tcggttcctg cgacctcccc    1260
gaatcccacc tgaacgagct ggcggccagg ggcctgccca cgcccgtggt tctggaattc    1320
gacagcgaat tcgagatgct gttggccttc atgacccttg tgaaacagta cggccccgag    1380
ttcgtgaccg ggtacaacat aatcaacttc gactggccct tcttgctggc caagctgacg    1440
gacatttaca aggtcccccct ggacgggtac ggccgcatga acggccgggg cgtgtttcgc    1500
gtgtgggaca taggccagag ccacttccag aagcgcagca agataaaggt gaacggcatg    1560
gtgaacatcg acatgtacgg gattataacc gacaagatca agctctcgag ctacaagctc    1620
aacgccgtgg ccgaagccgt cctgaaggac aagaagaagg acctgagcta tcgcgacatc    1680
cccacctact acgccgccgg gcccgcgcaa cgcggggtga tcggcgagta ctgcatacag    1740
gattccctgc tggtgggcca gctgtttttt aagttttttgc cccatctgga gctctcggcc    1800
gtcgcgcgct tggcgggtat taacatcacc cgcaccatct acgacggcca gcagatccgc    1860
gtctttacgt gcctgctgcg cctggccgac cagaagggct ttattctgcc ggacacccag    1920
gggcgattta ggggcgccgg gggggaggcg cccaagcgtc cggccgcagc ccgggaggac    1980
gaggagcggc cagaggagga gggggaggac gagaacgaac gcgaggaggg cggggccgag    2040
cgggagccgg agggcgcgcg ggagaccgcc ggccggcacg tggggtacca ggggggccagg   2100 gtccttgacc ccacttccgg gtttcacgtg aaccccgtgg tggtgttcga cttttgccagc   2160 ctgtacccca gcatcatcca ggcccacaac ctgtgcttca gcacgctctc cctgagggcc    2220
gacgcagtgg cgcacctgga ggcgggcaag gactacctgg agatcgaggt ggggggggcga    2280 cggctgttct tcgtcaaggc tcacgtgcga gagagcctcc tcagcatcct cctgcgggac    2340
tggctcgcca tgcgaaagca gatccgctcg cggattcccc agagcagccc cgaggaggcc    2400
gtgctcctgg acaagcagca ggccgccatc aaggtcgtgt gtaactcggt ttacgggttc    2460
acgggagcgc agcacggact cctgccgtgc ctgcacgttg ccgcgacggt gacgaccatc    2520
ggccgcgaga tgctgctcgc gacccgcgag tacgtccacg cgcgctgggc ggccttcgaa    2580 cagctccctgg ccgatttccc ggaggcggcc gacatgcgcg ccccccgggcc ctattccatg    2640 cgcatcatct acgggacac ggactccata tttgtgctgt gccgcggcct cacggccgcc     2700
gggctgacgg ccgtgggcga caagatggcg agccacatct cgcgcgcgct gtttctgccc    2760
cccatcaaac tcgagtgcga aaagacgttc accaagctgc tgctgatcgc caagaaaaag    2820
tacatcggcg tcatctacgg gggtaagatg ctcatcaagg gcgtggatct ggtgcgcaaa    2880
aacaactgcg cgtttatcaa ccgcacctcc agggccctgg tcgacctgct gttttacgac    2940
gataccgtat ccggagcggc cgccgcgtta gccgagcgcc ccgcagagga gtggctggcg    3000 cgaccctgc ccgagggact gcaggcgttc ggggccgtcc tcgtagacgc ccatcggcgc     3060
atcaccgacc cggagaggga catccaggac tttgttctca ccgccgaact gagcagacac    3120
ccgcgcgcgt acaccaacaa cgccctggcc cacctgacgg tgtattacaa gctcatggcc    3180
cgccgcgcgc aggtcccgtc catcaaggac cggatcccgt acgtgatcgt ggcccagacc    3240
cgcgaggtag aggagacggt cgcgcggctg gccgccctcc gcgagctaga cgccgccgcc    3300
ccaggggacg agcccgcccc ccccgcggcc ctgccctccc cggccaagcg ccccgggag    3360 acgccgtcgc ctgccgaccc cccggggaggc gcgtccaagc ccgcaagct gctggtgtcc    3420 gagctggccg aggatcccgc atacgccatt gcccacggcg tcgccctgaa cacggactat    3480
```

```
tacttctccc acctgttggg ggcggcgtgc gtgacattca aggccctgtt tgggaataac    3540
gccaagatca ccgagagtct gttaaaaagg tttattcccg aagtgtggca ccccccggac    3600
gacgtggccg cgcggctccg gaccgcaggg ttcggggcgg tgggtgccgg cgctacggcg    3660
gaggaaactc gtcgaatgtt gcatagagcc tttgatactc tagcatga                3708
```

<210> SEQ ID NO 10
<211> LENGTH: 1235
<212> TYPE: PRT
<213> ORGANISM: herpes simplex

<400> SEQUENCE: 10

```
Met Phe Ser Gly Gly Gly Pro Leu Ser Pro Gly Gly Lys Ser Ala
1               5                   10                  15

Ala Arg Ala Ala Ser Gly Phe Phe Ala Pro Ala Gly Pro Arg Gly Ala
                20                  25                  30

Gly Arg Gly Pro Pro Pro Cys Leu Arg Gln Asn Phe Tyr Asn Pro Tyr
            35                  40                  45

Leu Ala Pro Val Gly Thr Gln Gln Lys Pro Thr Gly Pro Thr Gln Arg
50                  55                  60

His Thr Tyr Tyr Ser Glu Cys Asp Glu Phe Arg Phe Ile Ala Pro Arg
65                  70                  75                  80

Val Leu Asp Glu Asp Ala Pro Pro Glu Lys Arg Ala Gly Val His Asp
                85                  90                  95

Gly His Leu Lys Arg Ala Pro Lys Val Tyr Cys Gly Gly Asp Glu Arg
            100                 105                 110

Asp Val Leu Arg Val Gly Ser Gly Gly Phe Trp Pro Arg Arg Ser Arg
        115                 120                 125

Leu Trp Gly Gly Val Asp His Ala Pro Ala Gly Phe Asn Pro Thr Val
130                 135                 140

Thr Val Phe His Val Tyr Asp Ile Leu Glu Asn Val Glu His Ala Tyr
145                 150                 155                 160

Gly Met Arg Ala Ala Gln Phe His Ala Arg Phe Met Asp Ala Ile Thr
                165                 170                 175

Pro Thr Gly Thr Val Ile Thr Leu Leu Gly Leu Thr Pro Glu Gly His
            180                 185                 190

Arg Val Ala Val His Val Tyr Gly Thr Arg Gln Tyr Phe Tyr Met Asn
        195                 200                 205

Lys Glu Glu Val Asp Arg His Leu Gln Cys Arg Ala Pro Arg Asp Leu
    210                 215                 220

Cys Glu Arg Met Ala Ala Ala Leu Arg Glu Ser Pro Gly Ala Ser Phe
225                 230                 235                 240

Arg Gly Ile Ser Ala Asp His Phe Glu Ala Glu Val Val Glu Arg Thr
                245                 250                 255

Asp Val Tyr Tyr Tyr Glu Thr Arg Pro Ala Leu Phe Tyr Arg Val Tyr
            260                 265                 270

Val Arg Ser Gly Arg Val Leu Ser Tyr Leu Cys Asp Asn Phe Cys Pro
        275                 280                 285

Ala Ile Lys Lys Tyr Glu Gly Gly Val Asp Ala Thr Thr Arg Phe Ile
    290                 295                 300

Leu Asp Asn Pro Gly Phe Val Thr Phe Gly Trp Tyr Arg Leu Lys Pro
305                 310                 315                 320

Gly Arg Asn Asn Thr Leu Ala Gln Pro Arg Ala Pro Met Ala Phe Gly
                325                 330                 335
```

```
Thr Ser Ser Asp Val Glu Phe Asn Cys Thr Ala Asp Asn Leu Ala Ile
            340                 345                 350

Glu Gly Gly Met Ser Asp Leu Pro Ala Tyr Lys Leu Met Cys Phe Asp
            355                 360                 365

Ile Glu Cys Lys Ala Gly Gly Glu Asp Glu Leu Ala Phe Pro Val Ala
            370                 375             380

Gly His Pro Glu Asp Leu Val Ile Gln Ile Ser Cys Leu Leu Tyr Asp
385                 390                 395                 400

Leu Ser Thr Thr Ala Leu Glu His Val Leu Leu Phe Ser Leu Gly Ser
            405                 410                 415

Cys Asp Leu Pro Glu Ser His Leu Asn Glu Leu Ala Ala Arg Gly Leu
            420                 425                 430

Pro Thr Pro Val Val Leu Glu Phe Asp Ser Glu Phe Glu Met Leu Leu
            435                 440                 445

Ala Phe Met Thr Leu Val Lys Gln Tyr Gly Pro Glu Phe Val Thr Gly
            450                 455                 460

Tyr Asn Ile Ile Asn Phe Asp Trp Pro Phe Leu Leu Ala Lys Leu Thr
465                 470                 475                 480

Asp Ile Tyr Lys Val Pro Leu Asp Gly Tyr Gly Arg Met Asn Gly Arg
            485                 490                 495

Gly Val Phe Arg Val Trp Asp Ile Gly Gln Ser His Phe Gln Lys Arg
            500                 505                 510

Ser Lys Ile Lys Val Asn Gly Met Val Asn Ile Asp Met Tyr Gly Ile
            515                 520                 525

Ile Thr Asp Lys Ile Lys Leu Ser Ser Tyr Lys Leu Asn Ala Val Ala
            530                 535                 540

Glu Ala Val Leu Lys Asp Lys Lys Asp Leu Ser Tyr Arg Asp Ile
545                 550                 555                 560

Pro Thr Tyr Tyr Ala Ala Gly Pro Ala Gln Arg Gly Val Ile Gly Glu
            565                 570                 575

Tyr Cys Ile Gln Asp Ser Leu Leu Val Gly Gln Leu Phe Phe Lys Phe
            580                 585                 590

Leu Pro His Leu Glu Leu Ser Ala Val Ala Arg Leu Ala Gly Ile Asn
            595                 600                 605

Ile Thr Arg Thr Ile Tyr Asp Gly Gln Gln Ile Arg Val Phe Thr Cys
            610                 615                 620

Leu Leu Arg Leu Ala Asp Gln Lys Gly Phe Ile Leu Pro Asp Thr Gln
625                 630                 635                 640

Gly Arg Phe Arg Gly Ala Gly Gly Glu Ala Pro Lys Arg Pro Ala Ala
            645                 650                 655

Ala Arg Glu Asp Glu Glu Arg Pro Glu Glu Glu Gly Glu Asp Glu Asn
            660                 665                 670

Glu Arg Glu Glu Gly Gly Gly Arg Glu Pro Glu Gly Ala Arg Glu
            675                 680                 685

Thr Ala Gly Arg His Val Gly Tyr Gln Gly Ala Arg Val Leu Asp Pro
            690                 695                 700

Thr Ser Gly Phe His Val Asn Pro Val Val Phe Asp Phe Ala Ser
705                 710                 715                 720

Leu Tyr Pro Ser Ile Ile Gln Ala His Asn Leu Cys Phe Ser Thr Leu
            725                 730                 735

Ser Leu Arg Ala Asp Ala Val Ala His Leu Glu Ala Gly Lys Asp Tyr
            740                 745                 750

Leu Glu Ile Glu Val Gly Gly Arg Arg Leu Phe Phe Val Lys Ala His
```

-continued

```
              755                 760                 765
Val Arg Glu Ser Leu Leu Ser Ile Leu Leu Arg Asp Trp Leu Ala Met
    770                 775                 780

Arg Lys Gln Ile Arg Ser Arg Ile Pro Gln Ser Ser Pro Glu Glu Ala
785                 790                 795                 800

Val Leu Leu Asp Lys Gln Gln Ala Ala Ile Lys Val Val Cys Asn Ser
                805                 810                 815

Val Tyr Gly Phe Thr Gly Ala Gln His Gly Leu Leu Pro Cys Leu His
                820                 825                 830

Val Ala Ala Thr Val Thr Thr Ile Gly Arg Glu Met Leu Leu Ala Thr
                835                 840                 845

Arg Glu Tyr Val His Ala Arg Trp Ala Ala Phe Glu Gln Leu Leu Ala
    850                 855                 860

Asp Phe Pro Glu Ala Ala Asp Met Arg Ala Pro Gly Pro Tyr Ser Met
865                 870                 875                 880

Arg Ile Ile Tyr Gly Asp Thr Asp Ser Ile Phe Val Leu Cys Arg Gly
                885                 890                 895

Leu Thr Ala Ala Gly Leu Thr Ala Val Gly Asp Lys Met Ala Ser His
                900                 905                 910

Ile Ser Arg Ala Leu Phe Leu Pro Pro Ile Lys Leu Glu Cys Glu Lys
    915                 920                 925

Thr Phe Thr Lys Leu Leu Leu Ile Ala Lys Lys Tyr Ile Gly Val
    930                 935                 940

Ile Tyr Gly Gly Lys Met Leu Ile Lys Gly Val Asp Leu Val Arg Lys
945                 950                 955                 960

Asn Asn Cys Ala Phe Ile Asn Arg Thr Ser Arg Ala Leu Val Asp Leu
                965                 970                 975

Leu Phe Tyr Asp Asp Thr Val Ser Gly Ala Ala Ala Leu Ala Glu
                980                 985                 990

Arg Pro Ala Glu Glu Trp Leu Ala Arg Pro Leu Pro Glu Gly Leu Gln
            995                 1000                1005

Ala Phe Gly Ala Val Leu Val Asp Ala His Arg Arg Ile Thr Asp
       1010                1015                1020

Pro Glu Arg Asp Ile Gln Asp Phe Val Leu Thr Ala Glu Leu Ser
       1025                1030                1035

Arg His Pro Arg Ala Tyr Thr Asn Lys Arg Leu Ala His Leu Thr
       1040                1045                1050

Val Tyr Tyr Lys Leu Met Ala Arg Arg Ala Gln Val Pro Ser Ile
       1055                1060                1065

Lys Asp Arg Ile Pro Tyr Val Ile Val Ala Gln Thr Arg Glu Val
       1070                1075                1080

Glu Glu Thr Val Ala Arg Leu Ala Ala Leu Arg Glu Leu Asp Ala
       1085                1090                1095

Ala Ala Pro Gly Asp Glu Pro Ala Pro Pro Ala Ala Leu Pro Ser
       1100                1105                1110

Pro Ala Lys Arg Pro Arg Glu Thr Pro Ser Pro Ala Asp Pro Pro
       1115                1120                1125

Gly Gly Ala Ser Lys Pro Arg Lys Leu Leu Val Ser Glu Leu Ala
       1130                1135                1140

Glu Asp Pro Ala Tyr Ala Ile Ala His Gly Val Ala Leu Asn Thr
       1145                1150                1155

Asp Tyr Tyr Phe Ser His Leu Leu Gly Ala Ala Cys Val Thr Phe
       1160                1165                1170
```

| Lys | Ala | Leu | Phe | Gly | Asn | Asn | Ala | Lys | Ile | Thr | Glu | Ser | Leu | Leu |
|     | 1175 |    |    |    |    | 1180 |    |    |    |    | 1185 |    |    |    |

| Lys | Arg | Phe | Ile | Pro | Glu | Val | Trp | His | Pro | Pro | Asp | Asp | Val | Ala |
|     | 1190 |    |    |    |    | 1195 |    |    |    |    | 1200 |    |    |    |

| Ala | Arg | Leu | Arg | Thr | Ala | Gly | Phe | Gly | Ala | Val | Gly | Ala | Gly | Ala |
|     | 1205 |    |    |    |    | 1210 |    |    |    |    | 1215 |    |    |    |

| Thr | Ala | Glu | Glu | Thr | Arg | Arg | Met | Leu | His | Arg | Ala | Phe | Asp | Thr |
|     | 1220 |    |    |    |    | 1225 |    |    |    |    | 1230 |    |    |    |

Leu Ala
 1235

<210> SEQ ID NO 11
<211> LENGTH: 3729
<212> TYPE: DNA
<213> ORGANISM: herpes simplex

<400> SEQUENCE: 11

```
atgtttttca acccgtatct gagcggcggc gtgaccggcg gtgcggtcgc gggtggccgg      60
cgtcagcgtt cgcagcccgg ctccgcgcag ggctcgggca agcggccgcc acagaaacag     120
tttttgcaga tcgtgccgcg aggtgtcatg ttcgacggtc agacgggggtt gatcaagcat     180
aagacgggac ggctgcctct catgttctat cgagagatta acatttgtt gagtcatgac      240
atggtttggc cgtgtccttg cgcgagacc ctggtgggtc cgtggtggg acctattcgt       300
tttcacacct acgatcagac ggacgccgtg ctcttcttcg actcgcccga aaacgtgtcg     360
ccgcgctatc gtcagcatct ggtgccttcg gggaacgtgt tgcgtttctt cggggccaca     420
gaacacggct acagtatctg cgtcaacgtt tcgggcagc gcagctactt ttactgtgag      480
tacagcgaca ccgataggct gcgtgaggtc attgccagcg tgggcgaact agtgcccgaa     540
ccgcggacgc catacgccgt gtctgtcacg ccggccacca agacctccat ctatgggtac     600
gggacgcgac ccgtgcccga tttgcagtgt gtgtctatca gcaactggac catggccaga     660
aaaatcggcg agtatctgct ggagcagggt tttcccgtgt acgaggtccg tgtggatccg     720
ctgacgcgtt tggtcatcga tcggcggatc accacgttcg gctggtgctc cgtgaatcgt     780
tacgactggc ggcagcaggg tcgcgcgtcg acttgtgata tcgaggtaga ctgcgatgtc     840
tctgacctgg tggctgtgcc cgacgacagc tcgtggccgc gctatcgatg cctgtccttc     900
gatatcgagt gcatgagcgg cgagggtggt tttccctgcg ccgagaagtc cgatgacatt     960
gtcattcaga tctcgtgcgt gtgctacgag acgggggggaa acaccgccgt ggatcagggg    1020
atcccaaacg ggaacgatgg tcggggctgc acttcggagg gtgtgatctt tgggcactcg    1080
ggtcttcatc tctttacgat cggcacctgc gggcaggtgg gcccagacgt ggacgtctac    1140
gagttccctt ccgaatacga gctgctgctg ggctttatgc ttttctttca acggtacgcg    1200
ccggcctttg tgaccggtta caacatcaac tcttttgact tgaagtacat cctcacgcgt    1260
ctcgagtacc tgtataaggt ggactcgcag cgcttctgca agttgcctac ggcgcagggc    1320
ggccgtttct ttttacacag ccccgccgtg ggttttaagc ggcagtacgc cgccgctttt    1380
ccctcggctt ctcacaacaa tccggccagc acggccgcca ccaaggtgta tattgcgggt    1440
tcggtggtta tcgacatgta ccctgtatgc atggccaaga ctaactcgcc caactataag    1500
ctcaacacta tggccgagct ttacctgcgg caacgcaagg atgacctgtc ttacaaggac    1560
atcccgcgtt gtttcgtggc taatgccgag ggccgcgccc aggtaggccg ttactgtctg    1620
caggacgccg tattggtgcg cgatctgttc aacaccatta attttcacta cgaggccggg    1680
```

-continued

```
gccatcgcgc ggctggctaa aattccgttg cggcgtgtca tctttgacgg acagcagatc    1740
cgtatctaca cctcgctgct ggacgagtgc gcctgccgcg attttatcct gcccaaccac    1800
tacagcaaag gtacgacggt gcccgaaacg aatagcgttg ctgtgtcacc taacgctgct    1860
atcatctcta ccgccgctgt gcccggcgac gcggggttctg tggcggctat gtttcagatg   1920
tcgccgccct tgcaatctgc gccgtccagt caggacggca tttcacccgg ctccggcagt    1980
aacagtagta gcagcgtcgg cgttttcagc gtcggctccg gcagtagtgg cggcgtcggc    2040
gtttccaacg acaatcacgg cgccggcggt actgcggcgcg tttcgtacca gggcgccacg   2100
gtgtttgagc ccgaggtggg ttactacaac gaccccgtgg ccgtgttcga ctttgccagc    2160
ctctacccctt ccatcatcat ggcccacaac ctctgctact ccaccctgct ggtgccgggt   2220
ggcgagtacc ctgtggaccc cgccgacgta tacagcgtca cgctagagaa cggcgtgacc    2280
caccgctttg tgcgtgcttc ggtgcgcgtc tcggtgctct cggaactgct caacaagtgg    2340
gtttcgcagc ggcgtgccgt gcgcgaatgc atgcgcgagt gtcaagaccc tgtgcgccgt    2400
atgctgctcg acaaggaaca gatggcgctc aaagtaacgt gcaacgcttt ctacggtttt    2460
accggcgcgc tgaacggtat gatgccgtgt ctgcccatcg ccgccagcat cacgcgcatc    2520
ggtcgcgaca tgctagagcg cacggcgcgg ttcatcaaag acaactttttc agagccgtgt   2580
ttttttgcaca attttttttaa tcaggaagac tatgtagtgg gaacgcggga ggggggattcg  2640
gaggagagca gcgcgttacc ggaggggctc gaaacatcgt caggggggctc gaacgaacgg   2700
cgggtggagg cgcgggtcat ctacggggac acggacagcg tgtttgtccg ctttcgtggc    2760
ctgacgccgc aggctctggt ggcgcgtggg cccagcctgg cgcactacgt gacggcctgt    2820
cttttttgtgg agcccgtcaa gctggagttt gaaaaggtct tcgtctctct tatgatgatc    2880
tgcaagaaac gttacatcgg caaagtggag ggcgcctcgg gtctgagcat gaagggcgtg    2940
gatctggtgc gcaagacggc ctgcgagttc gtcaagggcg tcacgcgtga cgtcctctcg    3000
ctgctctttg aggatcgcga ggtctcggaa gcagccgtgc gcctgtcgcg cctctcactc    3060
gatgaagtca agaagtacgg cgtgccacgc ggtttctggc gtatcttacg ccgcttggtg    3120
caggcccgcg acgatctgta cctgcaccgt gtgcgtgtcg aggacctggt gctttcgtcg    3180
gtgctctcta aggacatctc gctgtaccgt caatctaacc tgccgcacat tgccgtcatt    3240
aagcgattgg cggcccgttc tgaggagcta ccctcggtcg gggatcgggt cttttacgtt    3300
ctgacggcgc ccggtgtccg gacggcgccg cagggttcct ccgacaacgg tgattctgta    3360
accgccggcg tggtttcccg gtcggacgcg attgatggca cggacgacga cgctgacggc    3420
ggcggggtag aggagagcaa caggagagga ggagagccgg caaagaagag ggcgcggaaa    3480
ccaccgtcgg ccgtgtgcaa ctacgaggta gccgaagatc cgagctacgt gcgcgagcac    3540
ggcgtgccca ttcacgccga caagtacttt gagcaggttc tcaaggctgt aactaacgtg    3600
ctgtcgcccg tctttcccgg cggcgaaacc gcgcgcaagg acaagttttt gcacatggtg    3660
ctgccgcggc gcttgcactt ggagccggct tttctgccgt acagtgtcaa ggcgcacgaa    3720
tgctgttga                                                             3729
```

<210> SEQ ID NO 12
<211> LENGTH: 1242
<212> TYPE: PRT
<213> ORGANISM: herpes simplex

<400> SEQUENCE: 12

```
Met Phe Phe Asn Pro Tyr Leu Ser Gly Val Thr Gly Gly Ala Val
1               5                   10                  15

Ala Gly Gly Arg Arg Gln Arg Ser Gln Pro Gly Ser Ala Gln Gly Ser
            20                  25                  30

Gly Lys Arg Pro Pro Gln Lys Gln Phe Leu Gln Ile Val Pro Arg Gly
        35                  40                  45

Val Met Phe Asp Gly Gln Thr Gly Leu Ile Lys His Lys Thr Gly Arg
50                      55                  60

Leu Pro Leu Met Phe Tyr Arg Glu Ile Lys His Leu Leu Ser His Asp
65                  70                  75                  80

Met Val Trp Pro Cys Pro Trp Arg Glu Thr Leu Val Gly Arg Val Val
                85                  90                  95

Gly Pro Ile Arg Phe His Thr Tyr Asp Gln Thr Asp Ala Val Leu Phe
            100                 105                 110

Phe Asp Ser Pro Glu Asn Val Ser Pro Arg Tyr Arg Gln His Leu Val
        115                 120                 125

Pro Ser Gly Asn Val Leu Arg Phe Gly Ala Thr Glu His Gly Tyr
130                 135                 140

Ser Ile Cys Val Asn Val Phe Gly Gln Arg Ser Tyr Phe Tyr Cys Glu
145             150                 155                 160

Tyr Ser Asp Thr Asp Arg Leu Arg Glu Val Ile Ala Ser Val Gly Glu
                165                 170                 175

Leu Val Pro Glu Pro Arg Thr Pro Tyr Ala Val Ser Val Thr Pro Ala
            180                 185                 190

Thr Lys Thr Ser Ile Tyr Gly Tyr Gly Thr Arg Pro Val Pro Asp Leu
            195                 200                 205

Gln Cys Val Ser Ile Ser Asn Trp Thr Met Ala Arg Lys Ile Gly Glu
    210                 215                 220

Tyr Leu Leu Glu Gln Gly Phe Pro Val Tyr Glu Val Arg Val Asp Pro
225                 230                 235                 240

Leu Thr Arg Leu Val Ile Asp Arg Arg Ile Thr Thr Phe Gly Trp Cys
                245                 250                 255

Ser Val Asn Arg Tyr Asp Trp Arg Gln Gln Gly Arg Ala Ser Thr Cys
            260                 265                 270

Asp Ile Glu Val Asp Cys Asp Val Ser Asp Leu Val Ala Val Pro Asp
        275                 280                 285

Asp Ser Ser Trp Pro Arg Tyr Arg Cys Leu Ser Phe Asp Ile Glu Cys
        290                 295                 300

Met Ser Gly Glu Gly Gly Phe Pro Cys Ala Glu Lys Ser Asp Asp Ile
305                 310                 315                 320

Val Ile Gln Ile Ser Cys Val Cys Tyr Glu Thr Gly Gly Asn Thr Ala
                325                 330                 335

Val Asp Gln Gly Ile Pro Asn Gly Asn Asp Gly Arg Gly Cys Thr Ser
            340                 345                 350

Glu Gly Val Ile Phe Gly His Ser Gly Leu His Leu Phe Thr Ile Gly
            355                 360                 365

Thr Cys Gly Gln Val Gly Pro Asp Val Asp Val Tyr Glu Phe Pro Ser
        370                 375                 380

Glu Tyr Glu Leu Leu Leu Gly Phe Met Leu Phe Phe Gln Arg Tyr Ala
385                 390                 395                 400

Pro Ala Phe Val Thr Gly Tyr Asn Ile Asn Ser Phe Asp Leu Lys Tyr
            405                 410                 415

Ile Leu Thr Arg Leu Glu Tyr Leu Tyr Lys Val Asp Ser Gln Arg Phe
```

-continued

```
               420              425              430
Cys Lys Leu Pro Thr Ala Gln Gly Gly Arg Phe Phe Leu His Ser Pro
            435              440              445
Ala Val Gly Phe Lys Arg Gln Tyr Ala Ala Phe Pro Ser Ala Ser
450              455              460
His Asn Asn Pro Ala Ser Thr Ala Ala Thr Lys Val Tyr Ile Ala Gly
465              470              475              480
Ser Val Val Ile Asp Met Tyr Pro Val Cys Met Ala Lys Thr Asn Ser
                485              490              495
Pro Asn Tyr Lys Leu Asn Thr Met Ala Glu Leu Tyr Leu Arg Gln Arg
            500              505              510
Lys Asp Asp Leu Ser Tyr Lys Asp Ile Pro Arg Cys Phe Val Ala Asn
            515              520              525
Ala Glu Gly Arg Ala Gln Val Gly Arg Tyr Cys Leu Gln Asp Ala Val
530              535              540
Leu Val Arg Asp Leu Phe Asn Thr Ile Asn Phe His Tyr Glu Ala Gly
545              550              555              560
Ala Ile Ala Arg Leu Ala Lys Ile Pro Leu Arg Arg Val Ile Phe Asp
                565              570              575
Gly Gln Gln Ile Arg Ile Tyr Thr Ser Leu Leu Asp Glu Cys Ala Cys
            580              585              590
Arg Asp Phe Ile Leu Pro Asn His Tyr Ser Lys Gly Thr Thr Val Pro
            595              600              605
Glu Thr Asn Ser Val Ala Val Ser Pro Asn Ala Ala Ile Ile Ser Thr
            610              615              620
Ala Ala Val Pro Gly Asp Ala Gly Ser Val Ala Ala Met Phe Gln Met
625              630              635              640
Ser Pro Pro Leu Gln Ser Ala Pro Ser Ser Gln Asp Gly Val Ser Pro
                645              650              655
Gly Ser Gly Ser Asn Ser Ser Ser Val Gly Val Phe Ser Val Gly
            660              665              670
Ser Gly Ser Ser Gly Gly Val Gly Val Ser Asn Asp Asn His Gly Ala
            675              680              685
Gly Gly Thr Ala Ala Val Ser Tyr Gln Gly Ala Thr Val Phe Glu Pro
690              695              700
Glu Val Gly Tyr Tyr Asn Asp Pro Val Ala Val Phe Asp Phe Ala Ser
705              710              715              720
Leu Tyr Pro Ser Ile Ile Met Ala His Asn Leu Cys Tyr Ser Thr Leu
                725              730              735
Leu Val Pro Gly Gly Glu Tyr Pro Val Asp Pro Ala Asp Val Tyr Ser
            740              745              750
Val Thr Leu Glu Asn Gly Val Thr His Arg Phe Val Arg Ala Ser Val
            755              760              765
Arg Val Ser Val Leu Ser Glu Leu Leu Asn Lys Trp Val Ser Gln Arg
            770              775              780
Arg Ala Val Arg Glu Cys Met Arg Glu Cys Gln Asp Pro Val Arg Arg
785              790              795              800
Met Leu Leu Asp Lys Glu Gln Met Ala Leu Lys Val Thr Cys Asn Ala
                805              810              815
Phe Tyr Gly Phe Thr Gly Ala Leu Asn Gly Met Met Pro Cys Leu Pro
            820              825              830
Ile Ala Ala Ser Ile Thr Arg Ile Gly Arg Asp Met Leu Glu Arg Thr
            835              840              845
```

-continued

```
Ala Arg Phe Ile Lys Asp Asn Phe Ser Glu Pro Cys Phe Leu His Asn
    850                 855                 860
Phe Phe Asn Gln Glu Asp Tyr Val Val Gly Thr Arg Glu Gly Asp Ser
865                 870                 875                 880
Glu Glu Ser Ser Ala Leu Pro Glu Gly Leu Glu Thr Ser Ser Gly Gly
                885                 890                 895
Ser Asn Glu Arg Arg Val Glu Ala Arg Val Ile Tyr Gly Asp Thr Asp
            900                 905                 910
Ser Val Phe Val Arg Phe Arg Gly Leu Thr Pro Gln Ala Leu Val Ala
            915                 920                 925
Arg Gly Pro Ser Leu Ala His Tyr Val Thr Ala Cys Leu Phe Val Glu
    930                 935                 940
Pro Val Lys Leu Glu Phe Glu Lys Val Phe Val Ser Leu Met Met Ile
945                 950                 955                 960
Cys Lys Lys Arg Tyr Ile Gly Lys Val Glu Gly Ala Ser Gly Leu Ser
                965                 970                 975
Met Lys Gly Val Asp Leu Val Arg Lys Thr Ala Cys Glu Phe Val Lys
            980                 985                 990
Gly Val Thr Arg Asp Val Leu Ser Leu Leu Phe Glu Asp Arg Glu Val
            995                 1000                1005
Ser Glu Ala Ala Val Arg Leu Ser Arg Leu Ser Leu Asp Glu Val
    1010                1015                1020
Lys Lys Tyr Gly Val Pro Arg Gly Phe Trp Arg Ile Leu Arg Arg
    1025                1030                1035
Leu Val Gln Ala Arg Asp Asp Leu Tyr Leu His Arg Val Arg Val
    1040                1045                1050
Glu Asp Leu Val Leu Ser Ser Val Leu Ser Lys Asp Ile Ser Leu
    1055                1060                1065
Tyr Arg Gln Ser Asn Leu Pro His Ile Ala Val Ile Lys Arg Leu
    1070                1075                1080
Ala Ala Arg Ser Glu Glu Leu Pro Ser Val Gly Asp Arg Val Phe
    1085                1090                1095
Tyr Val Leu Thr Ala Pro Gly Val Arg Thr Ala Pro Gln Gly Ser
    1100                1105                1110
Ser Asp Asn Gly Asp Ser Val Thr Ala Gly Val Val Ser Arg Ser
    1115                1120                1125
Asp Ala Ile Asp Gly Thr Asp Asp Asp Ala Asp Gly Gly Gly Val
    1130                1135                1140
Glu Glu Ser Asn Arg Arg Gly Gly Glu Pro Ala Lys Lys Arg Ala
    1145                1150                1155
Arg Lys Pro Pro Ser Ala Val Cys Asn Tyr Glu Val Ala Glu Asp
    1160                1165                1170
Pro Ser Tyr Val Arg Glu His Gly Val Pro Ile His Ala Asp Lys
    1175                1180                1185
Tyr Phe Glu Gln Val Leu Lys Ala Val Thr Asn Val Leu Ser Pro
    1190                1195                1200
Val Phe Pro Gly Gly Glu Thr Ala Arg Lys Asp Lys Phe Leu His
    1205                1210                1215
Met Val Leu Pro Arg Arg Leu His Leu Glu Pro Ala Phe Leu Pro
    1220                1225                1230
Tyr Ser Val Lys Ala His Glu Cys Cys
    1235                1240
```

```
<210> SEQ ID NO 13
<211> LENGTH: 1242
<212> TYPE: PRT
<213> ORGANISM: herpes simplex

<400> SEQUENCE: 13

Met Phe Asn Pro Tyr Leu Ser Gly Gly Val Thr Gly Gly Ala Val
1               5                   10                  15

Ala Gly Gly Arg Arg Gln Arg Ser Gln Pro Gly Ser Ala Gln Gly Ser
                20                  25                  30

Gly Lys Arg Pro Pro Gln Lys Gln Phe Leu Gln Ile Val Pro Arg Gly
                35                  40                  45

Val Met Phe Asp Gly Gln Thr Gly Leu Ile Lys His Lys Thr Gly Arg
    50                  55                  60

Leu Pro Leu Met Phe Tyr Arg Glu Ile Lys His Leu Leu Ser His Asp
65                  70                  75                  80

Met Val Trp Pro Cys Pro Trp Arg Glu Thr Leu Val Gly Arg Val Val
                85                  90                  95

Gly Pro Ile Arg Phe His Thr Tyr Asp Gln Thr Asp Ala Val Leu Phe
                100                 105                 110

Phe Asp Ser Pro Glu Asn Val Ser Pro Arg Tyr Arg Gln His Leu Val
                115                 120                 125

Pro Ser Gly Asn Val Leu Arg Phe Gly Ala Thr Glu His Gly Tyr
    130                 135                 140

Ser Ile Cys Val Asn Val Phe Gly Gln Arg Ser Tyr Phe Tyr Cys Glu
145                 150                 155                 160

Tyr Ser Asp Thr Asp Arg Leu Arg Glu Val Ile Ala Ser Val Gly Glu
                165                 170                 175

Leu Val Pro Glu Pro Arg Thr Pro Tyr Ala Val Ser Val Thr Pro Ala
                180                 185                 190

Thr Lys Thr Ser Ile Tyr Gly Tyr Gly Thr Arg Pro Val Pro Asp Leu
                195                 200                 205

Gln Cys Val Ser Ile Ser Asn Trp Thr Met Ala Arg Lys Ile Gly Glu
    210                 215                 220

Tyr Leu Leu Glu Gln Gly Phe Pro Val Tyr Glu Val Arg Val Asp Pro
225                 230                 235                 240

Leu Thr Arg Leu Val Ile Asp Arg Arg Ile Thr Thr Phe Gly Trp Cys
                245                 250                 255

Ser Val Asn Arg Tyr Asp Trp Arg Gln Gln Gly Arg Ala Ser Thr Cys
                260                 265                 270

Asp Ile Glu Val Asp Cys Asp Val Ser Asp Leu Val Ala Val Pro Asp
    275                 280                 285

Asp Ser Ser Trp Pro Arg Tyr Arg Cys Leu Ser Phe Asp Ile Glu Cys
    290                 295                 300

Met Ser Gly Glu Gly Gly Phe Pro Cys Ala Glu Lys Ser Asp Asp Ile
305                 310                 315                 320

Val Ile Gln Ile Ser Cys Val Cys Tyr Glu Thr Gly Gly Asn Thr Ala
                325                 330                 335

Val Asp Gln Gly Ile Pro Asn Gly Asn Asp Gly Arg Gly Cys Thr Ser
                340                 345                 350

Glu Gly Val Ile Phe Gly His Ser Gly Leu His Leu Phe Thr Ile Gly
                355                 360                 365

Thr Cys Gly Gln Val Gly Pro Asp Val Asp Val Tyr Glu Phe Pro Ser
    370                 375                 380
```

-continued

```
Glu Tyr Glu Leu Leu Gly Phe Met Leu Phe Gln Arg Tyr Ala
385                 390                 395                 400

Pro Ala Phe Val Thr Gly Tyr Asn Ile Asn Ser Phe Asp Leu Lys Tyr
            405                 410                 415

Ile Leu Thr Arg Leu Glu Tyr Leu Tyr Lys Val Asp Ser Gln Arg Phe
            420                 425                 430

Cys Lys Leu Pro Thr Ala Gln Gly Gly Arg Phe Phe Leu His Ser Pro
            435                 440                 445

Ala Val Gly Phe Lys Arg Gln Tyr Ala Ala Phe Pro Ser Ala Ser
450                 455                 460

His Asn Asn Pro Ala Ser Thr Ala Ala Thr Lys Val Tyr Ile Ala Gly
465                 470                 475                 480

Ser Val Val Ile Asp Met Tyr Pro Val Cys Met Ala Lys Thr Asn Ser
                485                 490                 495

Pro Asn Tyr Lys Leu Asn Thr Met Ala Glu Leu Tyr Leu Arg Gln Arg
            500                 505                 510

Lys Asp Asp Leu Ser Tyr Lys Asp Ile Pro Arg Cys Phe Val Ala Asn
            515                 520                 525

Ala Glu Gly Arg Ala Gln Val Gly Arg Tyr Cys Leu Gln Asp Ala Val
            530                 535                 540

Leu Val Arg Asp Leu Phe Asn Thr Ile Asn Phe His Tyr Glu Ala Gly
545                 550                 555                 560

Ala Ile Ala Arg Leu Ala Lys Ile Pro Leu Arg Arg Val Ile Phe Asp
                565                 570                 575

Gly Gln Gln Ile Arg Ile Tyr Thr Ser Leu Leu Asp Glu Cys Ala Cys
            580                 585                 590

Arg Asp Phe Ile Leu Pro Asn His Tyr Ser Lys Gly Thr Thr Val Pro
            595                 600                 605

Glu Thr Asn Ser Val Ala Val Ser Pro Asn Ala Ala Ile Ile Ser Thr
            610                 615                 620

Ala Ala Val Pro Gly Asp Ala Gly Ser Val Ala Ala Met Phe Gln Met
625                 630                 635                 640

Ser Pro Pro Leu Gln Ser Ala Pro Ser Ser Gln Asp Gly Val Ser Pro
            645                 650                 655

Gly Ser Gly Ser Asn Ser Ser Ser Val Gly Val Phe Ser Val Gly
            660                 665                 670

Ser Gly Ser Ser Gly Gly Val Gly Val Ser Asn Asp Asn His Gly Ala
            675                 680                 685

Gly Gly Thr Ala Ala Val Ser Tyr Gln Gly Ala Thr Val Phe Glu Pro
690                 695                 700

Glu Val Gly Tyr Tyr Asn Asp Pro Val Ala Val Phe Asp Phe Ala Ser
705                 710                 715                 720

Leu Tyr Pro Ser Ile Ile Met Ala His Asn Leu Cys Tyr Ser Thr Leu
                725                 730                 735

Leu Val Pro Gly Gly Glu Tyr Pro Val Asp Pro Ala Asp Val Tyr Ser
            740                 745                 750

Val Thr Leu Glu Asn Gly Val Thr His Arg Phe Val Arg Ala Ser Val
            755                 760                 765

Arg Val Ser Val Leu Ser Glu Leu Leu Asn Lys Trp Val Ser Gln Arg
            770                 775                 780

Arg Ala Val Arg Glu Cys Met Arg Glu Cys Gln Asp Pro Val Arg Arg
785                 790                 795                 800
```

-continued

```
Met Leu Leu Asp Lys Glu Gln Met Ala Leu Lys Val Thr Cys Asn Ala
            805                 810                 815

Phe Tyr Gly Phe Thr Gly Val Val Asn Gly Met Met Pro Cys Leu Pro
            820                 825                 830

Ile Ala Ala Ser Ile Thr Arg Ile Gly Arg Asp Met Leu Glu Arg Thr
            835                 840                 845

Ala Arg Phe Ile Lys Asp Asn Phe Ser Glu Pro Cys Phe Leu His Asn
    850                 855                 860

Phe Phe Asn Gln Glu Asp Tyr Val Val Gly Thr Arg Glu Gly Asp Ser
865                 870                 875                 880

Glu Glu Ser Ser Ala Leu Pro Glu Gly Leu Glu Thr Ser Ser Gly Gly
            885                 890                 895

Ser Asn Glu Arg Arg Val Glu Ala Arg Val Ile Tyr Gly Asp Thr Asp
            900                 905                 910

Ser Val Phe Val Arg Phe Arg Gly Leu Thr Pro Gln Ala Leu Val Ala
            915                 920                 925

Arg Gly Pro Ser Leu Ala His Tyr Val Thr Ala Cys Leu Phe Val Glu
    930                 935                 940

Pro Val Lys Leu Glu Phe Glu Lys Val Phe Val Ser Leu Met Met Ile
945                 950                 955                 960

Cys Lys Lys Arg Tyr Ile Gly Lys Val Glu Gly Ala Ser Gly Leu Ser
            965                 970                 975

Met Lys Gly Val Asp Leu Val Arg Lys Thr Ala Cys Glu Phe Val Lys
            980                 985                 990

Gly Val Thr Arg Asp Val Leu Ser Leu Leu Phe Glu Asp Arg Glu Val
            995                 1000                1005

Ser Glu Ala Ala Val Arg Leu Ser Arg Leu Ser Leu Asp Glu Val
    1010                1015                1020

Lys Lys Tyr Gly Val Pro Arg Gly Phe Trp Arg Ile Leu Arg Arg
    1025                1030                1035

Leu Val Gln Ala Arg Asp Asp Leu Tyr Leu His Arg Val Arg Val
    1040                1045                1050

Glu Asp Leu Val Leu Ser Ser Val Leu Ser Lys Asp Ile Ser Leu
    1055                1060                1065

Tyr Arg Gln Ser Asn Leu Pro His Ile Ala Val Ile Lys Arg Leu
    1070                1075                1080

Ala Ala Arg Ser Glu Glu Leu Pro Ser Val Gly Asp Arg Val Phe
    1085                1090                1095

Tyr Val Leu Thr Ala Pro Gly Val Arg Thr Ala Pro Gln Gly Ser
    1100                1105                1110

Ser Asp Asn Gly Asp Ser Val Thr Ala Gly Val Val Ser Arg Ser
    1115                1120                1125

Asp Ala Ile Asp Gly Thr Asp Asp Ala Asp Gly Gly Gly Val
    1130                1135                1140

Glu Glu Ser Asn Arg Arg Gly Gly Glu Pro Ala Lys Lys Arg Ala
    1145                1150                1155

Arg Lys Pro Pro Ser Ala Val Cys Asn Tyr Glu Val Ala Glu Asp
    1160                1165                1170

Pro Ser Tyr Val Arg Glu His Gly Val Pro Ile His Ala Asp Lys
    1175                1180                1185

Tyr Phe Glu Gln Val Leu Lys Ala Val Thr Asn Val Leu Ser Pro
    1190                1195                1200

Val Phe Pro Gly Gly Glu Thr Ala Arg Lys Asp Lys Phe Leu His
```

-continued

```
            1205                1210                1215

Met Val Leu Pro Arg Arg Leu  His Leu Glu Pro Ala  Phe Leu Pro
    1220                1225                1230

Tyr Ser  Val Lys Ala His Glu  Cys Cys
    1235                1240

<210> SEQ ID NO 14
<211> LENGTH: 1238
<212> TYPE: PRT
<213> ORGANISM: herpes simplex

<400> SEQUENCE: 14

Met Phe Cys Ala Ala Gly Gly Pro Thr Ser Pro Gly Gly Lys Ser Ala
1               5                   10                  15

Ala Arg Ala Ala Ser Gly Phe Phe Ala Pro His Asn Pro Arg Gly Ala
                20                  25                  30

Thr Gln Thr Ala Pro Pro Pro Cys Arg Arg Gln Asn Phe Tyr Asn Pro
            35                  40                  45

His Leu Ala Gln Thr Gly Thr Gln Pro Lys Ala Pro Gly Pro Ala Gln
        50                  55                  60

Arg His Thr Tyr Tyr Ser Glu Cys Asp Glu Phe Arg Phe Ile Ala Pro
65                  70                  75                  80

Arg Ser Leu Asp Glu Asp Ala Pro Ala Glu Gln Arg Thr Gly Val His
                85                  90                  95

Asp Gly Arg Leu Arg Arg Ala Pro Lys Val Tyr Cys Gly Gly Asp Glu
            100                 105                 110

Arg Asp Val Leu Arg Val Gly Pro Glu Gly Phe Trp Pro Arg Arg Leu
        115                 120                 125

Arg Leu Trp Gly Gly Ala Asp His Ala Pro Lys Gly Phe Asp Pro Thr
130                 135                 140

Val Thr Val Phe His Val Tyr Asp Ile Leu Glu His Val Glu His Ala
145                 150                 155                 160

Tyr Ser Met Arg Ala Ala Gln Leu His Glu Arg Phe Met Asp Ala Ile
                165                 170                 175

Thr Pro Ala Gly Thr Val Ile Thr Leu Leu Gly Leu Thr Pro Glu Gly
            180                 185                 190

His Arg Val Ala Val His Val Tyr Gly Thr Arg Gln Tyr Phe Tyr Met
        195                 200                 205

Asn Lys Ala Glu Val Asp Arg His Leu Gln Cys Arg Ala Pro Arg Asp
    210                 215                 220

Leu Cys Glu Arg Leu Ala Ala Ala Leu Arg Glu Ser Pro Gly Ala Ser
225                 230                 235                 240

Phe Arg Gly Ile Ser Ala Asp His Phe Glu Ala Glu Val Val Glu Arg
                245                 250                 255

Ala Asp Val Tyr Tyr Glu Thr Arg Pro Thr Leu Tyr Tyr Arg Val
            260                 265                 270

Phe Val Arg Ser Gly Arg Ala Leu Ala Tyr Leu Cys Asp Asn Phe Cys
        275                 280                 285

Pro Ala Ile Arg Lys Tyr Glu Gly Gly Val Asp Ala Thr Thr Arg Phe
    290                 295                 300

Ile Leu Asp Asn Pro Gly Phe Val Thr Phe Gly Trp Tyr Arg Leu Lys
305                 310                 315                 320

Pro Gly Arg Gly Asn Ala Pro Ala Gln Pro Arg Pro Thr Ala Phe
                325                 330                 335
```

-continued

```
Gly Thr Ser Ser Asp Val Glu Phe Asn Cys Thr Ala Asp Asn Leu Ala
            340                 345                 350
Val Glu Gly Ala Met Cys Asp Leu Pro Ala Tyr Lys Leu Met Cys Phe
        355                 360                 365
Asp Ile Glu Cys Lys Ala Gly Gly Asp Glu Leu Ala Phe Pro Val
    370                 375                 380
Ala Glu Arg Pro Glu Asp Leu Val Ile Gln Ile Ser Cys Leu Leu Tyr
385                 390                 395                 400
Asp Leu Ser Thr Thr Ala Leu Glu His Ile Leu Leu Phe Ser Leu Gly
                405                 410                 415
Ser Cys Asp Leu Pro Glu Ser His Leu Ser Asp Leu Ala Ser Arg Gly
            420                 425                 430
Leu Pro Ala Pro Val Val Leu Glu Phe Asp Ser Glu Phe Glu Met Leu
        435                 440                 445
Leu Ala Phe Met Thr Phe Val Lys Gln Tyr Gly Pro Glu Phe Val Thr
    450                 455                 460
Gly Tyr Asn Ile Ile Asn Phe Asp Trp Pro Phe Val Leu Thr Lys Leu
465                 470                 475                 480
Thr Glu Ile Tyr Lys Val Pro Leu Asp Gly Tyr Gly Arg Met Asn Gly
                485                 490                 495
Arg Gly Val Phe Arg Val Trp Asp Ile Gly Gln Ser His Phe Gln Lys
            500                 505                 510
Arg Ser Lys Ile Lys Val Asn Gly Met Val Asn Ile Asp Met Tyr Gly
        515                 520                 525
Ile Ile Thr Asp Lys Val Lys Leu Ser Ser Tyr Lys Leu Asn Ala Val
    530                 535                 540
Ala Glu Ala Val Leu Lys Asp Lys Lys Lys Asp Leu Ser Tyr Arg Asp
545                 550                 555                 560
Ile Pro Ala Tyr Tyr Ala Ser Gly Pro Ala Gln Arg Gly Val Ile Gly
                565                 570                 575
Glu Tyr Cys Val Gln Asp Ser Leu Leu Val Gly Gln Leu Phe Phe Lys
            580                 585                 590
Phe Leu Pro His Leu Glu Leu Ser Ala Val Ala Arg Leu Ala Gly Ile
        595                 600                 605
Asn Ile Thr Arg Thr Ile Tyr Asp Gly Gln Gln Ile Arg Val Phe Thr
    610                 615                 620
Cys Leu Leu Arg Leu Ala Gly Gln Lys Gly Phe Ile Leu Pro Asp Thr
625                 630                 635                 640
Gln Gly Arg Phe Arg Gly Leu Asp Lys Glu Ala Pro Lys Arg Pro Ala
                645                 650                 655
Val Pro Arg Gly Glu Gly Glu Arg Pro Gly Asp Gly Asn Gly Asp Glu
            660                 665                 670
Asp Lys Asp Asp Glu Asp Glu Asp Gly Asp Glu Arg Glu Glu Val
        675                 680                 685
Ala Arg Glu Thr Gly Gly Arg His Val Gly Tyr Gln Gly Ala Arg Val
    690                 695                 700
Leu Asp Pro Thr Ser Gly Phe His Val Asp Pro Val Val Phe Asp
705                 710                 715                 720
Phe Ala Ser Leu Tyr Pro Ser Ile Ile Gln Ala His Asn Leu Cys Phe
                725                 730                 735
Ser Thr Leu Ser Leu Arg Pro Glu Ala Val Ala His Leu Glu Ala Asp
            740                 745                 750
Arg Asp Tyr Leu Glu Ile Glu Val Gly Gly Arg Arg Leu Phe Phe Val
```

-continued

```
            755                 760                 765
Lys Ala His Val Arg Glu Ser Leu Leu Ser Ile Leu Leu Arg Asp Trp
    770                 775                 780
Leu Ala Met Arg Lys Gln Ile Arg Ser Arg Ile Pro Gln Ser Thr Pro
785                 790                 795                 800
Glu Glu Ala Val Leu Leu Asp Lys Gln Gln Ala Ala Ile Lys Val Val
                    805                 810                 815
Cys Asn Ser Val Tyr Gly Phe Thr Gly Val Gln His Gly Leu Leu Pro
                820                 825                 830
Cys Leu His Val Ala Ala Thr Val Thr Thr Ile Gly Arg Glu Met Leu
                835                 840                 845
Leu Ala Thr Arg Ala Tyr Val His Ala Arg Trp Ala Glu Phe Asp Gln
850                 855                 860
Leu Leu Ala Asp Phe Pro Glu Ala Ala Gly Met Arg Ala Pro Gly Pro
865                 870                 875                 880
Tyr Ser Met Arg Ile Ile Tyr Gly Asp Thr Asp Ser Ile Phe Val Leu
                885                 890                 895
Cys Arg Gly Leu Thr Ala Ala Gly Leu Val Ala Met Gly Asp Lys Met
                900                 905                 910
Ala Ser His Ile Ser Arg Ala Leu Phe Leu Pro Pro Ile Lys Leu Glu
                915                 920                 925
Cys Glu Lys Thr Phe Thr Lys Leu Leu Leu Ile Ala Lys Lys Lys Tyr
            930                 935                 940
Ile Gly Val Ile Cys Gly Gly Lys Met Leu Ile Lys Gly Val Asp Leu
945                 950                 955                 960
Val Arg Lys Asn Asn Cys Ala Phe Ile Asn Arg Thr Ser Arg Ala Leu
                965                 970                 975
Val Asp Leu Leu Phe Tyr Asp Asp Thr Val Ser Gly Ala Ala Ala Ala
                980                 985                 990
Leu Ala Glu Arg Pro Ala Glu Glu  Trp Leu Ala Arg Pro Leu Pro Glu
            995                 1000                1005
Gly Leu  Gln Ala Phe Gly Ala  Val Leu Val Asp Ala  His Arg Arg
            1010                1015                1020
Ile Thr  Asp Pro Glu Arg Asp  Ile Gln Asp Phe Val  Leu Thr Ala
            1025                1030                1035
Glu Leu  Ser Arg His Pro Arg  Ala Tyr Thr Asn Lys  Arg Leu Ala
            1040                1045                1050
His Leu  Thr Val Tyr Tyr Lys  Leu Met Ala Arg Arg  Ala Gln Val
            1055                1060                1065
Pro Ser  Ile Lys Asp Arg Ile  Pro Tyr Val Ile Val  Ala Gln Thr
            1070                1075                1080
Arg Glu  Val Glu Glu Thr Val  Ala Arg Leu Ala Ala  Leu Arg Glu
            1085                1090                1095
Leu Asp  Ala Ala Ala Pro Gly  Asp Glu Pro Ala Pro  Pro Ala Ala
            1100                1105                1110
Leu Pro  Ser Pro Ala Lys Arg  Pro Arg Glu Thr Pro  Ser His Ala
            1115                1120                1125
Asp Pro  Pro Gly Gly Ala Ser  Lys Pro Arg Lys Leu  Leu Val Ser
            1130                1135                1140
Glu Leu  Ala Glu Asp Pro Gly  Tyr Ala Ile Ala Arg  Gly Val Pro
            1145                1150                1155
Leu Asn  Thr Asp Tyr Tyr Phe  Ser His Leu Leu Gly  Ala Ala Cys
            1160                1165                1170
```

```
Val Thr Phe Lys Ala Leu Phe Gly Asn Asn Ala Lys Ile Thr Glu
    1175                1180                1185

Ser Leu Leu Lys Arg Phe Ile Pro Glu Thr Trp His Pro Pro Asp
    1190                1195                1200

Asp Val Ala Ala Arg Leu Arg Ala Ala Gly Phe Gly Pro Ala Gly
    1205                1210                1215

Ala Gly Ala Thr Ala Glu Glu Thr Arg Arg Met Leu His Arg Ala
    1220                1225                1230

Phe Asp Thr Leu Ala
    1235

<210> SEQ ID NO 15
<211> LENGTH: 1240
<212> TYPE: PRT
<213> ORGANISM: herpes simplex

<400> SEQUENCE: 15

Met Phe Cys Ala Ala Gly Gly Pro Ala Ser Pro Gly Gly Lys Ser Ala
1               5                   10                  15

Ala Arg Ala Ala Ser Gly Phe Ala Pro His Asn Pro Arg Gly Ala
                20                  25                  30

Thr Gln Thr Ala Pro Pro Cys Arg Arg Gln Asn Phe Tyr Asn Pro
            35                  40                  45

His Leu Ala Gln Thr Gly Thr Gln Pro Lys Ala Gly Pro Ala Gln
    50                  55                  60

Arg His Thr Tyr Tyr Ser Glu Cys Asp Glu Phe Arg Phe Ile Ala Pro
65                  70                  75                  80

Arg Ser Leu Asp Glu Asp Ala Pro Ala Glu Gln Arg Thr Gly Val His
                85                  90                  95

Asp Gly Arg Leu Arg Arg Ala Pro Lys Val Tyr Cys Gly Gly Asp Glu
                100                 105                 110

Arg Asp Val Leu Arg Val Gly Pro Glu Gly Phe Trp Pro Arg Arg Leu
            115                 120                 125

Arg Leu Trp Gly Gly Ala Asp His Ala Pro Glu Gly Phe Asp Pro Thr
    130                 135                 140

Val Thr Val Phe His Val Tyr Asp Ile Leu Glu His Val Glu His Ala
145                 150                 155                 160

Tyr Ser Met Arg Ala Ala Gln Leu His Glu Arg Phe Met Asp Ala Ile
                165                 170                 175

Thr Pro Ala Gly Thr Val Ile Thr Leu Leu Gly Leu Thr Pro Glu Gly
                180                 185                 190

His Arg Val Ala Val His Val Tyr Gly Thr Arg Gln Tyr Phe Tyr Met
            195                 200                 205

Asn Lys Ala Glu Val Asp Arg His Leu Gln Cys Arg Ala Pro Arg Asp
    210                 215                 220

Leu Cys Glu Arg Leu Ala Ala Leu Arg Glu Ser Pro Gly Ala Ser
225                 230                 235                 240

Phe Arg Gly Ile Ser Ala Asp His Phe Glu Ala Glu Val Glu Arg
                245                 250                 255

Ala Asp Val Tyr Tyr Tyr Glu Thr Arg Pro Thr Leu Tyr Tyr Arg Val
                260                 265                 270

Phe Val Arg Ser Gly Arg Ala Leu Ala Tyr Leu Cys Asp Asn Phe Cys
            275                 280                 285

Pro Ala Ile Arg Lys Tyr Glu Gly Gly Val Asp Ala Thr Thr Arg Phe
```

```
                    290                 295                 300

Ile Leu Asp Asn Pro Gly Phe Val Thr Phe Gly Trp Tyr Arg Leu Lys
305                 310                 315                 320

Pro Gly Arg Gly Asn Ala Pro Ala Gln Pro Arg Pro Thr Ala Phe
                    325                 330                 335

Gly Thr Ser Ser Asp Val Glu Phe Asn Cys Thr Ala Asp Asn Leu Ala
                    340                 345                 350

Val Glu Gly Ala Met Cys Asp Leu Pro Ala Tyr Lys Leu Met Cys Phe
                    355                 360                 365

Asp Ile Glu Cys Lys Ala Gly Glu Asp Glu Leu Ala Phe Pro Val
    370                 375                 380

Ala Glu Arg Pro Glu Asp Leu Val Ile Gln Ile Ser Cys Leu Leu Tyr
385                 390                 395                 400

Asp Leu Ser Thr Thr Ala Leu Glu His Ile Leu Leu Phe Ser Leu Gly
                    405                 410                 415

Ser Cys Asp Leu Pro Glu Ser His Leu Ser Asp Leu Ala Ser Arg Gly
                    420                 425                 430

Leu Pro Ala Pro Val Val Leu Glu Phe Asp Ser Glu Phe Glu Met Leu
                    435                 440                 445

Leu Ala Phe Met Thr Phe Val Lys Gln Tyr Gly Pro Glu Phe Val Thr
                    450                 455                 460

Gly Tyr Asn Ile Ile Asn Phe Asp Trp Pro Phe Val Leu Thr Lys Leu
465                 470                 475                 480

Thr Glu Ile Tyr Lys Val Pro Leu Asp Gly Tyr Gly Arg Met Asn Gly
                    485                 490                 495

Arg Gly Val Phe Arg Val Trp Asp Ile Gly Gln Ser His Phe Gln Lys
                    500                 505                 510

Arg Ser Lys Ile Lys Val Asn Gly Met Val Asn Ile Asp Met Tyr Gly
                    515                 520                 525

Ile Ile Thr Asp Lys Val Lys Leu Ser Ser Tyr Lys Leu Asn Ala Val
                    530                 535                 540

Ala Glu Ala Val Leu Lys Asp Lys Lys Asp Leu Ser Tyr Arg Asp
545                 550                 555                 560

Ile Pro Ala Tyr Tyr Ala Ser Gly Pro Ala Gln Arg Gly Val Ile Gly
                    565                 570                 575

Glu Tyr Cys Val Gln Asp Ser Leu Leu Val Gly Gln Leu Phe Phe Lys
                    580                 585                 590

Phe Leu Pro His Leu Glu Leu Ser Ala Val Ala Arg Leu Ala Gly Ile
                    595                 600                 605

Asn Ile Thr Arg Thr Ile Tyr Asp Gly Gln Gln Ile Arg Val Phe Thr
                    610                 615                 620

Cys Leu Leu Arg Leu Ala Gly Gln Lys Gly Phe Ile Leu Pro Asp Thr
625                 630                 635                 640

Gln Gly Arg Phe Arg Gly Leu Asp Lys Glu Ala Pro Lys Arg Pro Ala
                    645                 650                 655

Val Pro Arg Gly Glu Gly Glu Arg Pro Gly Asp Gly Asn Gly Asp Glu
                    660                 665                 670

Asp Lys Asp Asp Asp Glu Asp Gly Asp Glu Asp Gly Asp Glu Arg Glu
                    675                 680                 685

Glu Val Ala Arg Glu Thr Gly Gly Arg His Val Gly Tyr Gln Gly Ala
                    690                 695                 700

Arg Val Leu Asp Pro Thr Ser Gly Phe His Val Asp Pro Val Val Val
705                 710                 715                 720
```

-continued

Phe Asp Phe Ala Ser Leu Tyr Pro Ser Ile Ile Gln Ala His Asn Leu
              725                 730                 735

Cys Phe Ser Thr Leu Ser Leu Arg Pro Glu Ala Val Ala His Leu Glu
              740                 745                 750

Ala Asp Arg Asp Tyr Leu Glu Ile Glu Val Gly Gly Arg Arg Leu Phe
              755                 760                 765

Phe Val Lys Ala His Val Arg Glu Ser Leu Leu Ser Ile Leu Leu Arg
    770                 775                 780

Asp Trp Leu Ala Met Arg Lys Gln Ile Arg Ser Arg Ile Pro Gln Ser
785                 790                 795                 800

Pro Pro Glu Glu Ala Val Leu Leu Asp Lys Gln Gln Ala Ala Ile Lys
              805                 810                 815

Val Val Cys Asn Ser Val Tyr Gly Phe Thr Gly Val Gln His Gly Leu
              820                 825                 830

Leu Pro Cys Leu His Val Ala Ala Thr Val Thr Ile Gly Arg Glu
              835                 840                 845

Met Leu Leu Ala Thr Arg Ala Tyr Val His Ala Arg Trp Ala Glu Phe
    850                 855                 860

Asp Gln Leu Leu Ala Asp Phe Pro Glu Ala Ala Gly Met Arg Ala Pro
865                 870                 875                 880

Gly Pro Tyr Ser Met Arg Ile Ile Tyr Gly Asp Thr Asp Ser Ile Phe
              885                 890                 895

Val Leu Cys Arg Gly Leu Thr Ala Ala Gly Leu Val Ala Met Gly Asp
              900                 905                 910

Lys Met Ala Ser His Ile Ser Arg Ala Leu Phe Leu Pro Pro Ile Lys
              915                 920                 925

Leu Glu Cys Glu Lys Thr Phe Thr Lys Leu Leu Leu Ile Ala Lys Lys
    930                 935                 940

Lys Tyr Ile Gly Val Ile Cys Gly Gly Lys Met Leu Ile Lys Gly Val
945                 950                 955                 960

Asp Leu Val Arg Lys Asn Asn Cys Ala Phe Ile Asn Arg Thr Ser Arg
              965                 970                 975

Ala Leu Val Asp Leu Leu Phe Tyr Asp Asp Thr Val Ser Gly Ala Ala
              980                 985                 990

Ala Ala Leu Ala Glu Arg Pro Ala Glu Glu Trp Leu Ala Arg Pro Leu
    995                 1000                1005

Pro Glu Gly Leu Gln Ala Phe Gly Ala Val Leu Val Asp Ala His
    1010                1015                1020

Arg Arg Ile Thr Asp Pro Glu Arg Asp Ile Gln Asp Phe Val Leu
    1025                1030                1035

Thr Ala Glu Leu Ser Arg His Pro Arg Ala Tyr Thr Asn Lys Arg
    1040                1045                1050

Leu Ala His Leu Thr Val Tyr Tyr Lys Leu Met Ala Arg Arg Ala
    1055                1060                1065

Gln Val Pro Ser Ile Lys Asp Arg Ile Pro Tyr Val Ile Val Ala
    1070                1075                1080

Gln Thr Arg Glu Val Glu Glu Thr Val Ala Arg Leu Ala Ala Leu
    1085                1090                1095

Arg Glu Leu Asp Ala Ala Ala Pro Gly Asp Glu Pro Ala Pro Pro
    1100                1105                1110

Ala Ala Leu Pro Ser Pro Ala Lys Arg Pro Arg Glu Thr Pro Ser
    1115                1120                1125

```
His Ala Asp Pro Pro Gly Gly Ala Ser Lys Pro Arg Lys Leu Leu
    1130                1135                1140

Val Ser Glu Leu Ala Glu Asp Pro Gly Tyr Ala Ile Ala Arg Gly
    1145                1150                1155

Val Pro Leu Asn Thr Asp Tyr Tyr Phe Ser His Leu Leu Gly Ala
    1160                1165                1170

Ala Cys Val Thr Phe Lys Ala Leu Phe Gly Asn Asn Ala Lys Ile
    1175                1180                1185

Thr Glu Ser Leu Leu Lys Arg Phe Ile Pro Glu Thr Trp His Pro
    1190                1195                1200

Pro Asp Asp Val Ala Ala Arg Leu Arg Ala Ala Gly Phe Gly Pro
    1205                1210                1215

Ala Gly Ala Gly Ala Thr Ala Glu Glu Thr Arg Arg Met Leu His
    1220                1225                1230

Arg Ala Phe Asp Thr Leu Ala
    1235                1240

<210> SEQ ID NO 16
<211> LENGTH: 1235
<212> TYPE: PRT
<213> ORGANISM: herpes simplex

<400> SEQUENCE: 16

Met Phe Ser Gly Gly Gly Gly Pro Leu Ser Pro Gly Gly Lys Ser Ala
1               5                   10                  15

Ala Arg Ala Ala Ser Gly Phe Phe Ala Pro Ala Gly Pro Arg Gly Ala
            20                  25                  30

Gly Arg Gly Pro Pro Pro Cys Leu Arg Gln Asn Phe Tyr Asn Pro Tyr
        35                  40                  45

Leu Ala Pro Val Gly Thr Gln Gln Lys Pro Thr Gly Pro Thr Gln Arg
    50                  55                  60

His Thr Tyr Tyr Ser Glu Cys Asp Glu Phe Arg Phe Ile Ala Pro Arg
65                  70                  75                  80

Val Leu Asp Glu Asp Ala Pro Pro Glu Lys Arg Ala Gly Val His Asp
                85                  90                  95

Gly His Leu Lys Arg Ala Pro Lys Val Tyr Cys Gly Gly Asp Glu Arg
            100                 105                 110

Asp Val Leu Arg Val Gly Ser Gly Gly Phe Trp Pro Arg Arg Ser Arg
        115                 120                 125

Leu Trp Gly Gly Val Asp His Ala Pro Ala Gly Phe Asn Pro Thr Val
    130                 135                 140

Thr Val Phe His Val Tyr Asp Ile Leu Glu Asn Val Glu His Ala Tyr
145                 150                 155                 160

Gly Met Arg Ala Ala Gln Phe His Ala Arg Phe Met Asp Ala Ile Thr
                165                 170                 175

Pro Thr Gly Thr Val Ile Thr Leu Leu Gly Leu Thr Pro Glu Gly His
            180                 185                 190

Arg Val Ala Val His Val Tyr Gly Thr Arg Gln Tyr Phe Tyr Met Asn
        195                 200                 205

Lys Glu Glu Val Asp Arg His Leu Gln Cys Arg Ala Pro Arg Asp Leu
    210                 215                 220

Cys Glu Arg Met Ala Ala Ala Leu Arg Glu Ser Pro Gly Ala Ser Phe
225                 230                 235                 240

Arg Gly Ile Ser Ala Asp His Phe Glu Ala Glu Val Val Glu Arg Thr
                245                 250                 255
```

-continued

```
Asp Val Tyr Tyr Tyr Glu Thr Arg Pro Ala Leu Phe Tyr Arg Val Tyr
            260                 265                 270

Val Arg Ser Gly Arg Val Leu Ser Tyr Leu Cys Asp Asn Phe Cys Pro
            275                 280                 285

Ala Ile Lys Lys Tyr Glu Gly Val Asp Ala Thr Thr Arg Phe Ile
290                 295                 300

Leu Asp Asn Pro Gly Phe Val Thr Phe Gly Trp Tyr Arg Leu Lys Pro
305                 310                 315                 320

Gly Arg Asn Asn Thr Leu Ala Gln Pro Arg Ala Pro Met Ala Phe Gly
                325                 330                 335

Thr Ser Ser Asp Val Glu Phe Asn Cys Thr Ala Asp Asn Leu Ala Ile
                340                 345                 350

Glu Gly Gly Met Ser Asp Leu Pro Ala Tyr Lys Leu Met Cys Phe Asp
            355                 360                 365

Ile Glu Cys Lys Ala Gly Gly Glu Asp Glu Leu Ala Phe Pro Val Ala
            370                 375                 380

Gly His Pro Glu Asp Leu Val Ile Gln Ile Ser Cys Leu Leu Tyr Asp
385                 390                 395                 400

Leu Ser Thr Thr Ala Leu Glu His Val Leu Leu Phe Ser Leu Gly Ser
                405                 410                 415

Cys Asp Leu Pro Glu Ser His Leu Asn Glu Leu Ala Ala Arg Gly Leu
                420                 425                 430

Pro Thr Pro Val Val Leu Glu Phe Asp Ser Gly Phe Glu Met Leu Leu
            435                 440                 445

Ala Phe Met Thr Leu Val Lys Gln Tyr Gly Pro Glu Phe Val Thr Gly
            450                 455                 460

Tyr Asn Ile Ile Asn Phe Asp Trp Pro Phe Leu Leu Ala Lys Leu Thr
465                 470                 475                 480

Asp Ile Tyr Lys Val Pro Leu Asp Gly Tyr Gly Arg Met Asn Gly Arg
                485                 490                 495

Gly Val Phe Arg Val Trp Asp Ile Gly Gln Ser His Phe Gln Lys Arg
            500                 505                 510

Ser Lys Ile Lys Val Asn Gly Met Val Asn Ile Asp Met Tyr Gly Ile
            515                 520                 525

Ile Thr Asp Lys Ile Lys Leu Ser Ser Tyr Lys Leu Asn Ala Val Ala
530                 535                 540

Glu Ala Val Leu Lys Asp Lys Lys Lys Asp Leu Ser Tyr Arg Asp Ile
545                 550                 555                 560

Pro Ala Tyr Tyr Ala Ala Gly Pro Ala Gln Arg Gly Val Ile Gly Glu
                565                 570                 575

Tyr Cys Ile Gln Asp Ser Leu Leu Val Gly Gln Leu Phe Phe Lys Phe
                580                 585                 590

Leu Pro His Leu Glu Leu Ser Ala Val Ala Arg Leu Ala Gly Ile Asn
            595                 600                 605

Ile Thr Arg Thr Ile Tyr Asp Gly Gln Gln Ile Arg Val Phe Thr Cys
            610                 615                 620

Leu Leu Arg Leu Ala Asp Gln Lys Gly Phe Ile Leu Pro Asp Thr Gln
625                 630                 635                 640

Gly Arg Phe Arg Gly Ala Gly Gly Glu Ala Pro Lys Arg Pro Ala Ala
                645                 650                 655

Ala Arg Glu Asp Glu Glu Arg Pro Glu Glu Glu Gly Glu Asp Glu Asp
                660                 665                 670
```

```
Glu Arg Glu Glu Gly Gly Gly Glu Arg Glu Pro Glu Gly Ala Arg Glu
            675                 680                 685

Thr Ala Gly Arg His Val Gly Tyr Gln Gly Ala Arg Val Leu Asp Pro
        690                 695                 700

Thr Ser Gly Phe His Val Asn Pro Val Val Phe Asp Phe Ala Ser
705                 710                 715                 720

Leu Tyr Pro Ser Ile Ile Gln Ala His Asn Leu Cys Phe Ser Thr Leu
                725                 730                 735

Ser Leu Arg Ala Asp Ala Val Ala His Leu Glu Ala Gly Lys Asp Tyr
            740                 745                 750

Leu Glu Ile Glu Val Gly Gly Arg Arg Leu Phe Phe Val Lys Ala His
            755                 760                 765

Val Arg Glu Ser Leu Leu Ser Ile Leu Leu Arg Asp Trp Leu Ala Met
        770                 775                 780

Arg Lys Gln Ile Arg Ser Arg Ile Pro Gln Ser Ser Pro Glu Ala
785                 790                 795                 800

Val Leu Leu Asp Lys Gln Gln Ala Ala Ile Lys Val Val Cys Asn Ser
                805                 810                 815

Val Tyr Gly Phe Thr Gly Val Gln His Gly Leu Leu Pro Cys Leu His
            820                 825                 830

Val Ala Ala Thr Val Thr Thr Ile Gly Arg Glu Met Leu Leu Ala Thr
            835                 840                 845

Arg Glu Tyr Val His Ala Arg Trp Ala Ala Phe Glu Gln Leu Leu Ala
    850                 855                 860

Asp Phe Pro Glu Ala Ala Asp Met Arg Ala Pro Gly Pro Tyr Ser Met
865                 870                 875                 880

Arg Ile Ile Tyr Gly Asp Thr Asp Ser Ile Phe Val Leu Cys Arg Gly
                885                 890                 895

Leu Thr Ala Ala Gly Leu Thr Ala Met Gly Asp Lys Met Ala Ser His
            900                 905                 910

Ile Ser Arg Ala Leu Phe Leu Pro Pro Ile Lys Leu Glu Cys Glu Lys
        915                 920                 925

Thr Phe Thr Lys Leu Leu Leu Ile Ala Lys Lys Lys Tyr Ile Gly Val
        930                 935                 940

Ile Tyr Gly Gly Lys Met Leu Ile Lys Gly Val Asp Leu Val Arg Lys
945                 950                 955                 960

Asn Asn Cys Ala Phe Ile Asn Arg Thr Ser Arg Ala Leu Val Asp Leu
                965                 970                 975

Leu Phe Tyr Asp Asp Thr Val Ser Gly Ala Ala Ala Leu Ala Glu
            980                 985                 990

Arg Pro Ala Glu Glu Trp Leu Ala Arg Pro Leu Pro Glu Gly Leu Gln
        995                 1000                1005

Ala Phe Gly Ala Val Leu Val Asp Ala His Arg Arg Ile Thr Asp
        1010                1015                1020

Pro Glu Arg Asp Ile Gln Asp Phe Val Leu Thr Ala Glu Leu Ser
    1025                1030                1035

Arg His Pro Arg Ala Tyr Thr Asn Lys Arg Leu Ala His Leu Thr
    1040                1045                1050

Val Tyr Tyr Lys Leu Met Ala Arg Arg Ala Gln Val Pro Ser Ile
    1055                1060                1065

Lys Asp Arg Ile Pro Tyr Val Ile Val Ala Gln Thr Arg Glu Val
    1070                1075                1080

Glu Glu Thr Val Ala Arg Leu Ala Ala Leu Arg Glu Leu Asp Ala
```

-continued

```
            1085                1090                1095

Ala Ala Pro Gly Asp Glu Pro Ala Pro Ala Leu Pro Ser
    1100                1105                1110

Pro Ala Lys Arg Pro Arg Glu Thr Pro Ser His Ala Asp Pro Pro
    1115                1120                1125

Gly Gly Ala Ser Lys Pro Arg Lys Leu Leu Val Ser Glu Leu Ala
    1130                1135                1140

Glu Asp Pro Ala Tyr Ala Ile Ala His Gly Val Ala Leu Asn Thr
    1145                1150                1155

Asp Tyr Tyr Phe Ser His Leu Leu Gly Ala Ala Cys Val Thr Phe
    1160                1165                1170

Lys Ala Leu Phe Gly Asn Asn Ala Lys Ile Thr Glu Ser Leu Leu
    1175                1180                1185

Lys Arg Phe Ile Pro Glu Val Trp His Pro Pro Asp Val Ala
    1190                1195                1200

Ala Arg Leu Arg Ala Ala Gly Phe Gly Ala Val Gly Ala Gly Ala
    1205                1210                1215

Thr Ala Glu Glu Thr Arg Arg Met Leu His Arg Ala Phe Asp Thr
    1220                1225                1230

Leu Ala
    1235

<210> SEQ ID NO 17
<211> LENGTH: 1235
<212> TYPE: PRT
<213> ORGANISM: herpes simplex

<400> SEQUENCE: 17

Met Phe Ser Gly Gly Gly Gly Pro Leu Ser Pro Gly Gly Lys Ser Ala
1               5                   10                  15

Ala Arg Ala Ala Ser Gly Phe Phe Ala Pro Ala Gly Pro Arg Gly Ala
            20                  25                  30

Gly Arg Gly Pro Pro Pro Cys Leu Arg Gln Asn Phe Tyr Asn Pro Tyr
        35                  40                  45

Leu Ala Pro Val Gly Thr Gln Gln Lys Pro Thr Gly Pro Thr Gln Arg
    50                  55                  60

His Thr Tyr Tyr Ser Glu Cys Asp Glu Phe Arg Phe Ile Ala Pro Arg
65                  70                  75                  80

Val Leu Asp Glu Asp Ala Pro Pro Glu Lys Arg Ala Gly Val His Asp
                85                  90                  95

Gly His Leu Lys Arg Ala Pro Lys Val Tyr Cys Gly Gly Asp Glu Arg
            100                 105                 110

Asp Val Leu Arg Val Gly Ser Gly Gly Phe Trp Pro Arg Arg Ser Arg
        115                 120                 125

Leu Trp Gly Gly Val Asp His Ala Pro Ala Gly Phe Asn Pro Thr Val
    130                 135                 140

Thr Val Phe His Val Tyr Asp Ile Leu Glu Asn Val Glu His Ala Tyr
145                 150                 155                 160

Gly Met Arg Ala Ala Gln Phe His Ala Arg Phe Met Asp Ala Ile Thr
                165                 170                 175

Pro Thr Gly Thr Val Ile Thr Leu Leu Gly Leu Thr Pro Glu Gly His
            180                 185                 190

Arg Val Ala Val His Val Tyr Gly Thr Arg Gln Tyr Phe Tyr Met Asn
        195                 200                 205
```

-continued

```
Lys Glu Glu Val Asp Arg His Leu Gln Cys Arg Ala Pro Arg Asp Leu
    210                 215                 220

Cys Glu Arg Met Ala Ala Leu Arg Glu Ser Pro Gly Ala Ser Phe
225                 230                 235                 240

Arg Gly Ile Ser Ala Asp His Phe Glu Ala Glu Val Val Glu Arg Thr
                245                 250                 255

Asp Val Tyr Tyr Tyr Glu Thr Arg Pro Ala Leu Phe Tyr Arg Val Tyr
            260                 265                 270

Val Arg Ser Gly Arg Val Leu Ser Tyr Leu Cys Asp Asn Phe Cys Pro
        275                 280                 285

Ala Ile Lys Lys Tyr Glu Gly Gly Val Asp Ala Thr Thr Arg Phe Ile
    290                 295                 300

Leu Asp Asn Pro Gly Phe Val Thr Phe Gly Trp Tyr Arg Leu Lys Pro
305                 310                 315                 320

Gly Arg Asn Asn Thr Leu Ala Gln Pro Arg Ala Pro Met Ala Phe Gly
                325                 330                 335

Thr Ser Ser Asp Val Glu Phe Asn Cys Thr Ala Asp Asn Leu Ala Ile
            340                 345                 350

Glu Gly Gly Met Ser Asp Leu Pro Ala Tyr Lys Leu Met Cys Phe Asp
        355                 360                 365

Ile Glu Cys Lys Ala Gly Gly Glu Asp Glu Leu Ala Phe Pro Val Ala
    370                 375                 380

Gly His Pro Glu Asp Leu Val Ile Gln Ile Ser Cys Leu Leu Tyr Asp
385                 390                 395                 400

Leu Ser Thr Thr Ala Leu Glu His Val Leu Leu Phe Ser Leu Gly Ser
                405                 410                 415

Cys Asp Leu Pro Glu Ser His Leu Asn Glu Leu Ala Ala Arg Gly Leu
            420                 425                 430

Pro Thr Pro Val Val Leu Glu Phe Asp Ser Glu Phe Glu Met Leu Leu
        435                 440                 445

Ala Phe Met Thr Leu Val Lys Gln Tyr Gly Pro Glu Phe Val Thr Gly
    450                 455                 460

Tyr Asn Ile Ile Asn Phe Asp Trp Pro Phe Leu Leu Ala Lys Leu Thr
465                 470                 475                 480

Asp Ile Tyr Lys Val Pro Leu Asp Gly Tyr Gly Arg Met Asn Gly Arg
                485                 490                 495

Gly Val Phe Arg Val Trp Asp Ile Gly Gln Ser His Phe Gln Lys Arg
            500                 505                 510

Ser Lys Ile Lys Val Asn Gly Met Val Asn Ile Asp Met Tyr Gly Ile
        515                 520                 525

Ile Thr Asp Lys Ile Lys Leu Ser Ser Tyr Lys Leu Asn Ala Val Ala
    530                 535                 540

Glu Ala Val Leu Lys Asp Lys Lys Asp Leu Ser Tyr Arg Asp Ile
545                 550                 555                 560

Pro Ala Tyr Tyr Ala Ala Gly Pro Ala Gln Arg Gly Val Ile Gly Glu
                565                 570                 575

Tyr Cys Ile Gln Asp Ser Leu Leu Val Gly Gln Leu Phe Phe Lys Phe
            580                 585                 590

Leu Pro His Leu Glu Leu Ser Ala Val Ala Arg Leu Ala Gly Ile Asn
        595                 600                 605

Ile Thr Arg Thr Ile Tyr Asp Gly Gln Gln Ile Arg Val Phe Thr Cys
    610                 615                 620

Leu Leu Arg Leu Ala Asp Gln Lys Gly Phe Ile Leu Pro Asp Thr Gln
```

```
                625                 630                 635                 640
Gly Arg Phe Arg Gly Ala Gly Glu Ala Pro Lys Arg Pro Ala Ala
            645                 650                 655
Ala Arg Glu Asp Glu Glu Arg Pro Glu Glu Gly Glu Asp Glu Asp
            660                 665                 670
Glu Arg Glu Glu Gly Gly Gly Glu Arg Glu Pro Glu Gly Ala Arg Glu
            675                 680                 685
Thr Ala Gly Arg His Val Gly Tyr Gln Gly Ala Arg Val Leu Asp Pro
            690                 695                 700
Ile Ser Gly Phe His Val Asn Pro Val Val Val Phe Asp Phe Ala Ser
705                 710                 715                 720
Leu Tyr Pro Ser Ile Ile Gln Ala His Asn Leu Cys Phe Ser Thr Leu
            725                 730                 735
Ser Leu Arg Ala Asp Ala Val Ala His Leu Glu Ala Gly Lys Asp Tyr
            740                 745                 750
Leu Glu Ile Glu Val Gly Gly Arg Arg Leu Phe Phe Val Lys Ala His
            755                 760                 765
Val Arg Glu Ser Leu Leu Ser Ile Leu Leu Arg Asp Trp Leu Ala Met
770                 775                 780
Arg Lys Gln Ile Arg Ser Arg Ile Pro Gln Ser Ser Pro Glu Ala
785                 790                 795                 800
Val Leu Leu Asp Lys Gln Gln Ala Ala Ile Lys Val Val Cys Asn Ser
            805                 810                 815
Val Tyr Gly Phe Thr Gly Val Gln His Gly Leu Leu Pro Cys Leu His
            820                 825                 830
Val Ala Ala Thr Val Thr Thr Ile Gly Arg Glu Met Leu Leu Ala Thr
            835                 840                 845
Arg Glu Tyr Val His Ala Arg Trp Ala Ala Phe Glu Gln Leu Leu Ala
            850                 855                 860
Asp Phe Pro Glu Ala Ala Asp Met Arg Ala Pro Gly Pro Tyr Ser Met
865                 870                 875                 880
Arg Ile Ile Tyr Gly Asp Thr Asp Ser Ile Phe Val Leu Cys Arg Gly
            885                 890                 895
Leu Thr Ala Ala Gly Leu Thr Ala Met Gly Asp Lys Met Ala Ser His
            900                 905                 910
Ile Ser Arg Ala Leu Phe Leu Pro Pro Ile Lys Leu Glu Cys Glu Lys
            915                 920                 925
Thr Phe Thr Lys Leu Leu Leu Ile Ala Lys Lys Lys Tyr Ile Gly Val
            930                 935                 940
Ile Tyr Gly Gly Lys Met Leu Ile Lys Gly Val Asp Leu Val Arg Lys
945                 950                 955                 960
Asn Asn Cys Ala Phe Ile Asn Arg Thr Ser Arg Ala Leu Val Asp Leu
            965                 970                 975
Leu Phe Tyr Asp Asp Thr Val Ser Gly Ala Ala Ala Leu Ala Glu
            980                 985                 990
Arg Pro Ala Glu Glu Trp Leu Ala Arg Pro Leu Pro Glu Gly Leu Gln
            995                 1000                1005
Ala Phe Gly Ala Val Leu Val Asp Ala His Arg Arg Ile Thr Asp
            1010                1015                1020
Pro Glu Arg Asp Ile Gln Asp Phe Val Leu Thr Ala Glu Leu Ser
            1025                1030                1035
Arg His Pro Arg Ala Tyr Thr Asn Lys Arg Leu Ala His Leu Thr
            1040                1045                1050
```

-continued

```
Val Tyr Tyr Lys Leu Met Ala Arg Arg Ala Gln Val Pro Ser Ile
    1055                1060                1065

Lys Asp Arg Ile Pro Tyr Val Ile Val Ala Gln Thr Arg Glu Val
    1070                1075                1080

Glu Glu Thr Val Ala Arg Leu Ala Ala Leu Arg Glu Leu Asp Ala
    1085                1090                1095

Ala Ala Pro Gly Asp Glu Pro Ala Pro Pro Ala Ala Leu Pro Ser
    1100                1105                1110

Pro Ala Lys Arg Pro Arg Glu Thr Pro Ser Pro Ala Asp Pro Pro
    1115                1120                1125

Gly Gly Ala Ser Lys Pro Arg Lys Leu Leu Val Ser Glu Leu Ala
    1130                1135                1140

Glu Asp Pro Ala Tyr Ala Ile Ala His Gly Val Ala Leu Asn Thr
    1145                1150                1155

Asp Tyr Tyr Phe Ser His Leu Leu Gly Ala Ala Cys Val Thr Phe
    1160                1165                1170

Lys Ala Leu Phe Gly Asn Asn Ala Lys Ile Thr Glu Ser Leu Leu
    1175                1180                1185

Lys Arg Phe Ile Pro Glu Val Trp His Pro Pro Asp Asp Val Thr
    1190                1195                1200

Ala Arg Leu Arg Ala Ala Gly Phe Gly Ala Val Gly Ala Gly Ala
    1205                1210                1215

Thr Ala Glu Glu Thr Arg Arg Met Leu His Arg Ala Phe Asp Thr
    1220                1225                1230

Leu Ala
    1235

<210> SEQ ID NO 18
<211> LENGTH: 1235
<212> TYPE: PRT
<213> ORGANISM: herpes simplex

<400> SEQUENCE: 18

Met Phe Ser Gly Gly Gly Gly Pro Leu Ser Pro Gly Gly Lys Ser Ala
1               5                   10                  15

Ala Arg Ala Ala Ser Gly Phe Phe Ala Pro Ala Gly Pro Arg Gly Ala
                20                  25                  30

Gly Arg Gly Pro Pro Pro Cys Leu Arg Gln Asn Phe Tyr Asn Pro Tyr
            35                  40                  45

Leu Ala Pro Val Gly Thr Gln Gln Lys Pro Thr Gly Pro Thr Gln Arg
        50                  55                  60

His Thr Tyr Tyr Ser Glu Cys Asp Glu Phe Arg Phe Ile Ala Pro Arg
65                  70                  75                  80

Val Leu Asp Glu Asp Ala Pro Pro Glu Lys Arg Ala Gly Val His Asp
                85                  90                  95

Gly His Leu Lys Arg Ala Pro Lys Val Tyr Cys Gly Gly Asp Glu Arg
            100                 105                 110

Asp Val Leu Arg Val Gly Ser Gly Gly Phe Trp Pro Arg Arg Ser Arg
        115                 120                 125

Leu Trp Gly Gly Val Asp His Ala Pro Ala Gly Phe Asn Pro Thr Val
    130                 135                 140

Thr Val Phe His Val Tyr Asp Ile Leu Glu Asn Val Glu His Ala Tyr
145                 150                 155                 160

Gly Met Arg Ala Ala Gln Phe His Ala Arg Phe Met Asp Ala Ile Thr
```

-continued

```
              165                 170                 175
Pro Thr Gly Thr Val Ile Thr Leu Leu Gly Leu Thr Pro Glu Gly His
            180                 185                 190

Arg Val Ala Val His Val Tyr Gly Thr Arg Gln Tyr Phe Tyr Met Asn
        195                 200                 205

Lys Glu Glu Val Asp Arg His Leu Gln Cys Arg Ala Pro Arg Asp Leu
    210                 215                 220

Cys Glu Arg Met Ala Ala Leu Arg Glu Ser Pro Gly Ala Ser Phe
225                 230                 235                 240

Arg Gly Ile Ser Ala Asp His Phe Glu Ala Glu Val Val Glu Arg Thr
                245                 250                 255

Asp Val Tyr Tyr Tyr Glu Thr Arg Pro Ala Leu Phe Tyr Arg Val Tyr
            260                 265                 270

Val Arg Ser Gly Arg Val Leu Ser Tyr Leu Cys Asp Asn Phe Cys Pro
        275                 280                 285

Ala Ile Lys Lys Tyr Glu Gly Gly Val Asp Ala Thr Thr Arg Phe Ile
    290                 295                 300

Leu Asp Asn Pro Gly Phe Val Thr Phe Gly Trp Tyr Arg Leu Lys Pro
305                 310                 315                 320

Gly Arg Asn Asn Thr Leu Ala Gln Pro Arg Ala Pro Met Ala Phe Gly
                325                 330                 335

Thr Ser Ser Asp Val Glu Phe Asn Cys Thr Ala Asp Asn Leu Ala Ile
            340                 345                 350

Glu Gly Gly Met Ser Asp Leu Pro Ala Tyr Lys Leu Met Cys Phe Asp
        355                 360                 365

Ile Glu Cys Lys Ala Gly Gly Glu Asp Glu Leu Ala Phe Pro Val Ala
    370                 375                 380

Gly His Pro Glu Asp Leu Val Ile Gln Ile Ser Cys Leu Leu Tyr Asp
385                 390                 395                 400

Leu Ser Thr Thr Ala Leu Glu His Val Leu Leu Phe Ser Leu Gly Ser
                405                 410                 415

Cys Asp Leu Pro Glu Ser His Leu Asn Glu Leu Ala Ala Arg Gly Leu
            420                 425                 430

Pro Thr Pro Val Val Leu Glu Phe Asp Ser Glu Phe Glu Met Leu Leu
        435                 440                 445

Ala Phe Met Thr Leu Val Lys Gln Tyr Gly Pro Glu Phe Val Thr Gly
    450                 455                 460

Tyr Asn Ile Ile Asn Phe Asp Trp Pro Phe Leu Leu Ala Lys Leu Thr
465                 470                 475                 480

Asp Ile Tyr Lys Val Pro Leu Asp Gly Tyr Gly Arg Met Asn Gly Arg
                485                 490                 495

Gly Val Phe Arg Val Trp Asp Ile Gly Gln Ser His Phe Gln Lys Arg
            500                 505                 510

Ser Lys Ile Lys Val Asn Gly Met Val Asn Ile Asp Met Tyr Gly Ile
        515                 520                 525

Ile Thr Asp Lys Ile Lys Leu Ser Ser Tyr Lys Leu Asn Ala Val Ala
    530                 535                 540

Glu Ala Val Leu Lys Asp Lys Lys Asp Leu Ser Tyr Arg Asp Ile
545                 550                 555                 560

Pro Thr Tyr Tyr Ala Ala Gly Pro Ala Gln Arg Gly Val Ile Gly Glu
                565                 570                 575

Tyr Cys Ile Gln Asp Ser Leu Leu Val Gly Gln Leu Phe Phe Lys Phe
            580                 585                 590
```

-continued

```
Leu Pro His Leu Glu Leu Ser Ala Val Ala Arg Leu Ala Gly Ile Asn
        595                 600                 605

Ile Thr Arg Thr Ile Tyr Asp Gly Gln Gln Ile Arg Val Phe Thr Cys
        610                 615                 620

Leu Leu Arg Leu Ala Asp Gln Lys Gly Phe Ile Leu Pro Asp Thr Gln
625                 630                 635                 640

Gly Arg Phe Arg Gly Ala Gly Gly Glu Ala Pro Lys Arg Pro Ala Ala
                645                 650                 655

Ala Arg Glu Asp Glu Glu Arg Pro Glu Glu Gly Glu Asp Glu Asn
        660                 665                 670

Glu Arg Glu Glu Gly Gly Gly Glu Arg Glu Pro Glu Gly Ala Arg Glu
        675                 680                 685

Thr Ala Gly Arg His Val Gly Tyr Gln Gly Ala Arg Val Leu Asp Pro
690                 695                 700

Thr Ser Gly Phe His Val Asn Pro Val Val Phe Asp Phe Ala Ser
705                 710                 715                 720

Leu Tyr Pro Ser Ile Ile Gln Ala His Asn Leu Cys Phe Ser Thr Leu
                725                 730                 735

Ser Leu Arg Ala Asp Ala Val Ala His Leu Glu Ala Gly Lys Asp Tyr
                740                 745                 750

Leu Glu Ile Glu Val Gly Gly Arg Arg Leu Phe Phe Val Lys Ala His
        755                 760                 765

Val Arg Glu Ser Leu Leu Ser Ile Leu Leu Arg Asp Trp Leu Ala Met
770                 775                 780

Arg Lys Gln Ile Arg Ser Arg Ile Pro Gln Ser Ser Pro Glu Glu Ala
785                 790                 795                 800

Val Leu Leu Asp Lys Gln Gln Ala Ala Ile Lys Val Val Cys Asn Ser
                805                 810                 815

Val Tyr Gly Phe Thr Gly Val Gln His Gly Leu Leu Pro Cys Leu His
                820                 825                 830

Val Ala Ala Thr Val Thr Thr Ile Gly Arg Glu Met Leu Leu Ala Thr
        835                 840                 845

Arg Glu Tyr Val His Ala Arg Trp Ala Ala Phe Glu Gln Leu Leu Ala
850                 855                 860

Asp Phe Pro Glu Ala Ala Asp Met Arg Ala Pro Gly Pro Tyr Ser Met
865                 870                 875                 880

Arg Ile Ile Tyr Gly Asp Thr Asp Ser Ile Phe Val Leu Cys Arg Gly
                885                 890                 895

Leu Thr Ala Ala Gly Leu Thr Ala Val Gly Asp Lys Met Ala Ser His
                900                 905                 910

Ile Ser Arg Ala Leu Phe Leu Pro Pro Ile Lys Leu Glu Cys Glu Lys
        915                 920                 925

Thr Phe Thr Lys Leu Leu Ile Ala Lys Lys Lys Tyr Ile Gly Val
        930                 935                 940

Ile Tyr Gly Gly Lys Met Leu Ile Lys Gly Val Asp Leu Val Arg Lys
945                 950                 955                 960

Asn Asn Cys Ala Phe Ile Asn Arg Thr Ser Arg Ala Leu Val Asp Leu
                965                 970                 975

Leu Phe Tyr Asp Asp Thr Val Ser Gly Ala Ala Ala Leu Ala Glu
                980                 985                 990

Arg Pro Ala Glu Glu Trp Leu Ala  Arg Pro Leu Pro Glu  Gly Leu Gln
        995                 1000                 1005
```

-continued

```
Ala Phe Gly Ala Val Leu Val Asp Ala His Arg Arg Ile Thr Asp
    1010                1015                1020

Pro Glu Arg Asp Ile Gln Asp Phe Val Leu Thr Ala Glu Leu Ser
    1025                1030                1035

Arg His Pro Arg Ala Tyr Thr Asn Lys Arg Leu Ala His Leu Thr
    1040                1045                1050

Val Tyr Tyr Lys Leu Met Ala Arg Arg Ala Gln Val Pro Ser Ile
    1055                1060                1065

Lys Asp Arg Ile Pro Tyr Val Ile Val Ala Gln Thr Arg Glu Val
    1070                1075                1080

Glu Glu Thr Val Ala Arg Leu Ala Ala Leu Arg Glu Leu Asp Ala
    1085                1090                1095

Ala Ala Pro Gly Asp Glu Pro Ala Pro Pro Ala Ala Leu Pro Ser
    1100                1105                1110

Pro Ala Lys Arg Pro Arg Glu Thr Pro Ser Pro Ala Asp Pro Pro
    1115                1120                1125

Gly Gly Ala Ser Lys Pro Arg Lys Leu Leu Val Ser Glu Leu Ala
    1130                1135                1140

Glu Asp Pro Ala Tyr Ala Ile Ala His Gly Val Ala Leu Asn Thr
    1145                1150                1155

Asp Tyr Tyr Phe Ser His Leu Leu Gly Ala Ala Cys Val Thr Phe
    1160                1165                1170

Lys Ala Leu Phe Gly Asn Asn Ala Lys Ile Thr Glu Ser Leu Leu
    1175                1180                1185

Lys Arg Phe Ile Pro Glu Val Trp His Pro Pro Asp Asp Val Ala
    1190                1195                1200

Ala Arg Leu Arg Thr Ala Gly Phe Gly Ala Val Gly Ala Gly Ala
    1205                1210                1215

Thr Ala Glu Glu Thr Arg Arg Met Leu His Arg Ala Phe Asp Thr
    1220                1225                1230

Leu Ala
    1235

<210> SEQ ID NO 19
<211> LENGTH: 1235
<212> TYPE: PRT
<213> ORGANISM: herpes simplex

<400> SEQUENCE: 19

Met Phe Ser Gly Gly Gly Gly Pro Leu Ser Pro Gly Gly Lys Ser Ala
1               5                   10                  15

Ala Arg Ala Ala Ser Gly Phe Phe Ala Pro Ala Gly Pro Arg Gly Ala
                20                  25                  30

Gly Arg Gly Pro Pro Pro Cys Leu Arg Gln Asn Phe Tyr Asn Pro Tyr
            35                  40                  45

Leu Ala Pro Val Gly Thr Gln Gln Lys Pro Thr Gly Pro Thr Gln Arg
        50                  55                  60

His Thr Tyr Tyr Ser Glu Cys Asp Glu Phe Arg Phe Ile Ala Pro Arg
65                  70                  75                  80

Val Leu Asp Glu Asp Ala Pro Pro Glu Lys Arg Ala Gly Val His Asp
                85                  90                  95

Gly His Leu Lys Arg Ala Pro Lys Val Tyr Cys Gly Gly Asp Glu Arg
            100                 105                 110

Asp Val Leu Arg Val Gly Ser Gly Gly Phe Trp Pro Arg Arg Ser Arg
        115                 120                 125
```

```
Leu Trp Gly Gly Val Asp His Ala Pro Ala Gly Phe Asn Pro Thr Val
130                 135                 140

Thr Val Phe His Val Tyr Asp Ile Leu Glu Asn Val Glu His Ala Tyr
145                 150                 155                 160

Gly Met Arg Ala Ala Gln Phe His Ala Arg Phe Met Asp Ala Ile Thr
                165                 170                 175

Pro Thr Gly Thr Val Ile Thr Leu Leu Gly Leu Thr Pro Glu Gly His
                180                 185                 190

Arg Val Ala Val His Val Tyr Gly Thr Arg Gln Tyr Phe Tyr Met Asn
            195                 200                 205

Lys Glu Glu Val Asp Arg His Leu Gln Cys Arg Ala Pro Arg Asp Leu
        210                 215                 220

Cys Glu Arg Met Ala Ala Leu Arg Glu Ser Pro Gly Ala Ser Phe
225                 230                 235                 240

Arg Gly Ile Ser Ala Asp His Phe Glu Ala Glu Val Val Glu Arg Thr
                245                 250                 255

Asp Val Tyr Tyr Tyr Glu Thr Arg Pro Ala Leu Phe Tyr Arg Val Tyr
                260                 265                 270

Val Arg Ser Gly Arg Val Leu Ser Tyr Leu Cys Asp Asn Phe Cys Pro
        275                 280                 285

Ala Ile Lys Lys Tyr Glu Gly Gly Val Asp Ala Thr Thr Arg Phe Ile
290                 295                 300

Leu Asp Asn Pro Gly Phe Val Thr Phe Gly Trp Tyr Arg Leu Lys Pro
305                 310                 315                 320

Gly Arg Asn Asn Thr Leu Ala Gln Pro Arg Ala Pro Met Ala Phe Gly
                325                 330                 335

Thr Ser Ser Asp Val Glu Phe Asn Cys Thr Ala Asp Asn Leu Ala Ile
                340                 345                 350

Glu Gly Gly Met Ser Asp Leu Pro Ala Tyr Lys Leu Met Cys Phe Asp
            355                 360                 365

Ile Glu Cys Lys Ala Gly Gly Glu Asp Glu Leu Ala Phe Pro Val Ala
        370                 375                 380

Gly His Pro Glu Asp Leu Val Ile Gln Ile Ser Cys Leu Leu Tyr Asp
385                 390                 395                 400

Leu Ser Thr Thr Ala Leu Glu His Val Leu Leu Phe Ser Leu Gly Ser
                405                 410                 415

Cys Asp Leu Pro Glu Ser His Leu Asn Glu Leu Ala Ala Arg Gly Leu
                420                 425                 430

Pro Thr Pro Val Val Leu Glu Phe Asp Ser Glu Phe Glu Met Leu Leu
                435                 440                 445

Ala Phe Met Thr Leu Val Lys Gln Tyr Gly Pro Glu Phe Val Thr Gly
450                 455                 460

Tyr Asn Ile Ile Asn Phe Asp Trp Pro Phe Leu Leu Ala Lys Leu Thr
465                 470                 475                 480

Asp Ile Tyr Lys Val Pro Leu Asp Gly Tyr Gly Arg Met Asn Gly Arg
                485                 490                 495

Gly Val Phe Arg Val Trp Asp Ile Gly Gln Ser His Phe Gln Lys Arg
                500                 505                 510

Ser Lys Ile Lys Val Asn Gly Met Val Asn Ile Asp Met Tyr Gly Ile
            515                 520                 525

Ile Thr Asp Lys Ile Lys Leu Ser Ser Tyr Lys Leu Asn Ala Val Ala
530                 535                 540
```

-continued

```
Glu Ala Val Leu Lys Asp Lys Lys Asp Leu Ser Tyr Arg Asp Ile
545                 550                 555                 560

Pro Ala Tyr Tyr Ala Gly Pro Ala Gln Arg Gly Val Ile Gly Glu
                565                 570                 575

Tyr Cys Ile Gln Asp Ser Leu Leu Val Gly Gln Leu Phe Phe Lys Phe
                580                 585                 590

Leu Pro His Leu Glu Leu Ser Ala Val Ala Arg Leu Ala Gly Ile Asn
        595                 600                 605

Ile Thr Arg Thr Ile Tyr Asp Gly Gln Gln Ile Arg Val Phe Thr Cys
    610                 615                 620

Leu Leu Arg Leu Ala Asp Gln Lys Gly Phe Ile Leu Pro Asp Thr Gln
625                 630                 635                 640

Gly Arg Phe Arg Gly Gly Gly Glu Ala Pro Lys Arg Pro Ala Ala
                645                 650                 655

Ala Arg Glu Asp Glu Glu Arg Pro Glu Glu Gly Glu Asp Glu Asp
                660                 665                 670

Glu Arg Glu Glu Gly Gly Gly Glu Arg Glu Pro Glu Gly Ala Arg Glu
    675                 680                 685

Thr Ala Gly Arg His Val Gly Tyr Gln Gly Ala Arg Val Leu Asp Pro
690                 695                 700

Thr Ser Gly Phe His Val Asn Pro Val Val Phe Asp Phe Ala Ser
705                 710                 715                 720

Leu Tyr Pro Ser Ile Ile Gln Ala His Asn Leu Cys Phe Ser Thr Leu
                725                 730                 735

Ser Leu Arg Ala Asp Ala Val Ala His Leu Glu Ala Gly Lys Asp Tyr
                740                 745                 750

Leu Glu Ile Glu Val Gly Gly Arg Leu Phe Phe Val Lys Ala His
        755                 760                 765

Val Arg Glu Ser Leu Leu Ser Ile Leu Leu Arg Asp Trp Leu Ala Met
770                 775                 780

Arg Lys Gln Ile Arg Ser Arg Ile Pro Gln Ser Ser Pro Glu Glu Ala
785                 790                 795                 800

Val Leu Leu Asp Lys Gln Gln Ala Ala Ile Lys Val Val Cys Asn Ser
                805                 810                 815

Val Tyr Gly Phe Thr Gly Val Gln His Gly Leu Leu Pro Cys Leu His
                820                 825                 830

Val Ala Ala Thr Val Thr Thr Ile Gly Arg Glu Met Leu Leu Ala Thr
                835                 840                 845

Arg Glu Tyr Val His Ala Arg Trp Ala Ala Phe Glu Gln Leu Leu Ala
850                 855                 860

Asp Phe Pro Glu Ala Ala Asp Met Arg Ala Pro Gly Pro Tyr Ser Met
865                 870                 875                 880

Arg Ile Ile Tyr Gly Asp Thr Asp Ser Ile Phe Val Leu Cys Arg Gly
                885                 890                 895

Leu Thr Ala Ala Gly Leu Thr Ala Val Gly Asp Lys Met Ala Ser His
                900                 905                 910

Ile Ser Arg Ala Leu Phe Leu Ser Pro Ile Lys Leu Glu Cys Glu Lys
                915                 920                 925

Thr Phe Thr Lys Leu Leu Ile Ala Lys Lys Tyr Ile Gly Val
                930                 935                 940

Ile Tyr Gly Gly Lys Met Leu Ile Lys Gly Val Asp Leu Val Arg Lys
945                 950                 955                 960

Asn Asn Cys Ala Phe Ile Asn Arg Thr Ser Arg Ala Leu Val Asp Leu
```

-continued

```
                     965                 970                 975
Leu Phe Tyr Asp Asp Thr Val Ser Gly Ala Ala Ala Ala Leu Ala Glu
                980                 985                 990
Arg Pro Ala Glu Glu Trp Leu Ala Arg Pro Leu Pro Glu Gly Leu Gln
                995                1000                1005
Ala Phe Gly Ala Val Leu Val Asp Ala His Arg Arg Ile Thr Asp
           1010                1015                1020
Pro Glu Arg Asp Ile Gln Asp Phe Val Leu Thr Ala Glu Leu Ser
           1025                1030                1035
Arg His Pro Arg Ala Tyr Thr Asn Lys Arg Leu Ala His Leu Thr
           1040                1045                1050
Val Tyr Tyr Lys Leu Met Ala Arg Arg Ala Gln Val Pro Ser Ile
           1055                1060                1065
Lys Asp Arg Ile Pro Tyr Val Ile Val Ala Gln Thr Arg Glu Val
           1070                1075                1080
Glu Glu Thr Val Ala Arg Leu Ala Ala Leu Arg Glu Leu Asp Ala
           1085                1090                1095
Ala Ala Pro Gly Asp Glu Pro Ala Pro Pro Ala Ala Leu Pro Ser
           1100                1105                1110
Pro Ala Lys Arg Pro Arg Glu Thr Pro Leu His Ala Asp Pro Pro
           1115                1120                1125
Gly Gly Ala Ser Lys Pro Arg Lys Leu Leu Val Ser Glu Leu Ala
           1130                1135                1140
Glu Asp Pro Ala Tyr Ala Ile Ala His Gly Val Ala Leu Asn Thr
           1145                1150                1155
Asp Tyr Tyr Phe Ser His Leu Leu Gly Ala Ala Cys Val Thr Phe
           1160                1165                1170
Lys Ala Leu Phe Gly Asn Asn Ala Lys Ile Thr Glu Ser Leu Leu
           1175                1180                1185
Lys Arg Phe Ile Pro Glu Val Trp His Pro Pro Asp Asp Val Ala
           1190                1195                1200
Ala Arg Leu Arg Ala Ala Gly Phe Gly Ala Val Gly Ala Gly Ala
           1205                1210                1215
Thr Ala Glu Glu Thr Arg Arg Met Leu His Arg Ala Phe Asp Thr
           1220                1225                1230
Leu Ala
1235
```